US008389806B2

(12) United States Patent
Phillips et al.

(10) Patent No.: US 8,389,806 B2
(45) Date of Patent: Mar. 5, 2013

(54) VASCULAR-PREFERRED PROMOTERS

(75) Inventors: Jonathan Phillips, Auckland (NZ); Sathish Puthigae, Auckland (NZ); JiaLong Yao, Auckland (NZ); Barry Flinn, New Brunswick (CA); Richard S. Forster, Auckland (NZ); Clare Eagleton, Auckland (NZ)

(73) Assignee: Arborgen Inc., Ridgeville, SC (US)

( * ) Notice: Subject to any disclaimer, the term of this patent is extended or adjusted under 35 U.S.C. 154(b) by 848 days.

(21) Appl. No.: 12/205,329

(22) Filed: Sep. 5, 2008

(65) Prior Publication Data

US 2009/0031452 A1    Jan. 29, 2009

Related U.S. Application Data

(62) Division of application No. 10/717,897, filed on Nov. 21, 2003, now Pat. No. 7,442,786.

(60) Provisional application No. 60/428,287, filed on Nov. 22, 2002.

(51) Int. Cl.
*C12N 15/82* (2006.01)
*A01H 5/00* (2006.01)

(52) U.S. Cl. ... 800/287; 536/24.1; 536/24.5; 435/320.1; 435/419; 435/430; 435/468; 800/278; 800/298

(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. | |
| 5,451,514 A | 9/1995 | Boudet et al. | |
| 5,565,340 A | 10/1996 | Chenchik et al. | |
| 5,759,822 A | 6/1998 | Chenchik et al. | |
| 6,051,757 A | 4/2000 | Barton et al. | |
| 6,132,970 A | 10/2000 | Stemmer | |
| 6,187,994 B1 | 2/2001 | Baszcynski et al. | |
| 6,204,434 B1 * | 3/2001 | Bloksberg et al. | 800/290 |
| 6,410,718 B1 * | 6/2002 | Bloksberg et al. | 536/23.6 |
| 6,506,559 B1 | 1/2003 | Fire et al. | |
| 6,518,485 B1 | 2/2003 | Connett-Porceddu et al. | |
| 6,596,925 B1 | 7/2003 | Perera et al. | |
| 2003/0101478 A1 | 5/2003 | Perera et al. | |
| 2004/0146904 A1 | 7/2004 | Phillips | |

FOREIGN PATENT DOCUMENTS

| | | |
|---|---|---|
| EP | 0 120 516 B1 | 10/1991 |
| EP | 0 154 204 B1 | 1/1994 |
| EP | 0 271 988 B1 | 8/1995 |
| EP | 0 271 988 Ba | 8/1995 |
| WO | WO 92/04449 | 3/1992 |
| WO | WO 93/19189 | 9/1993 |
| WO | WO 94/23044 | 10/1994 |
| WO | WO 99/61631 | 12/1999 |
| WO | WO 01/20008 A2 | 3/2001 |
| WO | WO 01/98485 | 12/2001 |
| WO | WO 01/98485 A1 | 12/2001 |
| WO | WO 02/44337 A2 | 6/2002 |
| WO | WO 2004/108903 | 12/2004 |
| WO | WO 2004/108903 A2 | 12/2004 |

OTHER PUBLICATIONS

Kim Y et al. A 20 nucleotide upstream element is essential for the nopaline synthase (nos) promoter activity. Plant Mol Biol. Jan. 1994;24(1):105-17.*
Buzeli R.A. et al. Tissue-specific regulation of BiP genes: a cis-acting regulatory domain is required for BiP promoter activity in plant meristems. Plant Mol Biol. Nov. 2002;50(4-5):757-71.*
Gillespie D. The magic and challenge of DNA probes as diagnostic reagents. Vet Microbiol. Sep. 1990;24(3-4):217-33. Review.*
Bevan M. et al. Tissue- and cell-specific activity of a phenylalanine ammonia-lyase promoter in transgenic plants. EMBO J. Jul. 1989:8(7)1 899-906.*
Franken P. et al. The duplicated chalcone synthase genes C2 and Whp (white pollen) of Zea mays are independently regulated; evidence for translational control of Whp expression by the anthocyanin intensifying gene in. EMBO J. Sep. 1991;10(9):2605-12.*
Okada K. et al. Five geranylgeranyl diphosphate synthases expressed in different organs are localized into three subcellular compartments in Arabidopsis. Plant Physiol. Apr. 2000;122(4):1045-56.*
Elbashir et al. Functional anatomy of siRNAs for mediating efficient RNAi in Drosophila melanogaster embryo lysate. EMBO J. Dec. 3, 2001;20(23):6877-88.*
Lauvergeat, V. et al., "The vascular expression pattern directed by the *Eucalyptus gennii* cinnamyl alcohol dehydrogenase EgCAD2 promoter is conserved among woody and herbaceous plant species", *Plant Molecular Biology*, 50, 2002, pp. 497-509.
Office Action(English Translation) of Japanese Patent Application No. 2004-555614, dated Sep. 8, 2009. (14 pgs.).
Ausubel, et al., (eds.), "Current Protocols in Molecular Biology", (John Wiley & Sons,Inc.), (1990).
Bevan, et al., "Tissue-and cell-specific activity of a phenylalanine ammonia-lyase promoter in transgenic plants", EMBO J., Jul. 1989, 8(7), pp. 1899-1906.
Buzeli R.A., et al., "Tissue-specific regulation of BiP genes: a cis-acting regulatory domain is required for BiP promoter activity in plant meristerns.", Plant Mol Biol., Nov. 2002, 50(4-5). pp. 757-771.
E. T. Bolton et al., "A General Method for the Isolation of RNA Complementary to DNA", Biochemistry: Bolton and McCarthy, Proc. Natl. Acad. Sci., 1962, vol. 48, pp. 1390-1397,.
Eugene W. Holowachuk et al., "Efficient Gene Synthesis by Klenow Assembly / Extension—Pfu Polymerase Amplification (KAPPA) of Overlapping Oligonucleotides", PCR Methods and Applications, Cold Spring Harbor Laboratory, vol. 4, pp. 299-302.
Gillespie D., "The magic and challenge of DNA probes as diagnostic reagents.", Vet Microbiol., Sep. 24, 1990, (3-4), pp. 217-233. Review.
Kawaoka et al., "Functional analysis of tobacco LIM protein Ntlinl involved in lignin biosynthesis," The Plant Journal, vol. 22, No. 4, 2000, pp. 289-301.
Kim Y, et al., "A 20 nucleotide upstream element is essential for the nopaline synthase (nos) promoter activity.", Plant Mol Biol., Jan. 24, 1994, (1), pp. 105-117.

(Continued)

*Primary Examiner* — Cynthia Collins
(74) *Attorney, Agent, or Firm* — Foley & Lardner LLP

(57) ABSTRACT

The present invention relates to the regulation of polynucleotide transcription and/or expression. In particular, this invention relates to polynucleotide regulatory sequences isolated from *Eucalyptus grandis* and *Pinus radiata* that are capable of conferring vascular-preferred polynucleotide transcription in plant cells. Constructs and methods for using the inventive regulatory sequences for modifying transcription of endogenous and/or heterologous polynucleotides also are included in the invention.

18 Claims, 4 Drawing Sheets

OTHER PUBLICATIONS

Michael A. Wosnick et al., "Rapid Construction of Large Synthetic Genes: Total Chemical Synthesis of Two Different Versions of the Bovine Prochymosin Gene", Gene, Elsevier Science Publishers, vol. 60, No. 1, pp. 115-127.

Polvere R.I., et al., GeneBank Accession No. U88240, *Trichinella spiralis* hypothetical ORF 2.20 mRNA, partial cds, Mar. 4, 1997.

R. B. Horsch et al., Rapid Assay of Foreign Gene Expression in Leaf Discs Transformed by *Agrobacterium tumefaciens*: Role of T-DNA Borders in the Transfer Process, Proc. Natl. Acad, Sci. USA, Jun. 1986, vol. 83, pp. 4428-4432.

U.S. Appl. No. 60/476,222, filed Jun. 6, 2003, Chang et al.

"Crop Species", Handbook of Plant Cell Culture, 1990 UCLA Symposium on Molecular Strategies for Crop Improvement, 3 pages.

Akio Hayashimoto et al., "A Polyethylene Glycol=Mediated Protoplast Transformation System for Production of Fertile Transgenic Rice Plants", Plant Physiology, The American Society of Plant Physiologists, Jul. 1990, vol. 93, No. 3, pp. 857-863.

Alan H. Christensen et al., "Ubiquitin Promoter-based Vectors for High Level Expression of Selectable and/or Screenable Marker Genes in Monocotyledonous Plants", Transgenic Research, Chapman & Hall, May 1996, vol. 5, No. 3, pp. 213-218.

Antonio Leyva et al., "*cis*-Element Combinations Determine Phenylalanine Ammonia-Lyase Gene Tissue-Specific Expression Patterns", The Plant Cell, 1992 American Society of Plant Physiologists, Mar. 1992, vol. 4, pp. 263-271.

Aronen, Tuija, Genetic transformation of Scots pine (*Pinus sylvestris* L.), Dissertation Metsäntutkimuslaitoksen tiedonantoja 595, 1996, pp. 8-53.

Ausubel, et al., (eds.), "Current Protocols in Molecular Biology", (John Wiley & Sons,lnc.), (1990).

Ausubel, et al., (eds.), "Short Protocols in Molecular Biology", 3$^{rd}$ ed. (John Wiley & Sons, Inc.), (1995).

B. L. Miki et al., "Procedures for Introducing Foreign DNA into Plants", Methods in Plant Molecular Biology and Biotechnology, CRC Press, 1993, pp. 67-88.

Beat Keller et al., "Vascular Expression of a Bean Cell Wall Glycine-rich Protein—beta—glucuronidase Gene Fusion in Transgenic Tobacco", The Embo Journal, IRL Press Limited, May 1989, vol. 8, No. 5, pp. 1309-1314.

Beat Keller et al., "Vascular expression of the *grp1.8* promoter is controlled by three specific regulatory elements and one unspecific activating sequence", Plant Molecular Biology, International Society for Plant Molecular Biology, Kluwer Academic Publishers, Oct. 1994, vol. 26, No. 2, pp. 747-756.

Bevan, et al., "Tissue and Cell-Specific Activity of a Phenylalanine Ammonia-Lyase Promoter in Transgenic Plants", *EMBO J.*, Jul. 1989, 8(7), pp. 1899-906.

Bugos et al., "cDNA cloning, sequence analysis and seasonal expression of lignin-bispecific caffeic acid/5-hydroxyferulic acid O-methyltransferase of aspen," Plant Molecular Biology, vol. 17, 1991, pp. 1203-1215.

Buzeli R.A., et al., Tissue-Specific Regulation of BiP Genes: a Cis-Acting Regulatory Domain is Required for BiP Promoter Activity in Plant Meristerms, *Plant Mol Biol.*, 2002, 50(4-5); pp. 757-771.

C. Grand et al., "Inhibition of Cinnamyl-alcohol-dehydrogenase Activity and Lignin Synthesis in Poplar (*Populus X euramericana* Dode) Tissues by Two Organic Compounds", Planta, Springer-Verlag, 1985, vol. 163, No. 2, pp. 232-237.

C.J.S.Smith et al., "Antisense RNA Inhibition of Polygalacturonase Gene Expression in Transgenic Tomatoes", Nature, Aug. 1988, vol. 334, No. 25, pp. 724-726.

Carol A. Loopstra et al., "Xylem-Specific Gene Expression in Loblolly Pine", Plant Molecular Biology, International Society for Plant Molecular Biology, Kluwer Academic Publishers, Jan. 1995, vol. 27, No. 2, pp. 277-291.

Catherine Feuillet et al., "Tissue- and Cell-Specific Expression of a Cinnamyl Alcohol Dehydrogenase Promoter in Transgenic Poplar Plants", Plant Molecular Biology, International Society for Plant Molecular Biology, Kluwer Academic Publishers, Feb. 1995, vol. 27, No. 4, pp. 651-667.

Cathie Martin et al., "MYB Transcription Factors in Plants", Trends in Genetics, 1997 Elsevier Science Ltd., Feb. 1997, vol. 13, No. 2, pp. 67-73.

Chang et al., "A Simple and Efficient Method for Isolating RNA from Pine Trees", Plant Molecular Biology Reporter, Transaction Periodicals Consortium, Rutgers University, Jun. 1993, vol. 11, No. 2, pp. 113-116.

Christopher J.S. Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

D. Palitha Dharmawardhana et al., "cDNA Cloning and Heterologous Expression of Coniferin beta-glucosidase", Plant Molecular Biology, International Society for Plant Molecular Biology, Kluwer Academic Publishers, May 1999, vol. 40, No. 2, pp. 365-372.

Datta et al., "Nucleotide sequence of a gene encoding soybean repetitive praline-rich protein 3," *Plant Molecular Biology*, 1990, pp. 285-286, vol. 14, Kluwer Academic Publishers, Belgium.

David A. Neustaedter et al., "A Novel Parsley *4CL1 cis*-element is Required for Developmentally Regulated Expression and Protein DNA Complex Formation", The Plant Journal, 1999, Blackwell Science Ltd., vol. 18, No. 1, pp. 77-88.

David M. Stalker et al., "Purification and Properties of a Nitrilase Specific for the Herbicide Bromoxynil and Corresponding Nucleotide Sequence Analysis of the bxn Gene", The Journal of Biological Chemistry, The American Society for Biochemistry and Molecular Biology, Inc., May 5, 1988, vol. 263, No. 13, pp. 6310-6314.

David McElroy et al., "Isolation of an Efficient Actin Promoter for Use in Rice Transformation", The Plant Cell, 1990 American Society of Plant Physiologists, Feb. 1990, vol. 2, pp. 163-171.

Diane Hatton et al., "Two Classes of CIS Sequences Contribute to Tissue-Specific Expression of a PAL2 Promoter in Transgenic Tobacco", The Plant Journal, 1995, vol. 7, No. 6, pp. 859-876.

Donald R. Needham et al., "Characterization of an Adduct Between CC-1065 and a Defined Oligodeoxynucleotide Duplex", Nucleic Acids Research, IRL Press Limited, 1984, vol. 12, No. 15, pp. 6159-6168.

Dorothea Wyrambik et al., "Purification and Properties of Isoenzymes of Cinnamyl-Alcohol Dehydrogenase from Soybean-Cell-Suspension Cultures", European Journal of Biochemistry, Springer-Verlag, Nov. 1975, vol. 59, No. 1, pp. 9-15.

E. T. Bolton et al., "A General Method for the Isolation of RNA Complementary to DNA", Biochemistry: Bolton and McCarthy, Proc. Natl. Acad. Sci., 1962, vol. 48, pp. 1390-1397.

Ellis et al., "Stable transformation of *Picea glauca* by Particle Acceleration," Biotechnology, vol. 11, Jan. 1993, pp. 84-89.

Eric Lacombe et al., Characterization of *cis*-elements Required for Vascular Expression of the *Cinnamoyl CoA Reductase* Gene and for Protein DNA Complex Formation, The Plant Journal, 2000 Blackwell Science Ltd., vol. 23, No. 5, pp. 663-676.

Eugene W. Holowachuk et al., "Efficient Gene Synthesis by Klenow Assembly / Extension—Pfu Polymerase Amplification (KAPPA) of Overlapping Oligonucleotides", PCR Methods and Applications, Cold Spring Harbor Laboratory, vol. 4, pp. 299-302, 1995.

Eun-Gyu No et al., "Sequences Upstream and Downstream of Two Xylem-Specific Pine Genes Influence Their Expression", Plant Science, 2000 Elsevier Science, vol. 160, pp. 77-86.

Gleave et al., "A versatile binary vector system with a T-DNA organizational structure conducive to efficient integration of cloned DNA into the plant genome," Plant Molecular Biology, vol. 20, 1992, pp. 1203-1207.

Golovkin et al., "Production of transgenic maize plants by direct DNA uptake into embryogenic protoplasts," *Plant Science*, 1993, pp. 41-52, vol. 90, Elsevier Scientific Publishers Ireland Ltd.

Gowri et al., Stress Responses in Alfalfa (*Medicago sativa* L.), Plant Physiol., vol. 97, 1991, pp. 7-14.

Halina Kononowicz, Subdomains of the Octopine Synthase Upstream Activating Element Direct Cell-Specific Expression in Transgenic Tobacco Plants, The Plant Cell, 1992 American Society of Plant Physiologists, Jan. 1992, vol. 4, pp. 17-27.

Harry J. Klee et al., "Vectors for Transformation of Higher Plants", Bio/Technology, Jul. 1985, vol. 3, pp. 637-642.

Heather Coleman et al., "Increased Growth and Yield by Altered Carbohydrate Allocation", Intl. Union of Forestry Research Organizations Biennial Conference in Umea, Sweden, Jun. 2003, 1 page.

Henry Daniell et al., "Containment of Herbicide Resistance Through Genetic Engineering of the Chloroplast Genome", Apr. 1998, Nature Biotechnology, vol. 16, pp. 345-348.

Huang et al., "*Agrobacterium rhizogenes*-mediated genetic transformation and regeneration of a conifer: *Larix Decidua*," In Vitro Cell. Dev. Biol., vol. 27P, Oct. 1991, pp. 201-207.

Ilan Levy et al., Modification of Polysaccharides and Plant Cell Wall by endo-1,4-beta-glucanase and Cellulose Binding Domains, Biomolecular Engineering, 2002 Elsevier Science B. V., vol. 19, pp. 17-30.

Ingo Potrykus et al., "Direct Gene Transfer to Cells of a Graminaceous Monocot", Mol. Gen. Genet, Springer-Verlag, 1985, vol. 199, pp. 183-188.

Ingrid M. Van Der Meer et al., "Antisense Inhibition of Flavonoid Biosynthesis in Petunia Anthers Results in Male Sterility", The Plant Cell, American Society of Plant Physiologists, Mar. 1992, vol. 4, pp. 253-262.

Izawa et al., "Plant bZIP Protein DNA Binding Specificity," J. Mol. Biol., vol. 230, 1993, pp. 1131-1144.

Jacqueline Grima-Pettenati et al., "Lignin Genetic Engineering Revisited", Plant Science, Elsevier Science Ireland Ltd., 1999, vol. 145, pp. 51-65.

Joëlle Thillet et al., "Site-Directed Mutagenesis of Mouse Dihydrofolate Reductase", The Journal of Biological Chemistry, The American Society for Biochemistry and Molecular Biology, Inc., Sep. 1968, vol. 263, No. 25, pp. 12500-12508.

Karl D. Hauffe et al., "Combinatorial Interactions Between Positive and Negative CIS-acting Elements Control Spatial Patterns of 4CL-1 Expression in Transgenic Tobacco", The Plant Journal, 1993, vol. 4, No. 2, pp. 235-253.

Kathleen D'Halluin et al., "Transgenic Maize Plants by Tissue Electroporation", The Plant Cell, 1992 Society of Plant Physiologists, Dec. 1992, vol. 4, pp. 1495-1505.

Kawaoka et al., "Functional analysis of tobacco LIM protein Ntlin1 involved in lignin biosynthesis," The Plant Journal, vol. 22, No. 4, 2000, pp. 289-301.

Kim Y., et al., "A 20 Nucleotide Upstream Element is Essential for the Nopaline Synthase (nos) Promoter Activity", *Plant Mol Biol.*, Jan. 1994, 24(1), pp. 105-117.

Luis Herrara-Estrella et al., Expression of Chimaeric Genes Transferred into Plant Cells Using a Ti-plasmid-derived Vector, Nature, International Weekly Journal of Science, Macmillan Journals Ltd., May 19-25, 1983, vol. 303, No. 5914, pp. 209-213.

Marie Baucher et al., "Red Xylem and Higher Lignin Extractability by Down-Regulating a Cinnamyl Alcohol Dehydrogenase in Poplar", Plant Physioll, 1996, vol. 112, pp. 1479-1490.

Marita et al., "NMR characterization of lignins from transgenic poplars with suppressed caffeic acid O-methyltransferase activity," J. Chem. Soc. Perkin Trans. 1, 2001, pp. 2939-2945.

Mark D. Burow et al., "High Frequency Generation of Transgenic Tobacco Plants after Modified Leaf Disk Cocultivation with *Agrobacterium tumefaciens*", Plant Molecular Biology Reporter, Transaction Periodicals Consortium, Rutgers University, May 1990, vol. 8, No. 2, pp. 124-139.

Maud A. W. Hinchee et al., "Production of Transgenic Soybean Plants Using Agrobacterium-Mediated DNA Transfer", Bio/Technology, The International Monthly for Industrial Biology, Aug. 1988, vol. 6, pp. 915-922.

McCarthy et al., "The Rate of Change of DNA in Evolution," *In Evolution of Genetic Systems*, 1972, pp. 1-43, H.H. Smith (ed.), Brookhaven Symposium in Biology No. 23, Gordon and Breach, New York.

Menkens et al., "The G-box: a ubiquitous regulatory DNA element in plants bound by the GBF family of bZIP proteins," TIBS, Dec. 1995, pp. 506-510.

Michael A. Wosnick et al., "Rapid Construction of Large Synthetic Genes: Total Chemical Synthesis of Two Different Versions of the Bovine Prochymosin Gene", Gene, Elsevier Science Publishers, vol. 60, No. 1, pp. 115-127, 1987.

Michael Bevan, "Binary *Argrobacterium* Vectors for Plant Transformation", IRL Press Limited, 1984, vol. 12, No. 22, pp. 8711-8721.

Michael J. Adang et al., "The Reconstruction and Expression of a *Bacillus thuringiensis cry IIIA* gene in protoplasts and potato plants", Plant Molecular Biology, Mar. 1993, vol. 21, No. 6, pp. 1131-1145.

Nabila Yahioui et al., "Comparative Efficiency of Different Constructs for Down Regulation of Tobacco Cinnamyl Alcohol Dehydrogenase", Phytochemistry, Elsevier Science Ltd., 1998, vol. 49, No. 2, pp. 295-306.

Narumi Matsuda et al., "Partial Male Sterility in Transgenic Tobacco Carrying Antisense and Sense *PAL* cDNA Under the Control of a Tapetum-Specific Promoter", Plant & Cell Physiology, The Japanese Society of Plant Physiologists, Mar. 1996, vol. 37, No. 2, pp. 215-222.

Patrick Dillon et al., "Use of Polymerase Chain Reaction for the Rapid Construction of Synthetic Genes", PCR Protocols: Current Methods and Applications, Methods in Molecular Biology, 1993, Humana Press Inc., vol. 15, pp. 263-268.

Patrick Paddison et al., "Short Hairpin RNAs (shRNAs) Induce Sequence-Specific Silencing in Mammalian Cells", Genes & Development, Cold Spring Laboratory Press, 2002, vol. 16, pp. 948-958.

Pearson, et al., *Proc. Natl. Acad. Sci.*, vol. 85, pp. 2444-2448, (1988) USA.

Pearson, *Methods in Enzymol.*, vol. 183, pp. 63-98, (1990).

Perera, J.R., et al., US-09-598401C-113, sequence alignment between SEQ ID No. 3 and SEQ ID No. 113 of U.S. Patent No. 6,596,925, issued Jul. 2003.

Polvere R.I., et al., GenBank Accession No. U88240, "*Tricinella Spiralis* Hypothetical ORF 2.20 mRNA", partial cds, Mar. 4, 1997.

R. B. Horsch et al., "A Simple and General Method for Transferring Genes into Plants", Science 227, Mar. 1985, pp. 1229-1231.

R. B. Horsch et al., Rapid Assay of Foreign Gene Expression in Leaf Discs Transformed by *Agrobacterium tumefaciens*: Role of T-DNA Borders in the Transfer Process, Proc. Natl. Acad. Sci. USA, Jun. 1986, vol. 83, pp. 4428-4432.

Richard A. Jefferson et al., GUS Fusions: Beta-glucuronidase as a Sensitive and Versatile Gene Fusion Marker in Higher Plants, The Embo Journal, IRL Press Limited, Dec. 20, 1987, vol. 6, No. 13, pp. 3901-3907.

Richard A. Jefferson, "Assaying Chimeric Genes in Plants: The GUS Gene Fusion System", Plant Molecular Biology Reporter, Plant Breeding Institute, 1987, vol. 5, No. 4, pp. 387-405.

Ringli et al., "Specific interaction of the tomato bZIP transcription factor VSF-1 with a non-palindromic DNA sequence that controls vascular gene expression," Plant Molecular Biology, vol. 37, 1998, pp. 977-988.

Robert T. Fraley et al., "Expression of Bacterial Genes in Plant Cells", Proc. Natl. Acad. Sci. USA, Monsanto Company, Aug. 1983, vol. 80, pp. 4803-4807.

Rogers et al., "Improved Vectors for Plant Transformation: Expression Cassette Vectors and New Selectable Markers," *Methods in Enzymology*, 1987, pp. 252-277, vol. 153, Academic Press, Inc.

S. G. Rogers et al., "Improved Vectors for Plant Transformation: Expression Cassette Vectors and New Selectable Markers", Methods in Enzymology, Recombinant DNA, Part D, Academic Press,1987, Inc., vol. 153, pp. 253-277.

S. L. Beaucage, et al., "Deoxynucleoside Phosphoramidites—A New Class of Key Intermediates for Deoxypolynucleotide Synthesis", Tetrahedron Letters, Pergamon Press Ltd., 1981, vol. 22, No. 20, pp. 1859-1862.

S.N.I.M. Salehuzzaman et al., "Isolation and Characterization of a cDNA Encoding Granule-Bound Starch Synthase in Cassava (*Manihot esculenta* Crantz) and its Antisense Expression in Potato", Plant Molecular Biology, Kluwer Academic Publishers, 1993, vol. 23, pp. 947-962.

Sambrook & Russel, "Molecular Cloning: a Laboratory Manual", 3$^{rd}$ Ed., Cold Spring Harbor Laboratory Press, Cold Spring Harbor, NY, (2001).

Schmidhauser et al., "Regions of Broad-Host-Range Plasmid RK2 Involved in Replication and Stable Maintenance in Nine Species of Gram-Negative Bacteria," *Journal of Bateriology*, Oct. 1985, pp. 446-455, vol. 164, No. 1, American Society for Microbiology.

Shabbir B. Bambot et al., "Efficient Total Gene Synthesis of 1.35-kb Hybrid Alpha-Lytic Protease Gene Using the Polymerase Chain Reaction", PCR Methods and Applications, Cold Spring Harbor Laboratory, Feb. 1993, vol. 2, No. 3, pp. 266-271.

Sibley et al., "The Phylogeny and Classification of the Passerine Birds, Based on Comparisons of the Genetic Material, DNA," *ACTA XVIII Congressus Internationalis Ornithologici*, Aug. 16-24, 1982, pp. 83-121, vol. 1.

Sonia Torres-Schumann et al., "In Vitro Binding of the Tomato bZIP Transcriptional Activator VSF-1 to a Regulatory Element that Controls Xylem-Specific Gene Expression", The Plant Journal, 1996, vol. 9, No. 3, pp. 283-296.

Stephen F. Altschul et al., "Basic Local Alignment Search Tool", J. Mol. Biol., Academic Press Limited, Oct. 5, 1990, vol. 215, No. 3, pp. 403-410.

Stephen F. Altschul et al., "Gapped BLAST and PSI-BLAST: A new generation of protein database search programs", Nucleic Acids Research, Oxford University Press, 1997, vol. 25, No. 17, pp. 3389-3402.

T. M. Klein et al., "Factors Influencing Gene Delivery into *ZEA Mays* Cells by High-Velocity Microprojectiles, Bio/Technology, "BioActive Compounds From Algae May 1988, vol. 6, pp. 559-563.

Tom I. Bonner et al., "Reduction in the Rate of DNA Reassociation by Sequence Divergence", Journal of Molecular Biology, Mar. 15, 1973, vol. 81, pp. 123-135.

Vimla Vasil et al., "Herbicide Resistant Fertile Transgenic Wheat Plants Obtained by Microprojectile Bombardment of Regenerable Embryogenic Callus", Bio/Technology, Jun. 1992, vol. 10, pp. 667-674.

Vimla Vasil et al., "Regeneration of Plants From Embryogenic Suspension Culture Protoplasts of Wheat (*Triticum Aestivum* L.)", Bio/Technology, May 1990, vol. 8, pp. 429-434.

Ziv Shani et al., "Cellulose Binding Domain Increases Cellulose Synthase Activity in *Acetobacter xylinum*, and Biomass of Transgenic Plants", Plant Biotechnology and in Vitro Biology in the 21$^{st}$ Century, Proceedings of the IXth International Congress of the International Association of Plant Tissue Culture and Biotechnology Jerusalem, Isreal, Jun. 14-19, 1998, Kluwer Academic Publishers, 1999, pp. 213-218.

\* cited by examiner

VASCULAR-PREFERRED PROMOTERS

CROSS-REFERENCE TO RELATED APPLICATION

This application is a Divisional of U.S. application Ser. No. 10/717,897 filed Nov. 21, 2003, which claims the benefit of U.S. Provisional Application No. 60/428,287, filed Nov. 22, 2002.

FIELD OF INVENTION

The present invention relates to the regulation of polynucleotide transcription and/or expression. In particular, this invention relates to polynucleotide regulatory sequences isolated from *Eucalyptus grandis* and *Pinus radiata* that confer vascular-preferred transcription of polynucleotides in plant cells. Constructs and methods for using the inventive regulatory sequences for modifying transcription of endogenous and/or heterologous polynucleotides also are included in the invention.

BACKGROUND OF THE INVENTION

A major goal in the forestry and paper industries is the control of lignin content in plants. Lignin is a complex polymer of cinnamyl alcohols that is responsible for wood's mechanical strength, coloration, and resistance to rot. Tree species synthesize large quantities of lignin, with lignin constituting between 20% to 30% of the dry weight of wood. In addition to providing rigidity, lignin aids water transport by rendering cell walls hydrophobic and water-impermeable. It follows that increasing the lignin concentration in trees can prove beneficial for certain applications, such as providing trees with improved disease resistance or increased strength for use in construction. Lignin is also useful as a fuel, and lignin together with increased cellulose content is desirable in wood or other biomass used as fuel, such as wood for charcoal production, corn stover, and trees such as willow and fast growing aspen hybrids used for biofuels.

Conversely, the high concentration of lignin in trees presents a significant problem for the paper industry, which must expend considerable resources to separate lignin from cellulose fiber. In the U.S. alone, about 20 million tons of lignin are removed from wood per year. Further, the content of lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. Lignin content increases during plant growth, so that farmers must choose between harvesting crops early to obtain a lower yield of more digestible crops or later to obtain a higher yield of less digestible material.

For these reasons, the control of lignin content or composition through genetic modification of plants is desirable. Considerable effort has been made to this end to identify and characterize the genes responsible for lignin biosynthesis and to determine sequences that regulate their expression. Polynucleotides encoding many of the enzymes involved in lignin biosynthesis have been cloned, including cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine. U.S. Pat. No. 6,204,434.

Manipulation of the expression of these genes has been used to modify lignin content. Such experiments include altering the number of copies of genes encoding CAD, coniferin β-glucosidase (CBG), and caffeic acid 3-O-methyltransferase (COMT). U.S. Pat. No. 5,451,514, WO 94/23044, and Dharmawardhana et al, *Plant Mol. Biol.* 40: 365-72 (1999). Furthermore, antisense expression of sequences encoding CAD in poplar, *N. tabacum*, and pine leads to the production of lignin having a modified composition. Grand et al., *Planta (Berl.)* 163: 232-37 (1985), Yahiaoui et al., *Phytochemistry* 49: 295-306 (1998), and Baucher et al., *Plant Physiol.* 112: 1479 (1996), respectively.

Another major goal of the forest products, paper, plant biomass and forage industries is to increase the size of the stem, to manipulate cellulose content in the stem, or to manipulate characteristics of the cell wall in order to facilitate the recovery of cellulose from the stem. For example, cellulose is recovered from the xylem fibers in pulp production, and the number of xylem fibers and vessel elements, thickness of the cell walls, diameter of the cell lumens, length of the fibers, cellulose microfibril angle and other characteristics of these xylem cells determine the quality and quantity of cellulose recovered. Manipulation of genes involved in cellulose biosynthesis has been useful to increase the total biomass of plants and the yield of cellulose from the plants, while antisense expression of such genes has demonstrated effects on cell wall development. Shani Z., Shpigel, E., Roiz, L., Goren, R., Vinocur, B., Tzfira, T., Altman, A., and Shoseyov O. Cellulose binding domain increases cellulose synthase activity in *Acetobacter xylinum*, and biomass of transgenic plants. In: A. Altman, M. Ziv, S. Tzhar, eds., Plant Biotechnology and In Vitro Biology in the 21st Century, pp. 213-218 Kluwer Academic Publishers. (1999). Modification of polysaccharides and plant cell wall by endo-1,4-β-glucanase and cellulose-binding domains has been described. Levy, I., Shani, Z. and Shoseyov O. Biomol Eng. 19: 17-30 (2002). Accordingly, the polynucleotides of the instant invention can be used to express nucleotide sequences in vascular tissue to modify cellulose biosysnthesis thereby affecting plant growth and biomass.

Genetic regulation of biochemical pathways preferably is conducted in narrowly restricted tissue types to avoid global, detrimental effects to the modified plants. For example, when the content or composition of lignin is affected by expression of a particular gene product, it may be desirable to limit the expression of the gene product to certain segments of the plant or to certain developmental stages, to avoid decreasing the plant's disease resistance. A heterologous gene may be expressed in a selected tissue by operably linking it to a tissue-preferred promoter. Suitable tissue-preferred promoters include the bean grp1.8 promoter, which is specifically active in protoxylem tracheary elements of vascular tissue. Keller et al., *EMBO J.* 8: 1309 (1989). These promoters also include the eucalyptus CAD promoter, which is preferentially expressed in lignifying zones. Feuillet et al., *Plant Mol. Biol.* 27: 651 (1995). Such tissue-preferred promoters have been used to regulate gene expression of antisense molecules in specific tissues. Van der Meer et al., *Plant Cell* 4: 253 (1992), Salehuzzaman et al., *Plant Mol. Biol.* 23: 947 (1993), and Matsuda et al., *Plant Cell Physiol.* 37: 215 (1996).

Because tissue-preferred promoters may be less active in a heterologous environment, they do not always express genes to the same levels achieved with constitutive promoters. Yahiaoui et al., *Phytochemistry* 49: 295-306 (1998). Further, the developmental window during which these promoters are active, or the spatial distribution of their activity, may limit their usefulness. Thus, there is a continuing need in the art to define additional tissue-preferred promoters, especially vascular-preferred promoters, that have desirable spatial and temporal patterns of expression. Reviewed by Grima-Pettenati et al., *Plant Science* 145: 51-65 (1999).

SUMMARY OF THE INVENTION

The present invention relates to isolated polynucleotide regulatory sequences that confer vascular-preferred gene expression. The polynucleotides of the present invention can be used for controlling the lignin content, cellulose content, size or cell wall development of a plant. The polynucleotides of the present invention may also be used for regulating biosynthesis of lignin, cellulose, and plant cell walls.

In one aspect, the present invention provides an isolated nucleic molecule comprising a polynucleotide that is capable of conferring vascular-preferred polynucleotide transcription. In one embodiment, the isolated nucleic molecule comprises a polynucleotide selected from any one of SEQ ID NO: 1-85 and functional variants thereof. In another embodiment, the functional variant has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NO: 1-85.

In another aspect, the present invention provides an isolated polynucleotide having a sequence selected from (a) sequences complementary to any one of SEQ ID NO: 1-85 and functional variants thereof, (b) sequences that are reverse complements to any of the sequences in SEQ ID NO: 1-85; and (c) sequences comprising at least 20 contiguous bases, which hybridizes to any of the polynucleotides of (a) or (b). In one embodiment, the present invention contemplates wherein said polynucleotide confers xylem-preferred gene expression in a plant cell. In another embodiment, the present invention provides a polynucleotide capable of upregulating or downregulating the expression of an operably-linked gene in a plant cell.

In another aspect, the present invention provides a plant cell comprising (a) at least one polynucleotide sequence that has the sequence of any one of SEQ ID NO: 1-85, and (b) a desired gene, wherein said polynucleotide and said desired gene are operably linked. In one embodiment, the desired gene encodes a polypeptide or protein. In another embodiment, the protein is an enzyme involved in the biosynthesis of cell walls. In a further embodiment, the protein is an enzyme involved in lignin biosynthesis. In another embodiment, the desired gene produces an RNA transcript. In yet another embodiment, the RNA transcript has an antisense sequence of a gene that is endogenous to a plant cell. In an further embodiment, the RNA transcript induces RNA interference of a gene that is normally expressed in a plant cell.

In another aspect, the present invention provides a plant comprising a plant cell having (a) at least one polynucleotide sequence that has the sequence of any one of SEQ ID NO: 1-85, and (b) a desired gene, wherein said polynucleotide and said desired gene are operably linked. In one embodiment, the plant is selected from angiosperms and gymnosperms.

In another embodiment, the present invention contemplates a method for regulating the lignin content of a plant, comprising cultivating the plant comprising a plant cell comprising a DNA construct that comprises (a) at least one polynucleotide sequence that has the sequence of any one of SEQ ID NO: 1-85, and (b) a desired gene, wherein said polynucleotide and said desired gene are operably linked.

In another aspect, the present invention contemplates a method for regulating cell wall development in a plant, comprising cultivating the plant comprising a plant cell comprising a DNA construct that comprises (a) at least one polynucleotide sequence that has the sequence of any one of SEQ ID NO: 1-85, and (b) a desired gene, wherein said polynucleotide and said desired gene are operably linked.

In another aspect, the present invention provides a transgenic plant comprising a polynucleotide sequence selected from any one of SEQ ID NO: 1-85 and functional variants thereof.

In one aspect, the present invention provides a method for obtaining wood, comprising (a) introducing into a plant cell of a woody plant a DNA construct comprising (i) a promoter having the sequence of any one of SEQ ID NOs: 1 to 85 or functional variants thereof and (ii) and a desired nucleic acid, wherein said promoter regulates the expression of said desired nucleic acid; (b) culturing said transformed plant cell under conditions that promote growth of a plant; and (c) obtaining wood from said plant. In one embodiment, the woody plant is selected from a species of *Eucalyptus* or *Pinus*.

The present invention also contemplates an isolated polynucleotide sequence selected from the group consisting of SEQ ID NO: 1-85, and polynuclucleotides having at least 60% sequence identity to any of these sequences. The invention also contemplates a polynucleotide having at least 65% sequence identity to any one of SEQ ID NO: 1-85. The invention further contemplates a polynucleotide having at least 70% sequence identity to any one of SEQ ID NO: 1-85. The present invention provides an isolated polynucleotide sequence having at least 75% sequence identity to any of SEQ ID NO: 1-85. The invention contemplates a polynucleotide having at least 80% sequence identity to any of SEQ ID NO: 1-85. Also provided is an isolated polynucleotide having 85% sequence identity to any one of SEQ ID NO: 1-85. The present invention contemplates sequences having at least 90% sequence identity to any one of SEQ ID NO: 1-85. Sequences having at least 95% sequence identity with any of SEQ ID NO: 1-85 are provided by the present invention.

DETAILED DESCRIPTION OF THE EMBODIMENTS

Figure 1:
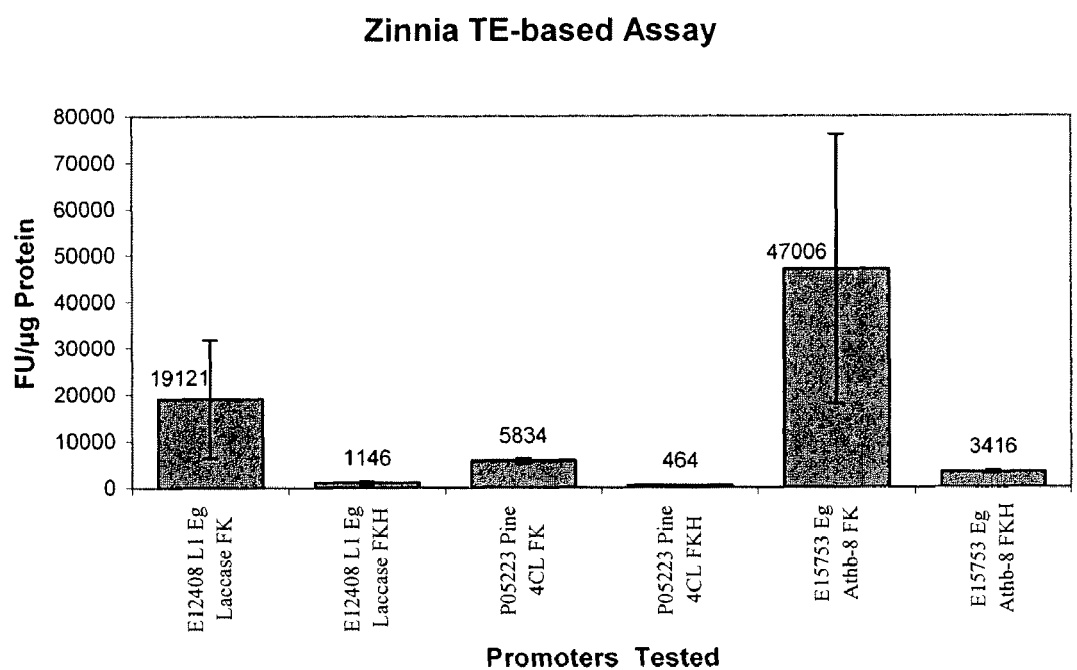
FIG. 1 depicts a *Zinnia* TE-based assay demonstrating three promoters having a similar expression profiles at Day 3 of culture.
Figure 2A:
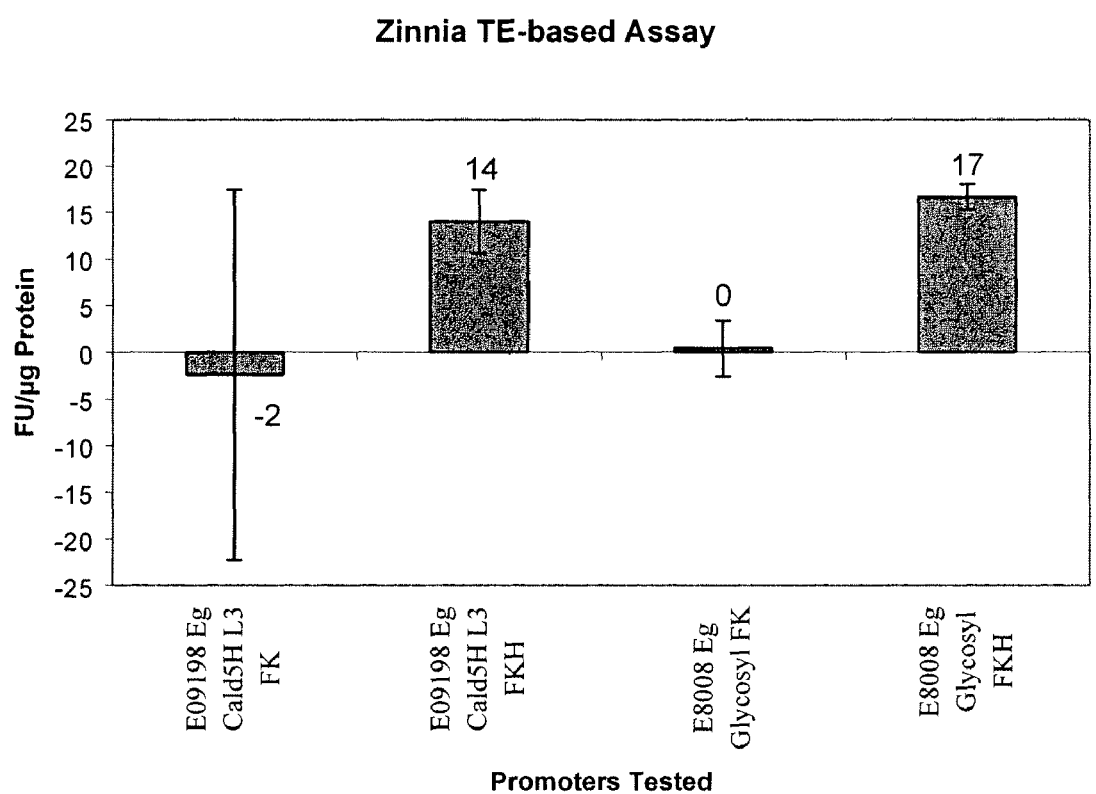
FIG. 2 depicts a *Zinnia* TE-based assay demonstrating two promoters having a similar expression profile at Day 3 of culture.
Figure 2B:
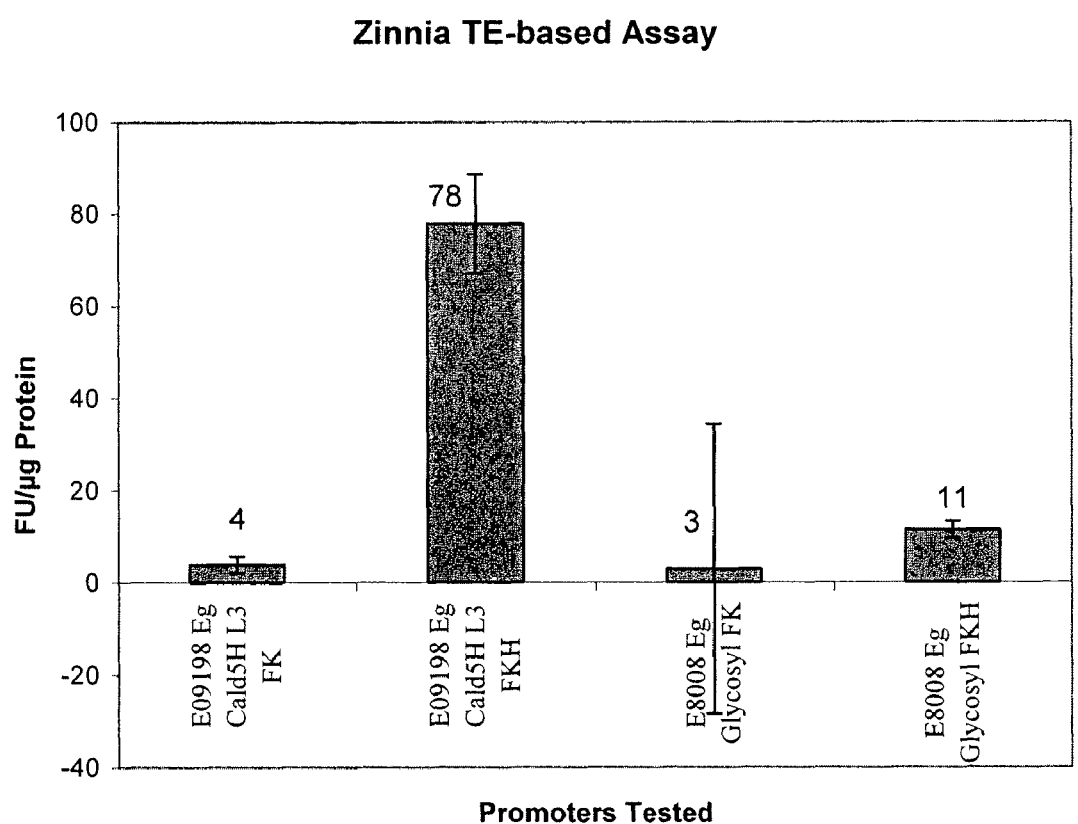
Figure 3:
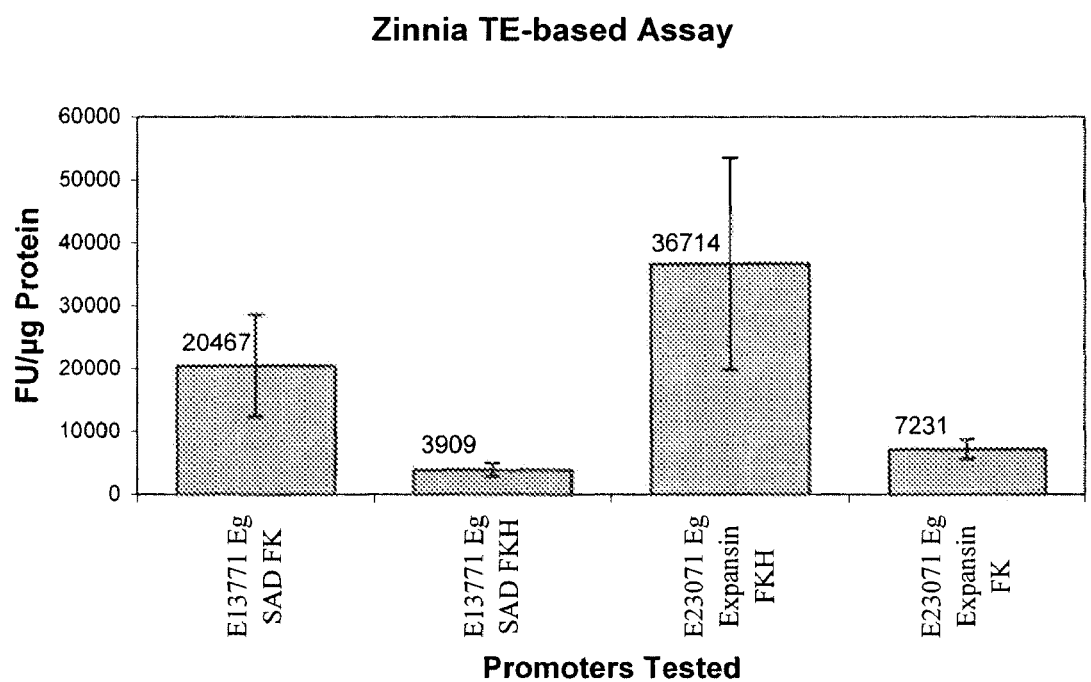
FIG. 3 depicts a *Zinnia* TE-based assay demonstrating two promoters having a similar expression profile at Day 3 of culture.

The present invention relates to an isolated nucleic molecule comprising a polynucleotide having a sequence at least 95% identical to a sequence selected from the group consisting of any of the polynucleotide sequences set forth in Table 6. The invention also provides functional fragments of the polynucleotide sequences disclosed in Table 6. The invention further provides complementary nucleic acids, or fragments thereof, to any of the polynucleotide sequences listed in Table 6, as well as a nucleic acid, comprising at least 15 contiguous bases, which hybridizes to any of the polynucleotide sequences disclosed in Table 6

The present invention relates to an isolated nucleic molecule comprising a polynucleotide having a sequence at least 95% identical to a sequence selected from the group consisting of any of the polynucleotide sequences set forth in Table 6. The invention also provides functional fragments of the polynucleotide sequences disclosed in Table 6. The invention further provides complementary nucleic acids, or fragments thereof, to any of the polynucleotide sequences listed in Table 6, as well as a nucleic acid, comprising at least 15 contiguous bases, which hybridizes to any of the polynucleotide sequences disclosed in Table 6.

The nucleotide sequences of the nucleic acids of the invention are provided in a sequence listing. What is intended by "SEQ ID NO: (2N+1)" are all the odd numbered sequences in the sequence listing, e.g., 1, 3, 5, 7 etc. What is intended by "SEQ ID NO: 2N" are the even numbered sequences. The difference between an odd numbered sequence, and the immediately proceeding even numbered sequence (e.g, SEQ ID NO: 1 and SEQ ID NO:2) should be that the even numbered sequence has additional bases. The last three bases of the even numbered sequences are usually ATG and represent the start codon (usually coding for methionine) for translation.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology. See, e.g., Sambrook & Russel, MOLECULAR CLONING: A LABORATORY MANUAL, 3$^{rd}$ ed., Cold Spring Harbor Laboratory Press, Cold Spring Harbor, N.Y., 2001.

*Agrobacterium*: as is well known in the field, *Agrobacteria* that are used for transforming plant cells are disarmed and virulent derivatives of, usually, *Agrobacterium tumefaciens* or *Agrobacterium rhizogenes* that contain a vector. The vector typically contains a desired polynucleotide that is located between the borders of a T-DNA.

Angiosperm: vascular plants having seeds enclosed in an ovary. Angiosperms are seed plants that produce flowers that bear fruits. Angiosperms are divided into dicotyledonous and monocotyledonous plants.

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'-orientation, a promoter, a gene that encodes a protein, and a terminator. Alternatively, the desired polynucleotide may comprise a gene or fragment thereof in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or may be a variant of its wild-type sequence. It is understood that all or part of the desired polynucleotide can be integrated into the genome of a plant. It also is understood that the term "desired polynucleotide" encompasses one or more of such polynucleotides. Thus, a T-DNA of the present invention may comprise one, two, three, four, five, six, seven, eight, nine, ten, or more desired polynucleotides.

Dicotyledonous plant (dicot): a flowering plant whose embryos have two seed halves or cotyledons, branching leaf veins, and flower parts in multiples of four or five. Examples of dicots include but are not limited to, *Eucalyptus, Populus, Liquidamber, Acacia*, teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

Endogenous refers to a gene that is native to a plant genome.

Fiber composition: as used herein, fiber composition refers to a trait that can be modified to change the structure, appearance, or use of fiber. Traits that determine fiber composition include but are not limited to fiber length, coarseness, strength, color, cross-sectional width, and fiber density. For example, it is known that fiber length imparts strength, whereas fiber coarseness is a determinant of texture and flexibility.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, or does not belong to the species of the target plant. According to the present invention, foreign DNA or RNA may include nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule, and includes both coding and non-coding sequences.

Genetic element: a "genetic element" is any discreet nucleotide sequence including, but not limited to, a promoter, a gene, a terminator, an intron, an enhancer, a spacer, a 5'-untranslated region, a 3'-untranslated region, or a recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperms include conifers, cycads, ginkgos, and ephedras.

Introduction: as used herein, refers to the insertion of a nucleic acid sequence into a cell, by methods including infection, transfection, transformation or transduction.

Juvenility: describes a physiological difference between a young tree and a mature tree. In the present invention, juvenility refers to differences in microfibril angle, wood density, cellulose yield, regenerability, and reproductive ability between a young tree and a mature tree. For example, it has been shown that as a woody plant tissue matures, the tissue loses its ability to regenerate.

Lignin: as used herein, refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of each of monolignols or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. The degradation of lignin from softwoods, such as pine, requires substantially more alkali and longer incubations, compared with the removal of lignin from hardwoods. Lignin composition may be regulated by either up-regulation or down-regulation of enzymes involved lignin biosynthesis. For example, key lignin biosynthsesis enzymes include, but are not limited to, 4-coumaric acid: coenzyme A ligase (4CL), Cinnamyl Alcohol dehydrogenase (CAD), and Sinapyl Alcohol Dehydrogenase (SAD).

Monocotyledonous plant (monocot): a flowering plant having embryos with one cotyledon or seed leaf, parallel leaf veins, and flower parts in multiples of three. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

Operably linked: combining two or more molecules in such a fashion that in combination they function properly in a plant cell. For instance, a promoter is operably linked to a structural gene when the promoter controls transcription of the structural gene.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a tranformed plant by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome may yield a phenotype selected from the group consisting of, for example, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, improved flower longevity, altered density, altered stem strength or stem stiffness, increased dimensional stability, and altered cellulose or lignin content.

Plant tissue: a "plant" is any of various photosynthetic, eukaryotic, multicellular organisms of the kingdom *Plantae* characteristically producing embryos, containing chloroplasts, and having cellulose cell walls. A part of a plant, i.e., a "plant tissue" may be transformed according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, apple, grape, pine, fir, acacia, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir and spruce, monocots such as Kentucky bluegrass, creeping bentgrass, maize, and wheat, and dicots such as cotton, tomato, lettuce, *Arabidopsis*, tobacco, apple and geranium.

Plant transformation and cell culture: broadly refers to the process by which plant cells are genetically modified and transferred to an appropriate plant culture medium for maintenance, further growth, and/or further development. Such methods are well known to the skilled artisan.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein also may be considered to be the offspring or descendants of a group of plants. A transgenic plant of the instant invention can be asexually reproduced to produce progeny plants.

Promoter: is intended to mean a nucleic acid, preferably DNA, that binds RNA polymerase and/or other transcription regulatory elements. As with any promoter, the promoter sequences of the current present invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity may determine whether the promoter activity is high or low, i.e. whether the promoter is "strong" or "weak."

A plant promoter is a promoter capable of initiating transcription in plant cells, whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as xylem, leaves, roots, or seeds. Such promoters are referred to as tissue preferred promoters. Promoters which initiate transcription only in certain tissues are referred to as tissue specific promoters. A cell type specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence comprising a gene coding sequence or a fragment thereof (comprising at least 15 consecutive nucleotides, at least 30 consecutive nucleotides, or at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature, or the polynucleotide is separated from nucleotide sequences to which it typically is in proximity, or is in proximity to nucleotide sequences with which it typically is not in proximity.

Regenerability: as used herein, refers to the ability of a plant to redifferentiate from a de-differentiated tissue.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. Examples of selectable markers include the neomycin phosphotransferase (NPTII) gene encoding kanamycin and geneticin resistance, the hygromycin phosphotransferase (HPT or APHIV) gene encoding resistance to hygromycin, acetolactate synthase (als) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region.

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Transcription factor: Transcription factor refers to a polypeptide sequence that regulates the expression of a gene or genes by either directly binding to one or more nucleotide sequences associated with a gene coding sequence or indirectly affecting the activity of another polypeptide(s) that bind directly to one or more nucleotide sequences associated with a gene coding sequence. A transcription factor may activate (up-regulate) or repress (down-regulate) expression of a gene or genes. A transcription factor may contain a DNA binding domain, an activation domain, or a domain for protein-protein interactions. In the present invention, a transcription factor is capable of at least one of (1) binding to a nucleic acid sequence or (2) regulating expression of a gene in a plant. Additionally, the inventive polynucleotide sequences and the corresponding polypeptide sequences function as transcription factors in any plant species, including angiosperms and gymnosperms.

Transcription and translation terminators: The expression DNA constructs of the present invention typically have a transcriptional termination region at the opposite end from the transcription initiation regulatory element. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that may comprise only one genetically modified cell and cell genome, or it may comprise several or many genetically modified cells, or all of the cells may be genetically modified. A transgenic plant of the present invention may be one in which expression of the desired polynucleotide, i.e., the exogenous nucleic acid, occurs in only certain parts of the plant. Thus, a transgenic plant may contain only genetically modified cells in certain parts of its structure.

Variant: a "variant," as used herein, is understood to mean a nucleotide sequence that deviates from the reference (i.e., native, standard, or given) nucleotide sequence of a particular gene. The terms, "isoform," "isotype," and "analog" also refer to "variant" forms of a nucleotide sequence.

"Variant" may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132,970, which is incorporated herein by reference.

Wood composition, as used herein, refers to a trait that can be modified to change the structure, appearance, or use of wood. While not limiting, traits that determine wood composition include cell wall thickness, cell length, cell size, lumen size, cell density, microfibril angle, tensile strength, tear strength, wood color, and length and frequency of cell division.

Wood pulp refers to fiber generated from wood having varying degrees of purification. Wood pulp can be used for producing paper, paper board, and chemical products.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules, according to the present invention, further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also referred to as the antisense strand.

Unless otherwise indicated, all nucleotide sequences determined by sequencing a DNA molecule herein were determined using an automated DNA sequencer (such as the Model 3700 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

The present invention is also directed to fragments of the isolated nucleic acid molecules described herein. By a fragment of an isolated DNA molecule having the nucleotide sequences shown in Table 6 is intended DNA fragments at least 15 nucleotides, at least 20 nucleotides, at least 30 nucleotides in length, which are useful as diagnostic probes and primers is discussed in more detail below. Of course larger nucleic acid fragments of up to the entire length of the nucleic acid molecules of the present invention are also useful diagnostically as probes, according to conventional hybridization techniques, or as primers for amplification of a target sequence by the polymerase chain reaction (PCR), as described, for instance, in Molecular Cloning, A Laboratory Manual, 3rd. edition, edited by Sambrook, J and Russel, D. W., (2001), Cold Spring Harbor Laboratory Press, Cold Spring Harbor, N.Y., the entire disclosure of which is hereby incorporated herein by reference.

By a fragment at least 20 nucleotides in length, for example, is intended fragments which include 20 or more contiguous bases from the nucleotide sequence of the as shown in Table 6. The nucleic acids containing the nucleotide sequences listed in Table 6 can be generated using conventional methods of DNA synthesis which will be routine to the skilled artisan. For example, restriction endonuclease cleavage or shearing by sonication could easily be used to generate fragments of various sizes. Alternatively, the DNA fragments of the present invention could be generated synthetically according to known techniques.

In another aspect, the invention provides an isolated nucleic acid molecule comprising a polynucleotide which hybridizes under stringent hybridization conditions to a portion of the polynucleotide in a nucleic acid molecule of the invention described above. By a polynucleotide which hybridizes to a "portion" of a polynucleotide is intended a polynucleotide (either DNA or RNA) hybridizing to at least about 15 nucleotides, at least about 20 nucleotides, at least about 30 nucleotides, and more than 30 nucleotides of the reference polynucleotide. These fragments that hybridize to the reference fragments are useful as diagnostic probes and primers. A probe, as used herein is defined as at least about 100 contiguous bases of one of the nucleic acids in Table 6. For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

As mentioned previously, the present application is directed to such nucleic acid molecules which are at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to a nucleic acid sequence described above. One embodiment encompasses nucleic acid molecules which are at least 95%, 96%, 97%, 98%, 99% or 100% identical to the nucleic acid sequence shown in Table 6. By a polynucleotide having a nucleotide sequence at least, for example, 95% "identical" to a reference nucleotide sequence, is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art. Although any sequence algorithm can be used to define sequence identity, for clarity, the present invention defines identity with reference to the Basis Local Alignment Search Tool (BLAST) algorithm (Altschul et al., *J. Mol. Biol.* 215:403-410 (1990)), where a promoter sequence set forth in the disclosure is used as the reference sequence to define the percentage identity of polynucleotide homologues over its length. The choice of parameter values for matches, mismatches, and inserts or deletions is arbitrary, although some parameter values have been found to yield more biologically realistic results than others.

When using BLAST or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Relatedness between two polynucleotides also may be described by reference to their ability to hybridize to form double-stranded complexes by the formation of complementary base pairs. Hybridization conditions have been described previously herein. An increase in temperature can be used to break apart these complexes. The more structurally identical two sequences are, the higher the temperature required to break them apart or "melt" them. The temperature required to melt a double-stranded complex is called the "$T_m$." The relationship between the $T_m$ and other hybridization parameters is given by:

$$T_m (° C.) = 81.5 + 16.6(\log_{10}[Na^+]) + 0.41(\text{fraction } G+C) - 0.63 (\% \text{ formamide}) - (600/l),$$

where $T_m$ is the melting temperature of a DNA duplex consisting of the probe and its target; and l=the length of the hybrid in base pairs, provided I>100 base pairs. Bolton et al., *Proc. Natl. Acad. Sci.* 48:1390 (1962). Generally, a change of 1° C. in the melting point represents from 0.7% to 3.2% difference in DNA sequence similarity. Bonner et al., *Journal of Molecular Biology* 81:123-35 (1973); McCarthy et al., In EVOLUTION OF GENETIC SYSTEMS, H. H. Smith (ed.), Brookhaven Symposium in Biology No. 23, Gordon and Breach, New York, pp. 1-43 (1972). The formation of a stable DNA duplex at 60° C. typically requires at least an 80% sequence identity between sequences. Sibley et al., *ACTA* 1: 83-121 (Proceedings of the 18th International Ornithological Congress, Moscow, Aug. 16-24, 1982, Academy of Sciences of the USSR).

The nucleic acids of the present invention confer preferential expression of polypeptides or proteins in the vascular tissue of plants. The nucleic acids of the present invention can also preferentially direct the expression of antisense RNA, or RNA involved in RNA interference (RNAi) such as small interfering RNA (siRNA), in the vascular tissue of plants, which can be useful for inhibiting or completely blocking the expression of targeted genes.

As used herein, vascular plant tissue refers to xylem, phloem or vascular cambium tissue. In one embodiment, the promoters of the invention are either "xylem-specific", "cambium-specific" and/or "phloem-specific" and direct expression of an operably linked nucleic acid segment in the xylem, cambium and/or phloem, respectively. As used herein, "coding product" is intended to mean the ultimate product of the nucleic acid that is operably linked to the promoters. For example, a protein or polypeptide is a coding product, as well as antisense RNA or siRNA which is the ultimate product of the nucleic acid coding for the antisense RNA. The coding product may also be non-translated mRNA. The terms polypeptide and protein are used interchangeably herein. Xylem-specific, for example, is intended to mean that the nucleic acid molecules of the current invention are more active in the xylem than in any other plant tissue. In one embodiment, the nucleic acids of the current invention are promoters that are active specifically in the xylem, cambium and/or phloem, meaning that the promoters are only active in the xylem, cambium, and/or phloem tissue of plants, respectively. In other words, a "xylem-specific" promoter, for example, drives the expression of a coding product such that detectable levels of the coding product are expressed only in xylem tissue of a plant. However, because of solute transport in plants, the coding product that is specifically expressed in the xylem, phloem or cambium may be found anywhere in the plant and thus its presence is not necessarily confined to xylem tissue. A vascular-preferred promoter, on the other hand can be preferentially active is any of the xylem, phloem or cambium tissues, or in at least two of the three tissue types. A vascular-specific promoter, is specifically active in any of the xylem, phloem or cambium, or in at least two of the three tissue types.

The vascular system, as used herein, comprises the xylem and phloem tissues that are used to conduct water and photosynthates in higher plants and the vascular cambium that is positioned between the xylem and phloem. As components of the vascular system, xylem and phloem are collectively referred to as vascular tissue. Vascular tissue is produced during two developmentally distinct stages. During embryogenesis and/or the post-embryogenic stage, primary vascular tissue develops from the differentiation of the apical meristem and the procambium. Secondary vascular tissue develops from the differentiation of the vascular cambium The vascular cambium is the lateral meristem positioned between the xylem and phloem and differentiates to produce secondary vascular tissue. The vascular cambium is composed of two cell types, fusiform and ray initials, which are collectively referred to as cambial initials. The division of fusiform initials results in the longitudinal or axial systems of the xylem and phloem, whereas the division of ray initials leads to the development of the transverse or ray systems. The cambial initials divide about a tangential axis, such that the xylem cells aggregate towards the interior of the axis and the phloem cells towards the periphery.

As used herein, xylem refers to the conducting tissue that transports water and mineral ions from the root system to aerial portions of the plant. Both primary and secondary xylem tissue comprises three distinct cell types, the tracheary elements, fibers, and parenchyma cells. The tracheary elements, comprising imperforate tracheids and perforate vessel elements, function in water conduction. Xylem fibers, comprising fiber tracheids and libriform fibers, impart strength and rigidity to the xylem structure. Parenchyma cells are comprised of axial and ray parenchyma cells, which are important for the storage of starch, oil, and other energy-rich molecules. Thus, a xylem-specific promoter, as contemplated in the current invention, is active in the tracheary elements, fibers, and/or parenchyma cells of the primary and/or secondary xylem.

Phloem is the plant tissue that translocates the products of photosynthesis from mature leaves to areas of growth and storage. The principal cells comprising both primary and secondary phloem tissue include sieve elements, parenchyma cells, and fibers. The sieve elements refer to the conducting elements of the phloem and are further comprised of sieve cells in gymnosperms or sieve-tube elements present in angiosperms. Sieve-tube elements form specialized structures called sieve tubes, wherein the sieve tube is comprised of a series of sieve-tube elements that are vertically arranged and interconnect through a portion of the cell wall referred to as the sieve plate. In contrast, the less specialized sieve cells, present in gymnosperms and lower vascular plants, do not interconnect to form sieve plates. Sieve cells are arranged in overlapping arrays such that conduction is facilitated through enlarged pores, called sieve areas. The sieve elements are associated with, and depend upon, specialized parenchyma cells called companion cells in angiosperms and albuminous cells in gymnosperms. Both companion and albuminous cells provide storage for proteins and metabolites necessary for sieve element function. In addition to the specialized parenchyma cells, the phloem contains parenchyma cells that function in the accumulation and storage of starch, fat, and other compounds. Phloem fibers impart strength to the phloem structure and may contribute to starch storage. Thus, a phloem-specific promoter, as contemplated in the present invention, is active in the sieve elements, parenchyma cells, and/or fibers of the primary and/or secondary phloem.

In most higher plants, the vascular tissues appear as a cylinder positioned between ground tissue. In both the stem and root, the pith and cortex comprise the ground tissue. The pith is located in the interior of vascular cylinder, whereas the cortex is located between the epidermis and the vascular tissue. Collectively, the vascular system and associated ground tissues are termed the vascular cylinder.

As used herein, promoter is intended to mean a nucleic acid, preferably DNA, that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule. As used herein, "operably linked" is meant to refer to the chemical fusion, ligation, or synthesis of DNA such that a promoter-nucleic acid sequence combination is formed in a proper orientation for the nucleic acid sequence to be transcribed into an RNA segment. The promoters of the current invention may also contain some or all of the 5' untranslated region (5' UTR) of the resulting mRNA transcript. On the other hand, the promoters of the current invention do not necessarily need to possess any of the 5' UTR.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The integrated effect of transcription factors on promoter activity may determine whether the promoter activity is high or low, i.e. whether the promoter is "strong" or "weak." Transcription factors that bind regulatory elements may themselves be regulated by the interaction with other bound proteins or by covalent modification, e.g. phosphorylation, in response to extracellular stimuli. The activity of some transcription factors is modulated by signaling molecules, such as intracellular metabolites or chemicals exogenous to the organism that communicate with the cellular nucleus. Promoters that are unaffected by changes in the cellular environment are referred to as constitutive promoters.

The present invention also provides vectors comprising the isolated nucleic acid molecules of the invention. In one embodiment, the vectors of the present invention are Ti-plasmids derived from the A. tumefaciens.

In developing the nucleic acid constructs of this invention, the various components of the construct or fragments thereof will normally be inserted into a convenient cloning vector, e.g., a plasmid that is capable of replication in a bacterial host, e.g., E. coli. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such markers include, but are not limited to, a neomycin phosphotransferase (nptII) gene (Potrykus et al. (1985), Mol. Gen. Genet. 199:183-188), which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., Bio/Technology 6:915-922 (1988)), which confers glyphosate resistance; a nitrilase gene, which confers resistance to bromoxynil (Stalker et al. (1988) J. Biol. Chem. 263:6310-6314); a mutant acetolactate synthase gene (ALS), which confers imidazolinone or sulphonylurea resistance (European Patent Application 154,204, 1985); and a methotrexate resistant DHFR gene (Thillet et al. (1988) J. Biol. Chem. 263:12500-12508).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

The vectors will preferably contain selectable markers. Numerous selectable markers for use in selecting transfected plant cells including, but not limited to, kanamycin, glyphosate resistance genes, and tetracycline or ampicillin resistance for culturing in E. coli, A. tumefaciens and other bacteria.

A plasmid vector suitable for the introduction of nucleic acid of the current invention into monocots using microprojectile bombardment is composed of the following: the promoter of choice; an intron that provides a splice site to facilitate expression of the gene, such as the Hsp70 intron (PCT Publication WO 93/19189); and a 3' polyadenylation sequence such as the nopaline synthase 3' sequence (NOS 3'; Fraley et al. (1983) Proc Natl Acad Sci USA 80: 4803-4807). This expression cassette may be assembled on high copy replicons suitable for the production of large quantities of DNA.

A particularly useful Agrobacterium-based plant transformation vector for use in transformation of dicotyledonous plants is plasmid vector pMON530 (Rogers et al. (1987) Improved vectors for plant transformation: expression cassette vectors and new selectable markers. In Methods in Enzymology. Edited by R. Wu and L. Grossman. p 253-277. San Diego: Academic Press). Plasmid pMON530 is a derivative of pMON505 prepared by transferring the 2.3 kb StuI-HindIII fragment of pMON316 (Rogers et al. (1987) Improved vectors for plant transformation: expression cassette vectors and new selectable markers. In Methods in Enzymology. Edited by R. Wu and L. Grossman. p 253-277. San Diego: Academic Press) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers et al., 1987) in which the Ti plasmid homology region, LIH, has been replaced with a 3.8 kb HindIII to SmaI segment of the mini RK2 plasmid, pTJS75 (Schmidhauser and Helinski. (1985) J. Bacteriol. 164-155). This segment contains the RK2 origin of replication, oriV, and the origin of transfer, oriT, for conjugation into Agrobacterium using the tri-parental mating procedure (Horsch and Klee. (1986) Proc. Natl. Acad. Sci. U.S.A. 83:4428-4432). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in E. coli and A. tumefaciens, an intact nopaline synthase gene for facile scoring of transformants and inheritance in progeny, and a pBR322 origin of replication for ease in making large amounts of the vector in E. coli. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the Arabidopsis EPSPS chloroplast transit peptide (CTP2), and expression is driven by the promoter of choice.

For secretion of the translated protein into the lumen of the endoplasmic reticulum, the periplasmic space or into the extracellular environment, appropriate secretion signals may be incorporated into the expressed polypeptide. The signals may be endogenous to the polypeptide or they may be heterologous signals.

In one embodiment, the vectors of the current invention are designed in a manner such that the nucleic acids described herein are tissue-specific promoters which are operably linked to DNA encoding a polypeptide of interest. In another embodiment, the polypeptide of interest is an enzyme involved in lignin biosynthesis in plants. Polynucleotides encoding many of the enzymes involved in lignin biosynthesis include, but are not limited to, cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine. U.S. Pat. No. 6,204,434. Other enzymes include coniferin β-glucosidase (CBG), and caffeic acid 3-O-methyltransferase (COMT). U.S. Pat. No. 5,451,514, WO 94/23044, and Dharmawardhana et al., *Plant Mol. Biol.* 40: 365-72 (1999).

In another embodiment, the coding sequence operably linked to the promoter may code for a gene product that inhibits the expression or activity of enzymes involved in lignin biosynthesis. For example, of particular interest for control of lignin biosynthesis is an antisense gene for cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine.

In a further embodiment, the vectors of the current invention are designed such that the nucleic acids of the current invention are operably linked to DNA or RNA that encodes antisense RNA or interfering RNA, which corresponds to genes that code for polypeptides of interest, resulting in a decreased expression of targeted gene products. Preferably the gene products targeted for suppression are enzymes involved in lignin biosynthesis, as discussed previously. The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

The use of antisense technology to reduce or inhibit the expression of specific plant genes has been described, for example in European Patent Publication No. 271988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening (Smith et. al., Nature, 334:724-726 (1988); Smith et. al., Plant Mol. Biol., 14:369-379 (1990)). Thus, antisense RNA has been demonstrated to be useful in achieving reduction of gene expression in plants.

In one embodiment of the method of making a plant of the invention, an exogenous DNA capable of being transcribed inside a plant to yield an antisense RNA transcript is introduced into the plant, e.g., into a plant cell. The exogenous DNA can be prepared, for example, by reversing the orientation of a gene sequence with respect to its promoter. Transcription of the exogenous DNA in the plant cell generates an intracellular RNA transcript that is "antisense" with respect to that gene.

For example, antisense technology may be used to suppress the expression of gene encoding enzymes involved in lignin biosynthesis, such as 4CL. A construct containing an antisense 4CL DNA sequence can be prepared by reversing the orientation of an exogenous DNA sequence encoding 4CL and operably linking the sequence to a promoter. Transcription of the exogenous 4CL DNA sequence in the plant cell would generate a 4CL RNA transcript that is in the antisense orientation.

The invention also provides host cells which comprise the vectors of the current invention. As used herein, a host cell refers to the cell in which the coding product is ultimately expressed. Accordingly, a host cell can be an individual cell, a cell culture or cells as part of an organism. The host cell can also be a portion of an embryo, endosperm, sperm or egg cell, or a fertilized egg.

The polynucleotides or vectors containing the polynucleotides of the current invention are introduced into the host cells by standard procedures known in the art for introducing recombinant vector DNA into the target host cell. Such procedures include, but are not limited to, transfection, infection, transformation, natural uptake, electroporation, biolistics and *Agrobacterium*. Methods for introducing foreign genes into plants are known in the art and can be used to insert a gene construct of the invention into a plant host, including, biological and physical plant transformation protocols. See, for example, Miki et al., 1993, "Procedure for Introducing Foreign DNA Into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., Science 227:1229-31, 1985), electroporation, micro-injection, and biolistic bombardment.

Accordingly, the present invention also provides plants or plant cells, comprising the polynucleotides or vectors comprising the polynucleotides of the current invention. In one embodiment, the plants are angiosperms or gymnosperms. In another embodiment, the plants are selected from *Eucalyptus* and *Pinus* species. In particular, the transgenic plant may be of the species *Eucalyptus* grandis and hybrids, *Pinus radiata*, *Pinus taeda* L (loblolly pine), *Populus nigra, Populus deltoides*, or *Liquidamber styraciflua*. Beyond the ordinary meaning of plant, the term "plants" is also intended to mean the fruit, seeds, flower, strobilus etc. of the plant. The plant of the current invention may be a direct transfectant, meaning that the vector was introduced directly into the plant, such as through *Agrobacterium*, or the plant may be the progeny of a transfected plant. The progeny may also be obtained by asexual reproduction of a transfected plant. The second or subsequent generation plant may or may not be produced by sexual reproduction, i.e., fertilization. Furthermore, the plant can be a gametophyte (haploid stage) or a sporophyte (diploid stage).

The present invention also provides a method of controlling the lignin content of a plant comprising cultivating a plant or seed comprising the vectors of the current invention. Proper cultivation to induce or sustain the growth or germination of the plants or seeds of the current invention is species-specific, and within the level of ordinary skill in the art. The setting for cultivation may be anywhere which fosters the growth or germination of the plant or seed. Furthermore, cultivation can also include steps such as, but not limited to, providing a stress treatment, (e.g., nitrogen deprivation, heat shock, low temperatures, sucrose deprivation) which can induce embryogenesis in anthers and/or microspores.

The invention further provides isolated regulatory elements that bind transcription factors and are capable of regulating tissue-preferred or tissue-specific expression. The degree of regulation conferred by the regulatory elements may be complete, meaning that transcription is not detectable without the transcription factors, or partial, meaning that transcription is enhanced in the presence of the transcription factors. In one embodiment, at least one regulatory element is operably linked to a heterologous promoter to provide a composite promoter. The composite promoter is expressed preferentially or specifically in vascular tissue. As used herein, heterologous promoters is a phrase whose meaning term that is relative to the regulatory elements. If a regulatory element and a promoter do not associate with one another in a natural setting, the promoter would be considered heterologous to the regulatory element. Typically, the precise orientation of a regulatory element within a promoter region will not affect its activity. Furthermore, regulatory elements can function normally when inserted into heterologous promoter regions. Thus, for example, xylem-preferred regulatory elements can be removed from their endogenous promoter and can be inserted into heterologous promoter regions to confer xylem-specificity or preference. Likewise, phloem-preferred regulatory elements can be removed from their endogenous promoter and can be inserted into heterologous promoter regions to confer phloem-specificity or preference. Similarly, cambium-preferred regulatory elements can be removed from their endogenous promoter and can be inserted into heterologous promoter regions to confer cambium-specificity or preference. The heterologous promoter may be, for example, a minimal CaMV 35S promoter. Promoters that direct expression in plant cells which are suitable for modification to minimal promoters include the cauliflower virus (CaMV) 35S promoter (Jefferson et al., *EMBO J.*, 6: 3901-07 (1987)), the rice actin promoter (McElroy et al., *Plant Cell*, 2: 163-71 (1990)), the maize ubiquitin-1 promoter (Christensen et al., *Transgenic Research*, 5: 213-18 (1996)), and the nopaline synthase promoter (Kononowics et al., *Plant Cell* 4: 17-27 (1992)).

To prepare the nucleic acids of the invention, genomic libraries were made from *Pinus radiata* and *Eucalyptus grandis*, using a variety of restriction endonucleases to digest the genome into discrete fragments. Genomic libraries can be similarly constructed from any plant species from which it is desirable to obtain tissue-selective promoters. An adaptor was ligated to each of these genomic sequences, according to the procedure provided by Clontech for use of its GenomeWalker™ Systems (Clontech, Palo Alto, Calif.). Promoter sequences then were PCR-amplified using adaptor-specific primers and "gene-specific primers." Alternatively, this PCR amplification step optionally may be conducted by the methodology described in U.S. Pat. No. 5,565,340 and No. 5,759, 822, herein incorporated by reference, to yield reaction products of long length and minimal background. Using this general PCR amplification methodology, the identification of the promoter of the invention and its identification as a tissue-selective promoter, is governed by the choice of the "gene-specific primer."

A gene-specific primer is any transcribed sequence that is expressed at high levels in a tissue of interest. In the present invention, the gene-specific primer is a fragment of, or is complementary to, an mRNA that is expressed at high levels in vascular tissue. In one embodiment, the gene-specific primer is selected by its homology to genes that are known to be expressed specifically in a particular vascular tissue type. Genes of particular interest are those that are expressed in a particular vascular tissue at high levels, which typically is an indicator of vascular-selective activity of the corresponding promoter.

Expressed sequence tags (ESTs) provide another source of gene-specific primers. An EST is a cDNA fragment of a corresponding mRNA that is present in a given library. Any plant EST database may be searched electronically to find ESTs that share identity to segments of genes that are known to be expressed specifically in a desired tissue type ("in silico screening"). These ESTs thus will provide gene-specific primers for the amplification of the promoter of the corresponding gene in a given genomic library. The amplified gene promoter need not be from the same species from which the EST database was obtained. All that is required is that the EST bears sufficient sequence similarity to the gene promoter of interest to act as a primer for PCR amplification of the target segment of the gene.

An alternative methodology to identify tissue-specific promoters rests on detection of mRNAs that are expressed in one tissue type, but not in another, implying that they are transcribed from a tissue-specific promoter. Populations of mRNAs can be distinguished on this basis by subtractive hybridization, for example. One such suitable subtractive hybridization technique is the PCR-Select™ described by Clontech.

Alternatively, a tissue-specific mRNA distribution can be determined by in situ hybridization of thin slices of plant tissue with radiolabeled probes. Probes that radioactively stain a particular tissue type are then used to detect the promoter associated with the mRNA by Southern analysis of genomic libraries, using the methodologies described below. All of the aforementioned techniques require the preparation of mRNA libraries from the tissue of interest, in this case vascular tissue. The preparation of cDNA libraries from xylem tissue, for example, is described in Dharmawardhana et al., *Plant Mol. Biol.* 40: 365-72 (1999) or Loopstra et al., *Plant Mol. Biol.* 27: 277-91 (1995). Briefly, actively differentiating xylem is first stripped from felled trees. Total RNA is isolated using standard techniques, and poly(A) RNA then is isolated and reverse transcribed to construct a xylem-tissue cDNA library. As described in Dharmawardhana (1999), for example, the cDNA library was constructed in the λZAP-XR vector, employing Strategene cDNA synthesis and GigapakII Gold™ packaging kits. Xylem-specific promoters can, in turn, be isolated from such cDNA libraries by PCR using a gene-specific probe and a primer that recognizes a sequence at the 5' end of the promoter. A gene-specific probe can be obtained by the in silico approach described above, or by designing a specific probe based on the sequence of the mRNA, if known. Furthermore, a primer can be synthesized which is complementary to the 5' UTR of the desired target gene. Alternatively, the primer can be designed from a partial amino acid sequence of the encoded protein, as a so-called degenerate primer. (See Dharmawardhana (1999)).

Following isolation of the promoter of interest, various methods can be used to characterize its tissue-specific expression pattern and promoter strength. One commonly employed method is to operably link the promoter to a readily assayed reporter gene. For example, the xylem-preferred promoter and 5' UTR of the *Eucalyptus gunnii* cinnamoyl-CoA reductase (EgCCR) gene (position −1448 to +200, where +1 is the transcription start site) has been operably linked to the gene encoding β-glucuronidase (GUS). Lacombe et al., *Plant J.* 23: 663-76 (2000). Suitable expression constructs can be made using well-known methodologies.

Transformation of plants can be accomplished by any one of many suitable techniques, including *Agrobacterium*-mediated transformation, as described in U.S. Pat. No. 6,051, 757. Other methods for transforming trees are known in the art, as exemplified by U.S. Pat. No. 6,518,485, which discloses an accelerated particle transformation method of gymnosperm somatic embryos. Other transformation methods include micro-projectile bombardment (Klein et al., *Biotechnology* 6: 559-63 (1988)), electroporation (Dhalluin et al.,

*Plant Cell* 4: 1495-1505 (1992)), and polyethylene glycol treatment (Golovkin et al., *Plant Sci.* 90: 41-52 (1993)). Further, U.S. Pat. No. 6,187,994 provides for a recombinase-assisted insertion of the expression construct into a specific, selected site within a plant genome. All of the aforementioned patents and publications are herein incorporated by reference.

A DNA molecule of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella et al. (1983) *Nature* 303:209, Bevan (1984) *Nucleic Acids Res.* 12 (22): 8711-8721, Klee et al. (1985) *Bio/Technology* 3(7): 637-642 and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome (Daniell et al. (1998) *Nature Biotechnology* 16:345-348).

When adequate numbers of cells (or protoplasts) containing the nucleic acid of interest are obtained, the cells (or protoplasts) are regenerated into whole plants. Choice of methodology for the regeneration step is not critical, with suitable protocols being available for hosts from *Leguminosae* (alfalfa, soybean, clover, etc.), *Umbelliferae* (carrot, celery, parsnip), *Cruciferae* (cabbage, radish, canola/rapeseed, etc.), *Cucurbitaceae* (melons and cucumber), *Gramineae* (wheat, barley, rice, maize, etc.), *Solanaceae* (potato, tobacco, tomato, peppers), various floral crops, such as sunflower, and nut-bearing trees, such as almonds, cashews, walnuts, and pecans. See, e.g., Ammirato et al. (1984) Handbook of Plant Cell Culture-Crop Species. Macmillan Publ. Co.; Fromm, M., (1990) UCLA Symposium on Molecular Strategies for Crop Improvement, Apr. 16-22, 1990. Keystone, Colo.; Vasil et al. (1990) *Bio/Technology* 8:429-434; Vasil et al. (1992) *Bio/Technology* 10:667-674; Hayashimoto et al. (1990) *Plant Physiol.* 93:857-863; and Datta et al. (1990).

The vector comprising the promoter and reporter gene includes a mechanism to select those plant cells successfully transformed with the vector, which may be, for example, kanamycin resistant. The presence of the GUS gene in transformants may be confirmed by a PCR approach, using GUS-specific PCR primers (Clontech, Palo Alto). Segregation of kanamycin resistance in the progeny of the transformed plant cells can be used in conjunction with Southern analysis to determine the number of loci harboring the stably inserted vector. The temporal and spatial pattern of promoter expression is then inferred from a quantification of the reporter gene expression, as described in Jefferson et al., *EMBO J.* 6: 3901-07 (1987). Generally, GUS expression is determined histochemically in thin slices of plant tissues that are fixed first in 90% acetone and then in a buffered solution containing a GUS substrate, 5-bromo-4-chloro-3-indoyl-β-D-glucuronic acid (X-Gluc). The presence of the GUS expression product is indicated by a calorimetric reaction with the X-Gluc.

Xylem-specific expression, for example, can be conferred by the presence of regulatory elements that specifically bind transcription factors in xylem tissue. The interaction between transcription factors that influence the degree of xylem specific expression depends on the alignment between a subset of base pairs of the regulatory element with amino acid residues of the transcription factor. Likewise, phloem-specific or cambium-specific expression, for example, can be conferred by the presence of regulatory elements that specifically bind transcription factors in phloem and cambium tissue, respectively. Base pairs that do not interact with the bound transcription factor may be substituted with other base pairs, while maintaining the overall ability of the regulatory element to bind specifically the tissue-specific transcription factor.

Various methodologies can be used to identify and characterize regulatory elements that affect tissue-preferred or tissue-specific promoter activity, once a promoter is identified as tissue-preferred or specific. In one methodology, the promoter region is sequentially truncated at the 5' end and the series of truncated promoters are each operably linked to a reporter gene. When a regulatory element is deleted, the effect on the promoter activity is inferred by the loss of tissue-specific expression of the reporter gene. Alternatively, a putative regulatory element can be inserted into an expression construct containing a minimal promoter, such as the CaMV 35S minimal promoter (Keller et al., *Plant Mol. Biol.* 26: 747-56) to ascertain if the putative regulatory element confers tissue-specific expression. A minimal promoter contains only those elements absolutely required for promoter activity, such as a RNA polymerase binding site. Additional examples for elucidating putative regulatory elements are provided by studies of tissue-specific regulatory elements that coordinately regulate transcription of the genes encoding L-phenyl-alanine ammonia-lyase (PAL) and 4-coumarate CoA ligase (4CL). Hatton et al., *Plant J.* 7: 859-76 (1995); Leyva et al., *Plant Cell* 4: 263-71 (1992); Hauffe et al., *Plant J.* 4: 235-53 (1993); Neustaedter et al., *Plant J.* 18: 77-88 (1999), all of which are incorporated herein by reference.

Another methodology to locate putative regulatory elements is to compare sequences among known vascular-preferred or vascular-specific regulatory elements. Nucleotide comparison will identify regions similar to known tissue-preferred regulatory elements, such as, for example, vascular-preferred regulatory elements. For example, comparison of promoter sequences between cinnamyl CoA reductase and other promoters involved in phenyl-propanoid production reveals a conserved AC-rich region having the sequence CCCACCTACC. See Lacombe (2000). Conservation of the above-noted sequence in promoters involved in phenylpropanoid synthesis implies that the conserved sequence is a binding site for a coordinately activating transcription factor, such as MYB, which has been identified in several plant species. See Martin, *Trends Genet.* 13: 67-73 (1997). For example, MYB binding sites have been identified in maize ([C/A]TCC[T/A]ACC) and Petunia (TAAC[C/G]GTT or TAACTAAC). Id.

Sequence comparisons of this sort, based on the nucleic acid sequences of the invention, reveal a series of motifs shown in Table 1, below. It is expected that the motifs in Table 1 bind tissue-preferred or tissue-specific transcription factors and can be used to modulate tissue-preferred or tissue-specific expression of a heterologous, minimal promoter.

TABLE 1

| SEQ ID NO: | MOTIF | PROMOTER |
|---|---|---|
| SEQ ID NO: 72 | AATCAAATCCTCC | Eucalyptus Microtubule assoc (SEQ ID NO 5) |
| SEQ ID NO: 73 | AATCAAATCCTCC | Eucalyptus F5H (SEQ ID NO 7) |
| SEQ ID NO: 74 | TCTCCCTCCTCT | Eucalyptus cellulose synthase (SEQ ID NO 8) |

TABLE 1-continued

| SEQ ID NO: | MOTIF | PROMOTER |
|---|---|---|
| SEQ ID NO: 75 | ATAAAGAAGTGAA | Eucalyptus cellulose synthase (SEQ ID NO 8) |
| SEQ ID NO: 76 | TAAACTTATTTTCT | Pine LIM (SEQ ID NO 9) |
| SEQ ID NO: 77 | TAAACTTATTTTCT | Pine Pectate Lyase (SEQ ID NO 10) |
| SEQ ID NO: 78 | GGAGAAACAAAA | Pine Pectate Lyase (SEQ ID NO 10) |
| SEQ ID NO: 79 | AAGTAACCAATGATGC | Pine Expansin (SEQ ID NO 11) |
| SEQ ID NO: 80 | ACTTTGAAGAAAA | Pine Expansin (SEQ ID NO 11) |
| SEQ ID NO: 81 | TGAGGAGAAGA | Pine 4CL3 (SEQ ID NO 13) |
| SEQ ID NO: 82 | ATCAAGCTGAT | Pine 4CL (SEQ ID NO 13) |
| SEQ ID NO: 83 | AATTTCATTTTC | Pine dirigent (SEQ ID NO 16) |
| SEQ ID NO: 84 | TAAATTTGAATTT | Eucalyptus Laccase (SEQ ID NO 17) |

The interaction of bZIP proteins with vascular-specific or vascular-preferred promoters, for example, provides another example of how one of skill in the art can characterize regulatory elements. For example, the gene encoding glycine-rich protein, grp1.8, is expressed in a xylem-specific manner, as determined by histochemical staining of a GRP1.8-β-glucuronidase fusion protein. Keller et al., *EMBO J.* 8: 1309-14 (1989). A 5' deletion study of the grp1.8 promoter revealed a 20-base pair negative regulatory element that is essential for vascular-specific expression. Keller et al., *Plant Cell* 3: 1051-61. Similar xylem-specific regulatory elements that operate by negative tissue-specific regulation of a promoter have been identified in the bean pal2 and parsley 4CL-1. Leyva et al., *Plant Cell* 4: 263-71 (1992); Hauffe et al., *Plant J.* 4: 235-53 (1993), respectively. A transcription factor in xylem, VSF-1, specifically interacts with the 20-base pair regulatory element sequence of the grp1.8 gene. The interaction of VSF-1 and the regulatory element was demonstrated by the formation of a high molecular weight complex between VSF-1 and the regulatory element, using an electrophoretic mobility shift assay, with the specificity of binding being demonstrated by the unlabeled DNA target competing for VSF-1 binding. Torres-Schumann et al., *Plant J.* 9: 283-96 (1996). The precise residues with which VSF-1 interacts were delineated further by measuring the sensitivity of the regulatory element to DNaseI. Briefly, the interaction of VSF-1 with the regulatory element prevents DNaseI from degrading certain residues that are contacted by the protein, by virtue of steric hindrance by the bound transcription factor. Typically, the DNaseI analysis also reveals residues that become hypersensitive to degradation when the transcription factor is bound. To verify that the putative regulatory element was xylem-specific, monomers or multimers of the putative regulatory region were fused upstream of a minimal CaMV 35S or minimal grp1.8 promoter. The putative regulatory region conferred xylem-specific expression on these promoters, as determined by the histochemical analysis using a fused β-glucuronidase gene operably linked to the modified promoter, stably transfected into tobacco. See Torres-Schumann (1996).

Functional Variants or Fragments of the Promoters of the Invention

Additional variants or fragments of the promoters of the invention are those with modifications interspersed throughout the sequence. Functional variants or fragments, as used herein, are nucleic acids that have a nucleic acid sequence at least about 70% identical to the reference nucleic acid, but still confer tissue-specific expression of coding products. The tissue-specificity or preference of the functional variant must be towards the same tissue as the reference nucleic acid. However, even if the functional variant is not as preferential or as specific as the reference nucleic acid, the variant is still considered a functional variant as used herein. In one embodiment, the sequence of the functional variant or fragment is at least about 75% identical to the reference nucleic acid. In other embodiments, the sequence of the functional variant or fragment is at least about 80%, 85%, 86%, 87%, 88%, 89%, 90%, 91%, 92%, 93%, 94%, 95%, 96%, 97%, 98% or 99%.

Modifications that can produce functional variants may be made by sequential deletion of residues from the 5' end or the deletion of 5' UTR sequences from the 3' end. Alternatively, internal residues may be modified. Modifications that do not affect the function of the promoter regions most likely will be those that do not affect the binding of transcription factors. The modifications encompassed by the invention also include those that occur naturally in the form of allelic variants of the promoters of the invention. The variants of the current invention are tested for organ or tissue specific, or organ or tissue preferred activity using the methods described herein.

Methods of Making the Nucleic Acids of the Present Invention

The nucleic acids of the invention can be obtained by using well-known synthetic techniques, standard recombinant methods, purification techniques, or combinations thereof. For example, the isolated polynucleotides of the present invention can be prepared by direct chemical synthesis using the solid phase phosphoramidite triester method (Beaucage et al., *Tetra. Letts.* 22: 1859-1862 (1981)), an automated synthesizer (Van Devanter et al., *Nucleic Acids Res.* 12: 6159-6168 (1984)), or the solid support method of U.S. Pat. No. 4,458,066. Chemical synthesis generally produces a single stranded oligonucleotide, which can be converted into double stranded oligonucleotides by hybridization with a complementary sequence, or by polymerization, using the single strand as a template. Also, longer sequences may be obtained by the ligation of shorter sequences.

Alternatively, the nucleic acids of the present invention can be obtained by recombinant methods using mutually priming oligonucleotides. See e.g. Ausubel et al., (eds.), CURRENT PROTOCOLS IN MOLECULAR BIOLOGY (John Wiley & Sons, Inc. 1990). Also, see Wosnick et al., *Gene* 60: 115 (1987); and Ausubel et al. (eds.), SHORT PROTOCOLS IN MOLECULAR BIOLOGY, 3$^{rd}$ ed., (John Wiley & Sons, Inc. 1995). Established techniques using the polymerase chain reaction provide the ability to synthesize polynucleotides at least 2 kilobases in length. Adang et al., *Plant Mol. Biol.* 21: 1131 (1993); Bambot et al., *PCR Methods and Applications* 2: 266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., *PCR Methods Appl.* 4: 299 (1995).

Methods of Using the Nucleic Acids of the Invention

The nucleic acids of the current invention are useful for altering characteristics of the plant. The nucleic acids may be operably linked to a gene of interest to increase the levels of a molecule found in the vascular tissue. Alternatively, the gene of interest may inhibit the formation of an ultimate end product, e.g. cellulose, thus the nucleic acids of the current invention can be used to decrease the levels of a predetermined molecule in vascular tissue.

One of the primary targets of such manipulated expression is the lignin biosynthetic pathway. For the reasons set forth above, there is considerable interest in regulating the amount of lignin in plants, either positively or negatively, which can be accomplished through expression of gene products that impact this pathway. For example, manipulation of the number of copies of CAD and COMT modifies lignin content, as described in U.S. Pat. No. 5,451,514 and WO 94/23044. Furthermore, antisense expression of sequences encoding CAD in poplar or pine leads to a modified lignin composition. Grand et al., *Planta (Berl.)* 163: 232-37 (1985); Baucher et al., *Plant Physiol.* 112: 1479 (1996), respectively.

Other characteristics which may be important to alter include sugars. Increasing the levels of enzymes responsible for sugar production, for example, in phloem tissue would increase the sugar content in the plants. Enzymes which may increase or decrease the levels of sugar production include, but are not limited to β-glucosidases, 1-3 β glucanase, 6-phospho-fructo-1-kinase, sucrose synthase, UDP-glucose-pyrophosphorylase, hexokinase, phosphoglucomutase, sucrose transporters, and invertases.

Additional characteristics include, but are not limited to, increasing insecticidal, antiviral or antibacterial proteins present in the leaves of the plant. Such proteins include, but are not limited to cecropins, thionins, defensin, lipid transfer proteins, hevein-like peptides, and GASA peptides. Still other characteristics include drought tolerance, cold tolerance, peroxidase activity, salt tolerance, and nitrogen transport.

The present invention, thus generally described, will be understood more readily by reference to the following examples, which are provided by way of illustration and are not intended to be limiting of the present invention.

EXAMPLES

Example 1

Isolation of Vascular-Specific Promoters

*Pinus radiata* and *Eucalyptus grandis* cDNA libraries were constructed and screened as follows. mRNA was extracted from plant tissue using the protocol of Chang et al., *Plant Molecular Biology Reporter* 11:113-116 (1993) with minor modifications. Specifically, samples were dissolved in CPC-RNAXB (100 mM Tris-Cl, pH8.0; 25 mM EDTA; 2.0M NaCl; 2% CTAB; 2% PVP and 0.05% Spermidine*3 HCl) and extracted with chloroform:isoamyl alcohol 24:1.

RNA was precipitated with ethanol and purified using MessageMaker kit (Life Technologies). A cDNA expression library was constructed from purified mRNA by reverse transcriptase (Loopstra et al., *Plant Mol. Biol.* 27:277-291 (1995)) synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY Broth (Gibco BRL, Gaithersburg, Md.) and plated out onto LB-kanamycin agar plates containing 5-bromo-4-chloro-3-indolyl-beta-D-galactoside (X-gal) and isopropylthio-beta-galactoside (IPTG).

Colonies were picked and DNA prepared using standard miniprep technology. Colonies containing a correct insert were cultured in NZY Broth with kanamycin and cDNA was purified by means of alkaline lysis and polyethylene glycol (PEG) precipitation. Agarose gel at 1% was used to screen sequencing templates for chromosomal contamination. Dye terminator chemistry was set up using Big Dye Chemistry (Applied Biosystems), according to the manufacturer's protocol.

The DNA sequence of positive clones were obtained using a 3700 Capillary Machine (Applied Biosystems) or a Prism 377 sequencer Perkin Elmer/Applied Biosystems Division. cDNA clones were sequenced first from the 5' end, and in some cases, also from the 3' end. For some clones internal sequence was obtained using subcloned fragments. Subcloning was performed using standard procedures of restriction mapping and subcloning into pBluescript II SK+ vector.

Plant EST sequences homologous to a selected gene were identified from either a *Pinus radiata* or *Eucalyptus grandis* cDNA expression library and are displayed in Table 2.

TABLE 2

| SEQ ID NO | Gene Homology | Species | BLASTX Hit | E Value | Identity |
|---|---|---|---|---|---|
| 1 | Glucosyl Transferase | *E. grandis* | Glucosyl Transferase | e-130 | 214/421 (50%) |
| 2 | Ted 2 (970 bp) | *E. grandis* | NADP-Dependent Oxidoreductase Ted2 | e-160 | 276/324 (85%) |
| 3 | Cyclin B (447 bp) | *E. grandis* | Putative G2/Mitotic-Specific Cyclin 1 (B-like Cyclin) | e-122 | 242/360 (67%) |
| 4 | Cyclin B (883 bp) | *E. grandis* | Putative G2/Mitotic-Specific Cyclin 1 (B-like Cyclin) | e-122 | 242/360 (67%) |
| 5 | Microtubule associated | *E. grandis* | AT2G45170 Putative Microtubule-Associated Protein | 2.00E-53 | 100/117 (85%) |

TABLE 2-continued

| SEQ ID NO | Gene Homology | Species | BLASTX Hit | E Value | Identity |
|---|---|---|---|---|---|
| 6 | CAP Adenyl Cyclase Associated | E. grandis | Adenyl Cyclase Associated Protein | 0.0 | 382/476 (80%) |
| 7 | Ferulate-5-Hydroxylase | E. grandis | Ferulate-5-Hydroxylase | 0.0 | 402/517 (77%) |
| 8 | Cellulose synthase | E. grandis | Cellulose Synthase | 0.0 | 845/978 (86%) |
| 9 | LIM promoter | P. radiata | LIM Domain Protein PLIM1 | 3.00E−78 | 126/175 (72%) |
| 10 | Pectate Lyase | P. radiata | Pectate Lyase | 0.0 | 298/379 (78%) |
| 11 | Expansin | P. radiata | Alpha-Expansin | e−122 | 197/240 (82%) |
| 12 | ACC Oxidase 1 1-Aminocyclopropane-1-carboxylate oxidase | P. radiata | ACC Oxidase | 9.00E−99 | 187/321 (58%) |
| 13 | 4-Coumarate CoA Ligase 3(4CL3) (contains 5'-end 40 bp insert) | P. radiata | 4-Coumarate-CoA Ligase (EC 6.2.1.12) | 0.0 | 392/533 (73%) |
| 14 | 4CL1 or 4CL2 (650 bp) | P. radiata | 4-Coumarate-CoA Ligase (EC 6.2.1.12) | 1.00E−89 | 168/175 (96%) |
| 15 | 4CL1 or 4CL2 (1650 bp) | P. radiata | 4-Coumarate-CoA Ligase (EC 6.2.1.12) | 3.00E−89 | 168/175 (96%) |
| 16 | Dirigent Protein | P. radiata | Dirigent Protein, Putative (Hypothetical 20.6 KDa Protein) | 5.00E−41 | 77/150 (51%) |
| 17 | Laccase (898 bp) | E. grandis | Laccase Precursor (EC 1.10.3.2) | e−153 | 263/318 (82%) |
| 18 | Laccase (500 bp) | E. grandis | Laccase Precursor (EC 1.10.3.2) | e−153 | 263/318 (82%) |
| 19 | Unknown protein Euc E11912 (600 bp) | E. grandis | AT4G27438 | 8.00E−65 | 122/172 (70%) |
| 20 | Cellulose-synthase like | P. radiata | Putative Glucosyl Transferase | 0.0 | 487/690 (70%) |
| 21 | 4CL3 (without 5'-end 40 bp insert) | P. radiata | 4-Coumarate-CoA Ligase (EC 6.2.1.12) | 0.0 | 392/533 (73%) |

Polynucleotide or polypeptide sequences can be aligned with other polynucleotide and/or polypeptide sequences and the degree of shared identical sequence can be determined using computer algorithms that are publicly available. The BLAST family of algorithms, including BLASTN, BLASTP, and BLASTX, is described in the publication of Altschul et al., "Gapped BLAST and PSI-BLAST: a new generation of protein database search programs," Nucleic Acids Res. 25:3389-3402, 1997. The BLASTN algorithm Version 2.0.11 [Jan. 20, 2000] set to the default parameters described in the documentation and distributed with the algorithm, are preferred for use in the determination of polynucleotide variants according to the present invention.

BLASTX searches were performed using SWISSPROT-TREMBLE Sequences [Jul. 9, 2002] and the searches were performed on Nov. 15, 2002. The following running parameters are preferred for the determination of alignments and similarities using BLASTX that contribute to the E values and percentage identity of polypeptide sequences: blastall -p blastx -d swissprotdb -e 10 -G 0 -E 0 -FF -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -F Filter Query Sequence [String]; -v Number of one-line descriptions (v) [Integer]; -b Number of alignments to show (b) [Integer]; -I Query File [File In]; -o BLAST report Output File [File Out] Optional.

The promoters were cloned using a "Genome Walker" kit (Clontech, Palo Alto, Calif.). This is a PCR-based method, which requires four PCR primers to be constructed, two of which must be gene-specific. The gene specific primers are designed generally within the 5' UTR of the gene. The fragment is amplified and then cloned into a T-tailed vector in front of the GUS reporter gene.

Example 2

Methodology to Determine the Tissue Specificity of a Promoter

Following the identification and cloning of a promoter by the procedure outlined above in Example 1, the promoter is operably linked with a reporter gene to determine those tissue types in which the promoter is active. To this end, a construct containing an inventive promoter is transformed into Agro-

*bacterium tumefaciens* by electroporation. Briefly, 40 μl of diluted AgL-1 competent cells are placed on ice and are contacted with about 10 ng of pART27 vector containing the promoter sequence. Electroporation is conducted under the following parameters:

Resistance=129 ohm
Charging voltage=1.44 kV
Field strength=14.4 kV/cm
Pulse duration=5.0 ms Following electroporation, 400 μl of YEP liquid media is added and the cells are allowed to recover for one hour at room temperature. Cells then are centrifuged at 6000 rpm for 3 min and are resuspended in 50 μl YEP. Cell samples are spread over the surface of a YEP Kan50/Rif50 plate, sealed with parafilm, and incubated at 29° C. for 2 days for colony growth.

Wild type *Arabidopsis thaliana* cv. 'Columbia-0' plants are then transformed with *Agrobacterium* containing constructs of interest by floral dip infiltration. Briefly, *Agrobacterium* cultures are centrifuged at ~8600 rcf for 10 min at 20° C. and are resuspended to an optical density of ~0.7-0.8. Plants are dipped into an infiltration solution containing the *Agrobacterium* for 5 sec. Plants are drained of excess solution and placed under grow lights in ambient conditions. After 24 hrs, the plants are misted and maintained for seed production. $T_1$ seeds are surface sterilized in 5% commercial bleach solution and plated on MS media containing Kanamycin (50 mg/l) and Timentin (250 mg/l) to select for putative transformants.

*N. benthamiana* plants are transformed with constructs of interest by *Agrobacterium*-mediated leaf tissue transformation (Burow et al., *Plant Mol. Biol. Rep.* 8:124-139, 1990).

Successfully transformed plants are then assayed for the expression of the operably linked reporter gene. Leaf, stem, root and floral regions are immersed in a staining solution (50 mM $NaPO_4$, pH 7.2, 0.5% Triton X-100, 1 mM X-Glucuronide, cycloheximide salt (Ducheffa). A vacuum is applied twice for 5 min to infiltrate the tissue with the staining solution. The tissue is then left shaking overnight at 37° C. for color development. Tissues are checked at three or four timepoints to check stain development, and if samples show early development, a piece of tissue is destained in 70% ethanol. This tissue is then examined for GUS expression using a light microscope and photographed.

Example 3

Isolation and Culture of *Zinnia elegans* Mesophyll Cells in Tracheary Element (TE) Inducing (FKH) and Non-Inducing (FK) Medium Primary and secondary pair leaves from *Zinnia* seedlings were harvested from 8 punnets. Leaves were sterilized in 500 ml of 0.175% sodium hypochlorite solution for 10 minutes. Leaves were then rinsed twice in 500 ml of sterile water. Using 20-30 leaves at a time, leaves were ground in 25-30 ml of FK medium with a mortar and pestle. The cells were filtered through a 40 μm nylon mesh and a total of 90 ml of mesophyll cells were obtained in this fashion. The cells were centrifuged at 200×g for 2 minutes at 20° C. and the resultant pellet was washed once more with an equal volume of FK medium. Upon completion of the second wash, the pellet was split into two equal halves, wherein one half was washed with 45 ml of FK medium and the other with 45 ml of FKH medium. The pellets were resuspended in 60 ml of FK medium and 60 ml of FKH medium, respectively. They were cultured in the dark in two 6-well plates on the rotary shaker set at 120 rpm.

Example 4

Isolation of *Zinnia elegans* Protoplasts from Leaves or Mesophyll Cells Cultured Overnight to Three Days in FK Medium and FKH Medium Sterile *Zinnia elegans* primary leaves (6-8 in number) were cut into 1 mm slivers and placed in 15 ml of cell wall digesting enzyme mix (1% Cellulase Onozuka R-10 and 0.2% pectolyase Y23 in Protoplast isolation buffer). Mesophyll cells cultured in FK medium (40 ml) or FKH medium (40 ml) were pelleted by centrifuging at 200×g for 2 minutes at 20° C. Each pellet was resuspended in 20 ml of sterile protoplast isolation buffer containing 200 mg Cellulase Onozuka R-10 and 40 mg Pectolyase Y23. The protoplasts were isolated by incubating the cell suspensions in CellStar culture plates for 2-4 hours on a rotary shaker set at 70 rpm at 23° C. The protoplasts were pelleted by centrifuging the contents of the plates at 200×g for 2 minutes. Each pellet was then resuspended in 20 ml of 24% sucrose solution.

Fukuda and Komamine Medium Stock Solutions

| Stock A (10X) | Stock B (400X) | Stock C (400X) | Stock D (400X) | Stock E (400X) |
|---|---|---|---|---|
| 20,200 mg $KNO_3$ | 2,500 mg $MnSO_4 \cdot 4H_2O$ | 3,700 mg $Na_2EDTA$ | 200 mg Glycine | 50 mg Folic Acid |
| 540 mg $NH_4Cl$ | 1,000 mg $H_3BO_3$ | 2,800 mg $FeSO_4 \cdot 7H_2O$ | 10,000 mg myo-Inositol | 250 ml Milli-Q water |
| 2,470 mg $MgSO_4 \cdot 7H_2O$ | 1,000 mg $ZnSO_4 \cdot 7H_2O$ | 250 ml Milli-Q water | 500 mg Nicotinic acid | |
| 1,470 mg $CaCl_2 \cdot 2H20$ | 25 mg $Na_2MoO_4 \cdot 2H_2O$ | | 50 mg pyridoxine hydrochloride | |
| 680 mg $KH_2PO_4$ | 2.5 mg $CuSO_4 \cdot 5H_2O$ | | 5 mg thiamine hydrochloride | |
| 1,000 ml Milli-Q water | 250 ml Milli-Q water | | 1,000 ml Milli-Q water | |

| For 1 Liter Solution | FK Medium | FKH Medium |
|---|---|---|
| Stock A | 100 ml | 100 ml |
| Stock B | 2.5 ml | 2.5 ml |
| Stock C | 2.5 ml | 2.5 ml |
| Stock D | 2.5 ml | 2.5 ml |
| Stock E | 2.5 ml | 2.5 ml |
| Sucrose | 10,000 mg | 10,000 mg |
| d-(−) Mannitol | 36,000 mg | 36,000 mg |

| | | | |
|---|---|---|---|
| 1-Naphthaleneacetic acid (NAA | | | 0.1 mg |
| 6-Benzyladenine (BA) | | | 0.2 mg |
| Milli-Q water | up to 1,000 ml | | up to 1,000 ml |

Example 5

Transfection of Zinnia elegans Protoplasts

Zinnia protoplasts suspended in 24% sucrose solution were overlaid with 1 ml W5 solution (150 mM NaCl, 125 mM $CaCl_2.2H_2O$, 5 mM KCl, 5 mM sucrose, pH 5.6-6) and centrifuged at 70×g for 10 minutes at 20° C. with brakes off. Floating protoplasts were harvested, resuspended in 10 ml W5 solution, and pelleted by centrifuging at 70×g for 10 minutes at 20° C. Protoplast pellets were resuspended in MaMg medium (450 mM mannitol, 15 mM $MgCl_2$, 0.1% MES, pH 5.6) at a density ~$5×10^6$ protoplasts/ml and aliquoted into individual 15 ml tubes (300 µl: $1.5×10^6$ protoplasts). For each construct, 5 µg DNA and 50 µg Salmon Testes DNA was added to the protoplast suspension, mixed, and incubated for 5 minutes at 20° C. Three hundred µl 40% PEG solution (40% PEG 3340, 100 mM $Ca(NO_3)_2.4H_2O$, 0.45 M mannitol, pH 9.0) was added to each protoplast aliquot, mixed, and incubated for 20 minutes at 20° C. Five ml of K3/0.4M sucrose (for 1 L solution: 4.3 g Murashige and Skoog plant salts, 100 mg Myo-inositol, 250 mg xylose, 10 mg Thiamin-HCl, 1 mg Nicotinic acid, 1 mg Pyridoxin-HCl, 1 mg NAA, 0.2 mg kinetin, 137 g sucrose, pH 5.6 adjust with KOH) was added to each aliquot of leaf-derived transfected protoplasts or transfected protoplasts from mesophyll cells cultured in FK medium and mixed. Similarly, 5 ml of K3/0.4M sucrose+0.1 ppm NAA+0.2 ppm BA was added to each aliquot of transfected protoplasts from mesophyll cells cultured in FKH medium and mixed. The transfected protoplast suspensions were incubated overnight at 23° C. in the dark.

Example 6

Harvesting of Transfected Zinnia elegans Protoplasts and Reporter Gene Analysis

Transfected Zinnia protoplast suspensions, prepared as described in Example 5, were individually harvested by adding 9.5 ml of W5 solution, mixing the contents of each tube, and centrifuging at 70×g for 10 minutes at 20° C. The bulk of the supernatant was decanted and the protoplast volume was brought to 900 µl. For each 900 µL sample, 300 µL of protoplasts were aliquoted into 5 ml polystyrene round-bottom tubes, resuspended in 500 µl W5 medium, and set aside for analysis of fluorescent reporter gene expression and cell viability. The remaining 600 µL of protoplasts and solution were transferred into individual microtubes and pelleted by centrifugation at 420×g for 2 minutes at 20° C. The protoplast pellet was assayed for GUS reporter gene expression as described by Jefferson, R. A., 1987, Plant Mol. Biol. Rep. 5, 387. GUS (MUG) assays were performed using a Wallac (Turku, Finland) Victor[2] 1420 Multilabel Counter. Umbelliferone was detected using a 355 nm excitation filter and a 460 nm emission filter for 1 second.

Example 7

In Planta Expression Data

Three weeks post-transfer to soil, transformed Arabidopsis and N. benthamiana tissues are analyzed for GUS reporter gene expression. To assay GUS expression, leaf, root, and floral materials are immersed in the GUS solution as described in Example 2. A vacuum is applied twice for 5 minutes to infiltrate the tissue with the staining solution and the tissue is then incubated overnight in a shaker at 37° C. for color development. Following overnight incubation, the tissue samples are then destained in 70% ethanol and examined under a light microscope for GUS expression. Table 3 contains the percentage of transformed Arabidopsis and N. benthamiana plants expressing GUS.

Three months post-soil transfer, tissues from N. benthamiana $T_1$ plants are embedded into paraplast, sectioned with a microtome, and analyzed with a light microscope for GUS expression. The GUS localization and microtome results, as shown in Table 3, demonstrate that the disclosed isolated nucleotide sequences confer reporter gene expression preferentially in vascular cambium, xylem, and/or phloem tissues.

TABLE 3

In planta GUS Vascular Expression

| SEQ ID NO | Size (bp) | No Plants GUS+ | No Plants Tested | % GUS Expression | GUS Vascular Localization | Microtome Results |
|---|---|---|---|---|---|---|
| 1 | 168 | 2 | 12 | 16.67 | Stem material | |
| 2 | 934 | 7 | 12 | 58.33 | | Cambial cells, early xylem |
| 3 | 408 | 11 | 12 | 91.67 | Stem, developing lateral roots | Cambium, xylem |
| 4 | 847 | 11 | 12 | 91.67 | cambium | Cambium initials, lateral roots |
| 5 | 286 | 8 | 12 | 66.67 | Phloem, pith, Phloem parenchyma | |
| 6 | 216 | 4 | 12 | 33.33 | xylem | |
| 7 | 473 | 7 | 10 | 70.00 | Not specified | |
| 8 | 519 | 8 | 10 | 80.00 | Not specified | |
| 9 | 1607 | 11 | 12 | 91.67 | Leaf veins, roots | |
| 10 | 1163 | 2 | 12 | 16.67 | Stem pith, primary xylem | |

TABLE 3-continued

In planta GUS Vascular Expression

| SEQ ID NO | Size (bp) | No Plants GUS+ | No Plants Tested | % GUS Expression | GUS Vascular Localization | Microtome Results |
|---|---|---|---|---|---|---|
| 11 | 881 | 11 | 12 | 91.67 | Stem, trichomes | Primary xylem cells |
| 12 | 638 | 5 | 5 | 100.00 | Stem, leaf veins, root tip | |
| 13 | 900 | 8 | 12 | 66.67 | Primary xylem, cortex, pith, anthers, tip of style | |
| 14 | 603 | 10 | 10 | 100.00 | Stem, leaf veins | |
| 15 | 1631 | 7 | 12 | 58.33 | Roots, leaf veins, stem | Primary xylem, cambial cells, xylem ray cells |
| 16 | 786 | 12 | 12 | 100.00 | Parenchyma, pith | Parenchyma, pith, xylem |
| 17 | 898 | 5 | 10 | 50.00 | Phloem, leaf veins, cortex-parenchyma cells/phloem cells, and epidermal cells | |
| 18 | 563 | 2 | 7 | 28.57 | Primary xylem, parenchyma cells | |
| 19 | 524 | 2 | 12 | 16.67 | Late developing xylem, roots | |
| 20 | 638 | 5 | 12 | 41.67 | Inner pith, parenchyma cells, xylem | |
| 21 | 862 | | | | | |
| 22 | 691 | | | | Stem pith | |
| 23 | 970 | 7 | 12 | 58.33 | Vascular tissue | Cambial initials, early xylem |
| 24 | 447 | 11 | 12 | 91.67 | Stem, Vascular tissue, lateral roots | Differentiating Cambial initials, xylem, |
| 25 | 883 | 11 | 12 | 91.67 | Vascular tissue | Cambial initials, xylem, lateral roots, |
| 26 | 500 | 7 | 10 | 70.00 | Vascular tissue | |
| 27 | 650 | 8 | 10 | 80.00 | Vascular tissue | |
| 28 | 252 | 4 | 12 | 33.33 | Vascular tissue | Xylem, branch points |
| 29 | 322 | 8 | 12 | 66.67 | Vascular tissue | Pith, cortex, phloem |
| 30 | 204 | 2 | 12 | 16.67 | Vascular, stem material | |
| 31 | 784 | 6 | 8 | 75.00 | Vascular tissue | |
| 32 | 1161 | | | | Vascular tissue | Phloem, xylem, cambium |
| 33 | 500 | 2 | 7 | 28.29 | Vascular tissue | Xylem, parenchyma |
| 34 | 524 | 5 | 12 | 41.67 | Vascular tissue | Early, developing xylem, metaxylem |
| 35 | 1766 | 12 | 12 | 100.00 | Vascular tissue | Xylem, cambial cells, secondary xylem |
| 36 | 650 | 12 | 12 | 100.00 | Vascular tissue | Phloem, xylem |
| 37 | 894 | 9 | 9 | 100.00 | Vascular tissue | Primary xylem |
| 38 | 583 | 3 | 6 | 50.00 | Vascular Tissue | Primary xylem |
| 39 | 898 | 11 | 11 | 100.00 | Vascular Tissue | Xylem |
| 40 | 611 | 6 | 7 | 85.86 | Vascular Tissue | Inner pith cells |
| 41 | 537 | 7 | 10 | 70.00 | Vascular Tissue | Primary Xylem, phloem |
| 42 | 362 | 11 | 11 | 100.00 | Vascular Tissue | Xylem |
| 43 | 810 | 8 | 9 | 88.89 | Branch, base tissue | Xylem |
| 44 | 335 | 10 | 12 | 83.33 | Vascular | Xylem |
| 45 | 476 | 8 | 9 | 88.89 | Stem, vascular | |
| 46 | 536 | 8 | 11 | 72.73 | vascular | Xylem vessels, |
| 47 | 716 | 6 | 7 | 85.86 | vascular | Xylem, cambial, ray cells |
| 48 | 1643 | 11 | 12 | 91.67 | Vascular, stem material | xylem |
| 49 | 917 | 11 | 12 | 91.67 | Vascular, stem material | Primary xylem |
| 50 | 900 | 8 | 12 | 66.67 | Vascular material | Primary xylem, |

TABLE 3-continued

In planta GUS Vascular Expression

| SEQ ID NO | Size (bp) | No Plants GUS+ | No Plants Tested | % GUS Expression | GUS Vascular Localization | Microtome Results |
|---|---|---|---|---|---|---|
| 51 | 650 | 10 | 10 | 100.00 | Vascular material, stem section | Xylem, lignified xylem |
| 52 | 1650 | 12 | 12 | 100.00 | Vascular material | Xylem vessels |
| 53 | 1200 | 2 | 12 | 16.67 | Stem material, pith | Phloem, xylem |
| 54 | 674 | 5 | 5 | 100.00 | Stem, veins | |
| 55 | 822 | 12 | 12 | 100.00 | Parenchyma, stem | Xylem, cortex, thickened xylem cells |
| 56 | 1300 | 2 | 12 | 16.67 | Vascular material | |
| 57 | 674 | 5 | 12 | 41.67 | Vascular material | Xylem, pith, parenchyma cells |
| 58 | 1350 | 9 | 12 | 75.00 | Vascular material | Xylem rays, xylem |
| 59 | 700 | 2 | 7 | 28.57 | Stem sections | Xylem ring, cortex |

*N. benthamiana* tissue samples are placed in a vial containing fixative solution (100% Ethanol, Glacial acetic acid, 37% Formaldehyde, mQH$_2$O) and a vacuum is applied twice for 15 minutes. The samples are incubated in the fixative solution for two hours to ensure tissue infiltration. Following tissue infiltration, a vacuum is reapplied for 15 minutes and the tissues are placed at 4° C. overnight.

Following overnight incubation, the tissue samples are dehydrated through a series of ethanol incubations, wherein all incubations occur at room temperature. The overnight fixative solution is removed from the vial containing the tissue samples and replaced with 50% ethanol. After 30 minutes, the 50% ethanol is decanted and the tissues are incubated in a fresh aliquot of 50% ethanol. After 30 minutes in 50% ethanol, the solution is removed and replaced with 60% ethanol. Following 30 minute incubation, 60% ethanol is replaced with 70% ethanol. The 70% ethanol is decanted after 30 minutes and replenished with 85% ethanol. Following 30 minute incubation, the 85% ethanol is removed and the samples are incubated overnight in 95% ethanol.

Following tissue dehydration, the tissues are incubated at room temperature in a series of xylene solutions. The overnight 95% ethanol solution is removed, and the tissues are incubated in 100% ethanol for 30 minutes. After 30 minutes, 100% ethanol is removed and the tissues are suspended in 25% Xylene:75% Ethanol. Following 30 minute incubation, the solution is replaced with 50% Xylene:50% Ethanol. The solution is then decanted and replenished with 75% Xylene: 25% Ethanol. After 30 minutes, the tissues are thrice incubated in 100% Xylene for 60 minutes. The tissues are then overnight incubated in a vial containing xylene and 20 paraplast chips.

To infuse the paraffin, the vials are placed in a 42° C. hybridization oven until the paraplast chips dissolve. Throughout the course of 8 hours, a total of 60-80 paraffin chips are added to the vial and allowed to dissolve. The samples are left overnight in a 62° C. hybridization oven. Over the course of the next two days, the paraplast is changed four times, at 12 hour intervals. To embed the tissues, the liquid paraffin is poured into the cassette and the tissues are placed in the proper orientation. The cassette is then placed at 4° C. overnight to allow the paraffin to harden.

As illustrated in Table 3, the disclosed isolated nucleotide sequences confer GUS reporter gene expression preferentially in vascular cambium, xylem, and/or phloem tissues. Of particular interest, SEQ ID NO 21 and SEQ ID NO 13 share substantial sequence homology, except SEQ ID NO 13 contains a 40-bp fragment insertion at its 5'-end (AAATATAA-CATAATCTAACTATTGATGTACATT ATTCGCC). This 40-bp fragment (SEQ ID NO: 85) is present as an imperfect repeat in SEQ ID NO 13, yet is absent in SEQ ID NO 21. Interestingly, in the presence of the 40-bp fragment (e.g. SEQ ID NO 13), GUS expression is conferred, while in the absence of the fragment (e.g. SEQ ID NO 21), there is no GUS expression. This data is significant because it suggests that the disclosed 40-bp fragment (SEQ ID NO: 85) may constitute an element necessary and sufficient for vascular-preferred gene expression.

Example 8

Methods of Using a Vascular-Specific Promoter

Once a promoter having an appropriate tissue-specific and developmental pattern of expression is found, this promoter can be used to regulate a desired characteristic in a transgenic plant. In one embodiment, a xylem-specific promoter is used to regulate the composition and content of lignin in a plant. In this example, a xylem-specific promoter of the invention is operably linked to a gene encoding an RNA interference (RNAi) molecule corresponding to a portion of the coding region of cinnamyl alcohol dehydrogenase (CAD). CAD catalyzes the last step of lignin monomer synthesis and has provided a target for successful antisense-mediated down-regulation of lignin in transgenic plants using other promoters. See Yahiaoui et al., *Phytochemistry* 49: 295-306 (1998) and references cited therein. Expression of an RNAi molecule corresponding to a portion of CAD results in a decrease in the enzyme activity and a corresponding increase in the proportion of cinnamyl aldehydes in the lignin of the transgenic plants. CAD activity in transgenic plants is assayed by the method of Wyrambik et al., *Eur. J. Biochem.* 59: 9-15 (1975) as adapted by Baucher et al., *Plant Physiol.* 112: 1479-90 (1996). Lignin content and composition are measured as set forth by Baucher (1996). Down-regulation of CAD results in a color change in the wood and an increase in the proportion of more easily extracted cinnamyl aldehydes, which is commercially important for plants used in the pulp industry. Id. For example, poplars with decreased CAD activity display red coloration, and the lignin is more easily extractable, which improves the properties of the poplar trees for application in the paper industry. See Baucher et al. (1996).

In another example, *Eucalyptus* and pine are transformed. *Eucalyptus* and pine provide useful model systems for studying the effect of gene regulation on lignin content and composition because of its the high lignin content. Additionally, *Eucalyptus* and Pine exemplify plants in which the modulation of lignin content or composition can provide useful properties with respect to the paper or lumber industries.

To construct these transgenic plants, a fragment of CAD cDNA is operably linked in proper orientation to a xylem-specific promoter of the invention and a nopaline synthase 3' terminator. The CAD cDNA can be prepared, for example, by reversing the orientation of the gene sequence with respect to its promoter. Transcription of the CAD cDNA in the plant cell will generate an intracellular RNA transcript that is "antisense" with respect to the CAD gene. The entire construct is inserted as a restriction fragment into the binary vector pBI101.1 (Clontech, Palo Alto, Calif.). Vectors are electroporated into *A. tumefaciens* strain LBA4404 or C58 pMP90, for eucalyptus or pine transformations, respectively. See generally, No et al., *Plant Science* 160: 77-86 (2000). Kanamycin resistant transformants are tested for CAD activity, transgene copy number is determined by Southern analysis, and mRNA expression of CAD is determined as described in Yahiaoui (1998). Suitable transformants then are rooted and transferred to a greenhouse.

Example 9

In Silico Expression

In silico gene expression can be used to determine the membership of the consensi EST libraries. For each library, a consensus is determined from the number of ESTs in any tissue class divided by the total number of ESTs in a class multiplied by 1000. These values provide a normalized value that is not biased by the extent of sequencing from a library. Several libraries were sampled for a consensus value, including Cambium, Xylem, Phloem, Vegetative Bud, Root, Reproductive tissues, Leaf, Stem, and Fruit libraries. As shown below in Tables 4-5, a number of the inventive promoter sequences exhibit vascular-preferred expression and thus are likely to be involved in wood-related developmental processes.

TABLE 4

*Eucalyptus grandis* Expression Profile

| SEQ ID NO | Bud (Veg) | Cambium | Fruit | Leaf | Phloem | Reproductive | Root | Stem | Xylem |
|---|---|---|---|---|---|---|---|---|---|
| 24 | 0.42 | 1.99 | 0.08 | | | | | | 2.33 |
| 27 | | 0.35 | 0.54 | | 0.17 | | 0.12 | 0.95 | 7.71 |
| 31 | 0.59 | | | 0.17 | | | | | |
| 33 | 0.08 | 3.69 | 0.85 | 1.56 | 0.28 | | 0.08 | 0.95 | 15.68 |
| 36 | | | | 0.83 | | | | | |
| 37 | | 1.31 | 0.15 | | 0.17 | 4.01 | 0.32 | | 1.23 |
| 59 | | | | | | | | | |
| 60 | | 11.98 | 0.15 | 3.35 | 0.17 | | 0.08 | 0.95 | 47.12 |
| 61 | 0.25 | 4.69 | 0.15 | 0.51 | 0.83 | 6.69 | 0.08 | 0.24 | 3.78 |
| 62 | | | | 0.35 | | | 0.35 | | 0.47 |

TABLE 5

*Pinus radiata* Expression Profile

| SEQ ID NO | Bud (Veg) | Cambium | Fruit | Leaf | Phloem | Reproductive | Root | Stem | Xylem |
|---|---|---|---|---|---|---|---|---|---|
| 24 | 0.42 | 1.99 | 0.08 | | | | | | 2.33 |
| 27 | | 0.35 | 0.54 | | 0.17 | | 0.12 | 0.95 | 7.71 |
| 31 | 0.59 | | | 0.17 | | | | | |
| 33 | 0.08 | 3.69 | 0.85 | 1.56 | 0.28 | | 0.08 | 0.95 | 15.68 |
| 36 | | | | 0.83 | | | | | |
| 37 | | 1.31 | 0.15 | | 0.17 | 4.01 | 0.32 | | 1.23 |
| 59 | | | | | | | | | |
| 60 | | 11.98 | 0.15 | 3.35 | 0.17 | | 0.08 | 0.95 | 47.12 |
| 61 | 0.25 | 4.69 | 0.15 | 0.51 | 0.83 | 6.69 | 0.08 | 0.24 | 3.78 |
| 62 | | | | 0.35 | | | 0.35 | | 0.47 |

TABLE 6

| SEQ ID NO | Gene Homology | Sequence |
|---|---|---|
| 1 | E. grandis Glucosyl transferase | AAAACCACAAATGGCCGCGGGACGTCA-CAATTTT TTTTTCCTTCTAGAAGCTCTATAGT-CAAAGCTGA TCTATAAATTTTTGGGAACCACAACCAC-CATGTC TCGCCACCTTCGCTCGAACCTTATCAC-CACCACC GCCCTTGAGCCCTCCTCCATCAACTCTTCTTC |
| 2 | E. grandis Ted (2) | AAAACAATGTAGCTTCTCTGTGTTAT-GAAAACTA ACAAAAGGGCACATCTATTTCTCCAT-GACCATTA TATTCGGAGGAGCATGGTCAAACT-TAAATCAAAA TTTATTATCCATAACTTACAAATTTC-CAATTTAG CTAAACTCAAATCCCAAAGTATAGCAAT-TCTGTT AAAATTTTATCATCCGATAGTATAGAG-CAATATT TTATAATACTTACATTGCTCAGCTCAAT-TACAAA TTCTATTTGTCCACAAATTCAAACATTT-TAATGA TGCATTCCACATAAAACCAATG-GTTTGAGACACC TTTTCAAAAAAAAGAAAAAAATACAC-TAGCATTG CTTAGACAAGTTAATCAAT-GAAAAATAACTTTAT CTTGTTTTAATTAAGGATGAAAAG-GAGTTACAA ACGCTTGTTTCAA-GATAAATATTTTTCAAATCTT TAATATTACAAGAAATAAACGGACCT-TCTTATCA ACCAAAAAAATGTAACATAAAAGGAACT-TACCAA TTTGATTGGACTCATTTATTGATTTTTG-GAAAAA TGTCGCAAATTTTCGTTGAGTTT-TAGCTCCATGT ACAATTTAGTCATTGAACTTTTAATT-TATTCAAT ATAATTCATGAACTTTCTATACATATT-TAGTCCA TATAAAAATTAAGGGACCAAATTGAG-TATTCACC AAAATTTTAGGGAAAATAT-TGAATAAATAAAAAG TTCTTGGACCAAATTTCATAT-TGAAATAAAATTC ATGGACAAATCATTATTCCTTGAT-TAAACTTTTT TATGTAGACACCCGTAAATACAACCTGC-CAAGGT TTGTTTGCAAGGCGTTTGCAAG-GCGTTTGCACTT AAGCGGGACGGAGGCGTCACCAGT-CAATGGGCAT GTCCAGTGGCTTCCCCGGCTTGCGAAT-AGGATGC TTCCTGAATCATCTCC |
| 3 | E. grandis Cyclin B | AAAGTTTCTCTGTAGAGAGGGAGG-GAGATATA TCTGCGGTTTGCGTCTCTATTTCGCT-TGTGCAGT TTTACTACTCCCCAAACACACACA-CACTCTCT GTTTCTCTCCTTTTTCCCCAAATCAGAA-GAAGAA ACGACAGTGTAGTAGTGCAGTTTCACTA-CACCGT CTATACTAAGGG-TAATCGTTTTTTGAAAGCACA TGCATATAGCCGTTGGAAAGGG-GAGGGCACCGAG ATCGAATCGGATGGCTGATCCTCAC-TAGCCGTTA GAGAGAGAGAGAGAGAGGGAGGGATAAT-CATGTG CGGACATATATCCGCAATTTGCGTCTC-TATTTCG CTTGTGCAGTTTCACTACTCCCCACACA-CACTCT CTCTCTCTCTCTCCTTTTC-CCCCAAATCAGAA |
| 4 | E. grandis Cyclin B | CCTTGTATTTCCCCAACATTAAAT-GAAAGCCTAC ATCCCATCCTTTATTTCAACCCTAAAGT-GAAATT AAGATATAAGACGAAACCACCCCCAAC-CCCCCAA AAAAAAAATATTAAGGGAAT-TCGTTTTTTTGAAA GCACATGCGGAGGTAGCTGTTG-GAAAGGGGCCTC TACGTTCGGAAGGAATGCGACCATTC-CATCGAGA TCAAATCGAACTACTGATGCTCAC-TAGCTGTTGC GTTTAAACCTTCTTTGTAAAGC-GATAAGGGAATT CGTTATTTTGAAAGCACATGCGGAGG-TAGCCATT GGAAAGGGGCCTCTACGTTCGGAAGGAA-CACGAC CGTTCCACCGAGATCGAATCGGACCGT-TGATGCT CACTAGCCATTGTGTTTAAAGTTTCTCT-GTAGAG AGAGGGAGGGAGATATATCGCG-GTTTGCGTCTC TATTTCGCTTGTGCAGTTTTACTACTC-CCCAAAC ACACACACACTCTCTCTGTTTCTCTC-CTTTTTCC CCCAAATCAGAAGAAGAAACGACAGTG-TAGTAGT GCAGTTTCACCACCGTCTATAC-TAAGGGTAAT CGTTTTTTGAAAGCACATGCATATAGC-CGTTGG AAAGGGGAGGGCACCGAGATCGAATCG-GACGGCT GATCCTCACTAGCCGTTA-GAGAGAGAGAGAGA GGGAGGGATAATCATGTGCGGA-CATATATCCGCA ATTTGCGTCTCTATTTCGCTTGTG-CAGTTTCACT ACTCCCCACACA-CACTCTCTCTCTCTCTCTCT CCTTTTCCCCAAATCAGAA |
| 5 | E. grandis Microtubule-Associated Protein | AAATTATGCAATTTCTTAATCAGGC-CTAGCTAGA AACAAGGGCAAGGAAAGC-CCCCGACGGGCTCTTA TCTGCTGACGTGGCACGC-CGTGGGTGGGCCCCCC CGGGTCTTCCTTCGACGAAACCTCATCG-TAGACA ATCAAATCCTCCTCTCGATCATTATTG-CAAAGCC AACACCCAGCATTGAATCGATCCCCAC-CTTCTCC TCCTCCTCCTCTTGATCCTTTTTGTC-CCGATGAT GATGGGTATCTGATCAGCCGATTCAATC-CCATCG TCTCCTTCCTTCTC |
| 6 | E. grandis CAP adenyl cyclase | GTGCGGACACGTGTCCCCTTATCCCGC-CCAAGAC CGCGCAAAACCTGAAAATCCTCACTAT-TCCCTCA CTTTCGGCGAATTCGAAACAGCGCAT-AAAGGAAC |

TABLE 6-continued

| SEQ ID NO | Gene Homology | Sequence |
|---|---|---|
| | | ACGGAAAGAACATTCTCTACCCCAAGAC-GACGAC |
| | | GACGACGACGACGACGACGCCGCGCCT-TATATAA |
| | | ACCATCGCCACTCCTGGCCATTCCCT-TCTTTCTC |
| | | CCCAGATCCAAT |
| 7 | E. grandis Ferulate-5-Hydroxylase | AAAGATAAAAATAGTGTGGAAAATA-GATTTGAGA |
| | | AGTGTTCATATATTTCGATTTATCATAG-CAAAGA |
| | | ATCTTGAGATATATAGAAACCGACA-GAAAATATA |
| | | TTGATTATCTCTAATATAGAATAATAT-TCTAGAG |
| | | AAGTATTGTAATTTTTATCGACCTATTT-TAGGCT |
| | | TTATAGTGTGACTATTTAAGATAAC-GAATATTAA |
| | | TCGAGAGATGCACAATTAATAA-GAGATATTCTCA |
| | | CGTGTGACCACCAACTAAAATGGGGCA-GACAAAG |
| | | TAGAGGGCCAGGTATAGTCAAGGCCAGT-GAAAAG |
| | | GAAAATGAAATGAAATAAAAGAAAA-GAAAAGAAA |
| | | AATCAAATCCTCCAACTTGTGTACAG-GATACACC |
| | | CGAAGCTTTGTGTATATAAAGGCCACT-TAATATC |
| | | TCCTCCAACCTAGCAACACATTCGAAA-GATAAGT |
| | | TGCGCTTAAATCCTCTCCAAAAGAGCTAATC |
| 8 | E. grandis Cellulose Synthase | CTGCTGAAATTCTCGAGGAAGTTGAGAG-GTTCCA |
| | | GATTAGATCTTTACCAAA-CAAAAAAAAACTATTG |
| | | CTTATGCTAAATTGGTCATTATAATAA-GATTTTT |
| | | AGAATACTCGTTGAGTATACTCAACT-CAAGATAT |
| | | TATAAGTTTTTCTCAATTGGTTTTTCTC-CATTTCT |
| | | TATGATCCGTCCACGAGCTTG-GAGTCGCTTTTGA |
| | | AGATGTAGCCAGCCCAACAGAAC-CGTTTCCTTCA |
| | | TCTTCCCGCGAAAGTTTCATGTCATCTC-CCTCCT |
| | | CTGCATCACGAACCAAACCTCT-GCTCTCTCTC |
| | | TCTCTCTCTCTGCTTCAACACAATGA-CACCAACA |
| | | TCGCACCCTCCTCACCTTCCCAACCAC-CGCCATA |
| | | CCATCTCCTTTAAGCATTCCGATGAGTC-CCTGAT |
| | | CCACCGCCTTCTCACTGAGCCTTC-CCGCTCTCCC |
| | | TCTTCTCGTCTCACTTTCTCATATAAA-GAAGTGA |
| | | AAGAATACGAGGATACTCCACTTGGG-TATCGCCA |
| | | AGAACTCAT |
| 9 | P. radiata LIM Promoter | CCTTTGGGAATGAACTTTGAGACCAC-CTCCAACC |
| | | CGGATTCTGAAATCCATCCAGCAATTC-CAAAGTT |
| | | CCAAACCGAAATAAACATCCCACCATAC-CATGGC |
| | | ATTCGGAAAAAAGCTAGGCTAAGCT-GAAAATCAC |
| | | TGTCATAACCCAGTAAGACCATGCCAC-TAATAGC |
| | | AAGAGAACCATACACCAACATGCAAAGC-CATGCA |
| | | TGTCCAAACCAGCTAGGAAATCACACAT-GCAAAG |
| | | GGTTACCTGCAAGTATTCCTGTTGAAGT-TGCTTG |
| | | ATCCTACTTTCTTTTCCTTGAGCCT-TGCTTGCCT |
| | | TCCTTTCCTTTGCTTGATTTTCCTTTC-CTTGCTC |
| | | CAAACTAGAGTGCTCTAA-GAAAACTCTAAGTGAC |
| | | CAAGAGAGTGAGAGAGAGAGAATAAT-GAGAGT |
| | | CCAAACATGAACTTGACAAAAGCCAT-GAACTGAT |
| | | CCTCAGAAGTCATTTATGCACGAGGCT-TCTATT |
| | | TTCTTCATTTTCCATCATTTTCCT-TCAATTTCCT |
| | | CATCACATGCAACGTGCGACTTTTCAC-CCCGTTT |
| | | TCCTCCTAATTTCTTTTATTTTCAT-AAATAAATG |
| | | TGCCAAAAATGCCTCTTGCCTTAGC-CTTTGCCAG |
| | | TTTCCTTAGCCAAAACACACATCCAAT-GATGCCC |
| | | ACTAGGATATCTTTGCCCAACATTAAGC-CTGGAA |
| | | TAAATGTCTCTTAATCGTGGTCT-TATTTTGCTTT |
| | | TATTAACTTTTATTCAT-GAACTTTTCACTAAAG |
| | | CTATTACAAAGATATATTTATTATG-GCAATTATG |
| | | TTTGATTTTTGAAGAGCTAGTAACTTT-TAGTTTA |
| | | TTATGGCCTTTTCCGTAAACT-TATTTTCTTGAAA |
| | | ATCTCTATAAATCCAATGAAAAATT-TATAGAATA |
| | | TATGTTGTGTTTTCTTCACTAC-CTCTAATAAATT |
| | | TTTTACTTAGTAATCTACAAAGCCATT-TATTAAA |
| | | AAATTCAAGTTAATTAAAAATTAATAT-CATTTCA |
| | | AAAGTCTTTTTAATATAGTCAAAGTT-TATTAAAT |
| | | TCTATGATGTATATTTCTTT-TAAATAAATGAAGA |
| | | ATCCATTTTTTTACTTAAAAC-CATATATTTTTA |
| | | TAACGTTGATAAATAGCATGCATT-TATATAAACA |
| | | AATATATATTTTTATAACGTTAAGAGAT-TGTTAA |
| | | AACTTTTAAATAATTAATATTTTATT-TATTGTTT |
| | | TGAAAATGTCATGATTTCCACCTAC-CTCGCCCAT |
| | | CAAATCTTGCTGCAAACCAGGCTTAC-CCAACCCC |
| | | ACACCCACAATATATTTTTGGGATCTG-GTGCCCC |
| | | CACCTTTGATCACAGTGAACACCATAAA-GACAAA |
| | | TTATAAAGGCAAGGGACTTGGCAC-CCATGAGGC |
| | | AACCGAAAGCAACAAATCATTTTTTTC-CAAAGAG |
| | | ATGAGTGTATGCCAACGAAGAAACAC-GATGAACC |
| | | CACGTGTCATTGGCCAACTCCCACTTTC-GACAAA |
| | | AAGAAGGAAATTAGAATTAAAAAGGC-GAATAAAA |
| | | ATTGAAAGGCCATTTAAAATAGAAGGAA-GAATAG |
| | | CCTATATGGTAGATTTAAAT-GCTTTTTTGAAATC |
| | | CGGTTACTCGCAAGATTATCAATCGG-GACTGTAG |
| | | CCGAAGCTT |

TABLE 6-continued

| SEQ ID NO | Gene Homology | Sequence |
|---|---|---|
| 10 | P. radiata Pectate Lyase | AAACAGAGCAGATAACACTAAAAAGAC-CAACCCT<br>GTTAGGAGGGGAGAAACAAAAAGATCA-CACTAA<br>AAAGACCAACCCTCTTATCTAAACT-TATTTTCTC<br>TTATCTCTACCCCTTCTATTTTGAAC-CTTTATCA<br>TTTTGATAGAAATATATGTTAATAAC-CATTAAA<br>CCTACATTGTCAAGCTAGTGTAACT-TATATGTTA<br>ATAACCATTAAACCTACATTGTCAAGT-TAGTGTA<br>ACTCCTTTGGTGGGGTGGTTGTCTTC-CTCTTCA<br>ATCTCATGCTATGACACACTTGTTTTT-TAATAAC<br>ATAGGCCGACAAGTTTGAGCCATTATC-TATCTTG<br>ATTCCTCGAAATGATAAATAGATGTTGT-CAGTGG<br>ACTTGAAAAAACCAAGTAGGGAACAC-CACGTAA<br>TCTTTCCAATGGCATTAAAAGC-TACTTTGAAATA<br>TGTAACACTTAGCAATCCTTCCAAG-GCATTAAAC<br>CTACTCTAACCTATGGAACACTTAG-CATCCTTCC<br>CACGGTTGATAATAAATGATTGATTCCT-CAGAAT<br>AACAAATAAAAAAAACTATAAAACT-TACTCTAA<br>AATATAAAATGAGTATGGAACACGTG-GCAATCCT<br>TCCCATGCTCGGCGGTAGCTACTCTCTC-CAGAGA<br>TTTGAATAACACAGGCGCCGCAATTAT-GAGAGAG<br>CAGTGGAGTTAAGACTTAGTAGCCATG-GTTATTT<br>TGAACGCGTGGCAATTCTTCCAAAGGT-TGGTAGT<br>TACTCTATCCAGAGATTTGAATAACA-CAAATGCT<br>GCAGTTATGAGAGAGTAGTAGAGT-TAAGTCTTGT<br>CAGCAATGATAGTTACGAACAACCG-TAATTTCTG<br>GCTATCTCTGTGTTTATTGGTCGTT-TACTTGCTA<br>CAGTGCTCTCACCCCACATGGTAACAGT-GTTCGA<br>TGGCCATGATTTCTCCCCACCCCGC-CAAACCTCT<br>ACGTTTTTATTCTTTTAATAACTC-CTAATTTAAT<br>ATATAAGAGGGGCAAGGTGTTCATACA-GATTCG<br>TGCAAACGACCTGAGTTCAGCACAAGTT-TAGTCA<br>TTCCATGCAACTCGACTGGCTCAC-GAGATCCCT<br>CGCTGCAGTTATAGATTGCAGGAATT-AGCTTAGC<br>AGCATTTCTATCTATGATCTTCTGC-CACTTCTTC<br>CCCTCTC |
| 11 | P. radiata Expansin | AAATTAGTCAAATCCAAAGCAGACAACT-TGGGCT<br>CTCACCTAAATTAACACATATACCCTAC-CAGCTT<br>CCATAGTTTTCCAACTTC-CTTTCAATAAATCTATT<br>CAAAAGCATGAAAAGCATGACTAAGGT-TCAATTC<br>CCAAGTTATGGACACCCACCTGCTCTAG-GCATAT<br>AGGAAATCACAATCCAACTAACGAC-CAACTACCC<br>AAAACTTTGAAGAAAATGAGTAAA-GACTCCCCCA<br>GTGATATTATAATTATATGGTCTCTCTA-GAACCC<br>TTTATTGCCCCTTCCAGTGTTATATT-TAGTTCCC<br>CATTTATATATCCCTTGACTTATGAAAC-CATTTA<br>GGTGCATTAACATAGTCCTTGACTAA-CAAAAAAA<br>TTATTTAGGTGCAGTAGATACGGAAAG-TAACCAA<br>TGATGCTAAGAAACTGTGCACGTACTT-TAATGGA<br>GGTATTACTTTTATTATGGTTGGTTTG-GATACAT<br>TCATAATGGAAGCATGTGCTCT-TCATCGTTAAAG<br>TTGTGGTGGGGCATTCCCCATTTTCCAC-GAGAAA<br>CCGAATCCCGGCGTGGAGACGACGAC-GAAATCGA<br>TGGATATTCGGTGGAAAATTCACAG-TAAAATTCC<br>TGGAGAAAAGGTTGCCGAGGTAGT-TGAAATCCA<br>AACCGCCGAAATGAGCTGGAAACCCGC-CTTCTGT<br>CAGTTAGTTGAGTCATGACTGCAGCT-GTCTCAGG<br>TCTTACACTGTAAAGGCACCTTAATGAG-GCATTC<br>ATTCTGGCAGTCTGGCTACGGAACT-TAATAGTAC<br>TTGTTATTCCTGCCCCAATATCTATT-TAATAGGC<br>ATCCCCCCTCACTACTTCTTGCCCA-CAATCCCTC<br>CATAGTCCTGAGCTTGAGACCATTTTTCTGC |
| 12 | P. radiata ACC oxidase | AAGGTTTGCTTGGACCAGCGACACAGG-GAAAAAC<br>ATGGCATGCGGGTTTGGATTAAGATGAG-GCCCAA<br>TCTTAATTTGATATGTTTGCCAAACCT-TAGGTTG<br>TTTATCTAATTTTTGATTGGATCT-GATCTCTTGA<br>TGATTTAAGGGTTTTCCATGTTGACACG-CAATTG<br>TAGGTTCCTGGGCACTAAGGTCTACCAT-GTGGCG<br>AATTTATCGAGAGTTGACAATTCTGG-TACTGTTA<br>GTGATTTGTCACCACTCTACGGTCCCTG-CAGATC<br>TCAGATTTTTAATGGCTGCCTTTGAT-TATCTAAA<br>GGCTAGCCCCTAATCGCGGCTATGAATG-TATAAA<br>GAATGTGTTCCAATGCATTAGAGTACT-CAAAGAC<br>ATGTTGAAGGAAAAGGACAAGTCAAGG-GACATGA<br>GTAATAACCAAAAAAGCACTTGGTCCT-GACCATC<br>TGTGTCTGATTCACACTGGGATTCACAT-GTTATT<br>TAAGAAAAGTTGCATCAGTGCTGCAAT-CATCAAG<br>CCATTCCTAATTTACCACCATGATTA-GATTATTT<br>TAATGCAAGAAAACGCCTATATAAG-GAGAGCTGC<br>AGGCCCCAAGGTAATGCAGTAAT-CAAACTTGAGG<br>AGAGATTTGAGAGTGTTTGTGAAGGG |
| 13 | P. radiata 4CL3 | AAATATAACATAATCTAACTATTGATG-TACATTA<br>TTCGCCTATAACAAAATCTAAGTAT-TGATGTCAC |

TABLE 6-continued

| SEQ ID NO | Gene Homology | Sequence |
|---|---|---|
| | | ATTATTGGCATATAACAAAATCTTTAG-GATAACC |
| | | CCTTAGTCAAGCTCTTGTACTTTCAT-GTTTATTA |
| | | ACCAATAAATCAAGCTGATATGGAATAG-CAGACG |
| | | TACGTGGTAATAATAAATGGAGTGTAA-GAGTTCG |
| | | AACATTTTAATTCGGAGGGGCAGCTTAT-GTGGAA |
| | | TATCAGGCAATCATACAAGCT-TGCTTTTGGGTAA |
| | | TAAAGACCCACATGTGGTAATAA-CAAGTGGATTT |
| | | TAACAAACCAACATTTTGATAGGGAG-GATAGGTG |
| | | GCCTGGTAAGTTAGAATGTGCTAGTCAT-GCCTTT |
| | | GAAAGAAGTTAGTTGTGGAAGTCAAA-CATGTTCC |
| | | CCACACAACACACCTCACCACACAAAT-GCTGGT |
| | | AGGTCATGTGATTGATGGATGGGCATGT-GTATCC |
| | | TCCAAAAAAAATGAATATACACAC-TAAATATTCT |
| | | ATTGACATAATAATATACAAAGAAGATTAG-GTCTATG |
| | | GAAGAAGGGAAGGCGAAGGGGAAGAT-TGGGTCGT |
| | | GGGGAAGATTGGGTCGTGTCCTGCTAG-CACGTTG |
| | | AATACCTACACGCCATTTCACATCTAC-CCATCAA |
| | | CGTCAAATAGAGCATCCAAAT-CAGGGCGTGGTGG |
| | | TGTGAGGGGAGAGTGAGGAGAAGAAGT-TGAAAAA |
| | | TTCTGGCTGAAAATCCACCTAACA-CACGCTCACC |
| | | AGCCCCTCAACGAGGGGCACCAATTAT-GAATAAT |
| | | AATAGCTAGAACAGAGCAGCAGAAGCA-GAGTTTA |
| | | TATCTATCCATTGTCGTCTGTAAAT-TACTCTGTG |
| | | AGTGTTTAGTGTTTTCTTCTCTTAT-TGATTTCAG GGGACAAGTAGGTGGG |
| 14 | P. radiata 4CL1 or 4CL2 | AAACACCAATTTAATGGGATTTCA-GATTTGTATC |
| | | CCATGCTATTGACTAAGCCATTTTTC-CTATTGTA |
| | | ATCTAACCAATTCCAATTTCCACCCTG-GTGTGAA |
| | | CTGACTGACAAATGCGGCCCGAAAA-CAGCGAATG |
| | | AAATGTCTGGGTGATCGGTCAAA-CAAGCGGTGGG |
| | | CGAGAGAACGCGGGTGTTGGCCTAGC-CGGGATGG |
| | | GGGTAGGTAGACGGCGTATTACCGGC-GAGTTGTC |
| | | CGAATGGAGTTTTCGGGGTAGGTAG-TAACGTAGA |
| | | CGTCAATGGAAAAAGTCATAATCTCCGT-CAAAAA |
| | | TCCAACCGCTCCTTCACATCGCAGAGT-TGGTGGC |
| | | CACGGGACCCTCCACCCACTCACT-CAATCGATCG |
| | | CCTGCCGTGGTTGCCCATTATTCAAC-CATACGCC |
| | | ACTTGACTCTTCACCAACAATTCCAGGC-CGGCTTT |
| | | TCGAGACAATGTACTGCACAGGAAAATC-CAATAT |
| | | AAAAGGCCGGCCTCCGCTTCCTTCTCAG-TAGCCC |
| | | CCAGCTCATTCAATTCTTCCCACTGCAG-GCTACA |
| | | TTTGTCAGACACGTTTTCCGC-CATTTTTCGCCTG |
| | | TTTCTGCGGAGAATTTGATCAGGTT |
| 15 | P. radiata 4CL1 or 4CL2 | ATCTTATGGAGTTTT-TAAATATATATATATTTTT |
| | | TGGGTTGAGTTTACTTAAAATTTG-GAAAAGGTTG |
| | | GTAAGAACTATAAATTGATTGAGTTGT-GAATGAG |
| | | TGTTTTATGGATTTTTTAAGATGT-TAAATTTATA |
| | | TATGTAGTTGTGAAGGAGTGTTTTATG-GATTTTT |
| | | TAAGATGTTAAATGTGTATATGTAAT-TAAAATTT |
| | | TATTTTGAATAACAAAAAATTATAATTG-GATAAA |
| | | AAATGTTTTGTTAAATTTAGAG-TAAAAATTTTAA |
| | | AATCTAAAATAATTAAACACTAT-TATTTTTAAAA |
| | | AATTTGTTGGTAAATTTTATCTTAAATT-TAGTTA |
| | | AAATTTAGAAAAAAAATAATTTTTAAT-TATTAAC |
| | | TTTTGAAGTCAAATATTCCAAAT-GTTTTCCAAAA |
| | | TATTAAATTCATTTGACATTCAAAATA-CAATTTA |
| | | AATAACAAAACTTCATGAAATAGAT-TAACCAATT |
| | | TGTATGAAAACCAAAAATCT-CAAATAAAATTTAA |
| | | ATTACAAAATATTATTAACATTAT-GATTTCAAGA |
| | | AAGAGAATAACCAGTTTC-CAATAAAATAAAACCT |
| | | CATGGCTGGTAATTAAGATCTCATTAAT-TAATTC |
| | | TTATTTTTTAATTTTTTTACATA-GAAATATCTT |
| | | TATATTATATACGAGAAATATAGAATGT-TCTAGT |
| | | CCAAGGACTATTAATTTC-CAAATAAGTTTCAAAA |
| | | TCATTACATTAAAACTCATCATGT-CATTTGTGGA |
| | | TTGGAAATTAGACAAAAGAGAATC-CCAAATATTT |
| | | CTCTCAATCTCCCAAAATAAACCTAAT-TAATATA |
| | | GTTCGAACTCCATATTTTTGGGAAT-TGAGAATTT |
| | | TTCTACCCAATAATATATTTTTTTTATA-CATTTT |
| | | AGAGATTTTCCAGACATATTTGCTCTGG-GATTTA |
| | | TTGGAATGAAGGTTTGAGTAATGAAG-GTTTGAGT |
| | | TATAAACTTTCAGTAATCCAAGTATCT-TCGGTTT |
| | | TTGAAGATACTAAATCCAT-TATATAATAAAAACA |
| | | CATTTTAAACACCAATTTAATGG-GATTTCAGATT |
| | | TGTATCCCATGCTATTGGCTAAGC-CATTTTTCTT |
| | | ATTGTAATCTAACCAATTCCAATTTC-CGCCCTGG |
| | | TGTGAACTGACTGACAAATGCGGC-CCGAAAACAG |
| | | CGAATGAAATGTCTGGGTGATCGGT-CAAACAAGC |
| | | GGTGGGCGAGAGAACGCGGGTGTTGGC-CTAGCCG |
| | | GGATGGGGGTAGGTAGACGGCGTATTAC-CGGCGA |
| | | GTTGTCCGAATGGAGTTTTCGGGGTAGG-TAGTAA |
| | | CGTAGACGTCAATGGAAAAAGTCAT-AATCTCCGT |

TABLE 6-continued

| SEQ ID NO | Gene Homology | Sequence |
|---|---|---|
| | | CAAAAATCCAACCGCTCCTTCACATCG-CAGAGTT |
| | | GGTGGCCACGGGACCCTCCACCCACT-CACTCAAT |
| | | CGATCGCCTGCCGTGGTTGCCCATTAT-TCAACCA |
| | | TACGCCACTTGACTCTTCACCAACAAT-TCCAGGC |
| | | CGGCTTTCGAGACAATGTACTGCACAG-GAAATC |
| | | CAATATAAAGGCCGGCCTCCGCTTCCT-TCTCAG |
| | | TAGCCCCCAGCTCATTCAGTTCTTC-CCACTGCAG |
| | | GCTACATTTGTCAGACACGTTTTCCGC-CATTTTT |
| | | CGCCTGTTTCTGCGGAGAATTTGATCAGGTT |
| 16 | P. radiata Dirigent | AAACGCTTCATGCCCCAGAAGCCG-CACTCGATGC |
| | | TTTAGAATAAAATGGACCATTACCAGAC-TACGCG |
| | | CCTCCAAAATAACAAAAACGTGTATT-AGTTAAAC |
| | | CCTACATAGCACTTAAAGCTTGTCTTAC-TATTAT |
| | | TTTACGTAATTCTGTCTTTTTGACAGTG-GATTGA |
| | | TTGGAACTTCCATTCTCGATACAGTTG-TATGCGT |
| | | TATGTGAACTGAACCAACCTCGGC-CAAAATATGG |
| | | GGAAGATTCACTTCAGAAAAGACAGGA-CAACCAT |
| | | CTCTGATTGTCGACATTAATATCG-GAAAAATTC |
| | | AGTCAAATGATGTGGAAAGGTTCATC-TACGGAAA |
| | | ATAAAATAGCTCTGAGATGACCCGTTA-CATTTAG |
| | | TGCATAGCATCTTTGTCAACAAGAA-GAAATTTCC |
| | | AGTTGTAGGACTGGTCATCAATGGCGT-GCCTGC |
| | | AACGCTTTTTCGCAACAGGAAACACG-GACTAAAA |
| | | AACGCGGTCTATCTGTCATTTGACGG-TACGTTTG |
| | | GCACTGAGCCCGAAAAATCCCATTGG-TAGAATT |
| | | TAGAAGAGGGAGCTTTCACTCGAAAAT-TCTGTAC |
| | | CACAAGCGGTGGCCTCACAATAACAAAT-TATTAT |
| | | ACCCACATGGAAAATGTTAAATCGGACG-GTCCGA |
| | | CGGTCGACCAAAGACAAAATTGAT-GAGAAAGTTT |
| | | TGAGGGTGGGTGATAAAG-TAAGCGCGTCTTTTCA |
| | | CAGGCATCTGCATTATAAACCTG-CAACTCCAACT |
| | | TTCATCACAACAAATTTCATTTTCCCCT-TCTCTG AGGC |
| 17 | E. grandis Laccase | AAAAAATTTATAACTAATATTGGTA-CAATTAGAA |
| | | ATTCTCTTGCCTTCCTTAATCTTGCTGT-TAACTC |
| | | CTCCATTTTAGGCGTAGACAAC-TATTTTTTTCC |
| | | ACAAAAATGAAACAGTTCCTAAATAGAC-TAACGC |
| | | CTTTTAAGCTGGTAGTAGACAGACCGA-CACAAAA |
| | | TCCTGAACAGGCATGTACCGACACAAA-GAGATTC |
| | | ATTTCACGAGTAAATTTGAATTTCGA-CAACTAAT |
| | | TCTACACATCGGTAATCACG-CAAATATATCGAT |
| | | CGGCAAAAAGTTATATTTTAGACAGT-GACGTGAC |
| | | ATCTCAAGCACCCAATCCCTCTCAACAG-GTGAAG |
| | | AGCCATATTTTCATTACATAAAG-GCATTTTTTTT |
| | | TTTTAATTTTTAATAGGTGGTCCGAC-CGACAAGA |
| | | TATTATTATTTTTCTATTTGCATGAA-GAAGAAAA |
| | | AGATTGGTTTTGACCACAATGGTTTGTC-CTCTCG |
| | | TTACCCATTTTATATTTGGCAAGTTTG-GTGATTG |
| | | ATTGTAGAAGAAACACGAAACACACGAG-CAAAAG |
| | | TAAAGGACTCCAAACCCAAATTTTAATC-CACAAA |
| | | CGAATTTACCCACATAAAAAAAGGG-GAGATTATG |
| | | ATTAAATTCGTTGAATAATGCGACCCTT-TAGGAG |
| | | AAGGCTTATTAAGCAAGCATCGACG-GAAGCTACA |
| | | CACTCCTTTTGGGGAGAGGCTAGTGGGT-GCAACA |
| | | ACTACGATTCGGGTA-GAGCTAAGCTTTGTCCCCA |
| | | GTGGCGGTACTGCCATGAC-CAGGGCTCTAAATCA |
| | | AAACCTAATCTGCCAACCTCAAAA-CAAACGCTGT |
| | | CTCGCCCCCCCCGGCTGCGCTATATAAT-GCAGCC |
| | | GATGGCGTCCTTCCTTTCTCGAAC-CCTAAGCAGA |
| | | TCAAGAGTTTGAGT |
| 18 | E. grandis Laccase | GTGAAGAGCCATATTTTCATTACAT-AAAGGCATT |
| | | TTTTTTTTTAATTTTTAATAGGTGGTC-CGACCGA |
| | | CAAGATATTATTATTTTTCTATTTGCAT-GAAGAA |
| | | GAAAAAGATTGGTTTTGACCACAATG-GTTTGTCC |
| | | TCTCGTTACCCATTTTATATTTG-GCAAGTTTGGT |
| | | GATTGATTGTAGAAGAAACACGAAACA-CACGAGC |
| | | AAAAGTAAAGGACTCCAAACCCAAATTT-TAATCC |
| | | ACAAATGAATTTACCCACAT-AAAAAAAGGGGAGA |
| | | TTATGATTAAATTCGTTGAATAATGC-GACCCTTT |
| | | AGGAGAAGGCTTATTAAGCAAGCATC-GACGGAAG |
| | | CTACACACTCCTTTTGGGGAGAG-GCTAGTGGGTG |
| | | CAACAACTACGATTCGGGTA-GAGCTAAGCTTTGT |
| | | CCCCAGTGGCGGTACTGCCATGAC-CAGGGCTCTA |
| | | AATCAAAACCTAATCTGCCAACCT-CAAAACAAAC |
| | | GCTGTCTCGCCCCCCCCGGCTGCGC-TATATAATG |
| | | CAGCCGATGGCGTCCTTCCTTTCTC-GAACCCTAA GCAGATCAAGAGTTTGAGT |
| 19 | E. grandis Unknown Protein | AAATTTTTTTTTTTTTGGGTGGGTAG-TAGGAT |
| | | CTGTCGAGTAAAGTGACTTAACGC-CAATTCTCG |
| | | ACATTTCAGACTAATAAAATATTTACA-GATGCAA |
| | | CGTCTCACTCTCCTTGCAAACCA-GAAAGGGA |
| | | CAGCAAGCAAGAAGAGGGGGAAGAGAA-GACTTGC |

TABLE 6-continued

| SEQ ID NO | Gene Homology | Sequence |
|---|---|---|
| | | GTTTTAAGCAAGGGGAGTGCT-GACTTTTCAAGCG |
| | | ACTTAATTAATCTGTTTAGCAC-CCACTTTGGTTC |
| | | GTTTGATCTTCTCGTGATTTATTATT-TACCTATG |
| | | TACAGCTGCGGTTGAAATGGC-CTCTCTCGCTTAA |
| | | ATGGTAGTTTGTCCTTTTCTTGGGGTG-GTTGCTT |
| | | TGGAAATATTCTTTTAGAAG-CAGGGGCAAAGAAA |
| | | TGGAGTGGCATCTGATGCTTCTTCAA-CACTTTGC |
| | | AGCCATATCGAGAATATATACCTA-GAGAGAGAGA |
| | | GAGAGAGAGAGAGAGAGAGGAGCAGTG-GAGAAGA |
| | | AGGAGAAGAAGAAAAGGGTCAGATCA-GATCCAGT |
| | | TGTTGGGAGCAAGT |
| 20 | P. radiata Cellulose-synthase like | CTGTATTCATCACTTTACACCCATGAT-TCCAAAC |
| | | CCTACACATTTACACTGATAAC-CAAGGGTTCAGG |
| | | TTCTTTTCCAATTCATTTTAATCCAGGAT-GATAAT |
| | | AAATTTGAATAGCACAATAGCATATTC-CAACTGC |
| | | ATATCCCTACATTTGGGATCTCTTTC-CACGTTAT |
| | | AAATGGCTTCAATTTAGGGATCCCTTTC-CACATT |
| | | ATATAACTGGGTTCACAGTGGTTTGAA-GATAGCT |
| | | GTGGTTTGAAGATAGCTGTATATGTTAT-CAAAAT |
| | | GACAGCTCCCTTGCCAGGGACCATCGCT-TGAATG |
| | | ATGAGATCCCGCCTGTAAGGCAACTTG-CAGCATG |
| | | ATTATTTTACATCTGCTTGACCAAT-TATCTAACA |
| | | ATATACGCGGTGTCGTCGTTCGGT-TAAATAATAG |
| | | TGAAACTTCCTCGTGTTGTCCCTGCAGT-TACGTA |
| | | TGTCTTGTTCTTTTTTTTGTTTAATAa-CATACAG |
| | | CAGAGCAAGTGTTGGGTGAATAAATAT-TGGGAAG |
| | | AAGCTGCAGCGTTCACGTTCATTCAT-TCACTCAT |
| | | CGTGAGCAGCAGTACATCAACAGTTCT-TGAAGAA |
| | | CATTGATAGGTTGGCTATTTCAATC-CTTTCATGG |
| | | GGAATATTTAAGTCTGGATCCGAGC |
| 21 | P. radiata 4CL3 | AAATATAACATAATCTAACTATTGATG-TACATTA |
| | | TTCGCCTATAACAAAATCTTTAG-GATAACCCCTT |
| | | AGTCAAGCTCTTGTACTTTCATGTTTAT-TAACCA |
| | | ATAAATCAAGCTGATATGGAATAGCA-GACGTACG |
| | | TGGTAATAATAAATGGAGTGTAAGAGT-TCGAACA |
| | | TTTTAATTCGGAGGGGCAGCTTATGTG-GAATATC |
| | | AGGCAATCATACAAGCTTGCTTTGGG-TAATAAA |
| | | GACCCACATGTGGTAATAACAAGTG-GATTTAAC |
| | | AAACCAACATTTTGATAGGGAGGATAG-GTGGCCT |
| | | GGTAAGTTAGAATGTGCTAGTCATGC-CTTTGAAA |
| | | GAAGTTAGTTGTGGAAGTCAAACATGT-TCCCCAC |
| | | ACAACACACCTCACCACACAAAATGCTG-GTAGGT |
| | | CATGTGATTGATGGATGGGCATGTG-TATCCTCCA |
| | | AAAAAAATGAATATACACACTAAATAT-TCTATTG |
| | | ACATAATATACAAGGAAGATTAGGTC-TATGGAAG |
| | | AAGGGAAGGCGAAGGGGAAGAT-TGGGTCGTGGGG |
| | | AAGATTGGGTCGTGTCCTGCTAGCACGT-TGAATA |
| | | CCTACACGCCATTTCACGTCTACCCAT-CAACGTC |
| | | AAATAGAGCATCCAAATCAGGGCGTG-GTGGTGTG |
| | | AGGGGAGAGTGAGGAGAAGAAGT-TGAAAAATTCT |
| | | GGCTGAAAATCCACCTAACACACGCT-CACCAGCC |
| | | CCTCAACGAGGGGCACCAATTAT-GAATAATAATA |
| | | GCTAGAACAGAGCAGCAGAAGCAAAGTT-TATATC |
| | | TATCCATTGTCGTCTGTAAATTACTCT-GTGAGTG |
| | | TTTAGTGTTTTCTTCTCTTAT-TGATTTCAGGGGA |
| | | CAAGTAGGTGGG |
| 22 | E. grandis Euc ATHB8 | AAACGGACAGGAACCAAACTGGATCG-GATCCAAT |
| | | TCCTAGTCCTAAAACCAACCAATC-CCCACTTTCT |
| | | AATTTTTGGAATCGGTCCTATAGGTTC-CATTTTG |
| | | AAATCGATCGCCCTTATATGAATGAAA-GAGCGCT |
| | | CACATGTACCGTTAGATGGTATAGAC-CTAATAAT |
| | | CTGATAATCTGATGGCTCAT-TGCGTTTTGAGCTC |
| | | ACATGGAGCGAGATTATGTAATAAT-GACGTCAGG |
| | | GAGAGGAGAGGAGAGAAGATGAA-GAGAAAGCTGT |
| | | GGAGAAACAAAACACAAGGCTCGTTG-GAAGCAAC |
| | | GTAAACAACAGCAAACAACATCAA-CAACGGCGAC |
| | | AAAAGAA-GAGAGAGAGAGAGAGAGAGAGGA |
| | | AACAAAAACAAAAGCAAAAGTTGGG-GAGTGAAGA |
| | | GGGGAAAAGAAAGATGATGTGAAAA-CAAACCAAA |
| | | CTCTCCTTTTCTTCCACCTCT-CATTTTCTGTCTG |
| | | GTATATGGGGGTCTCTCTCTCTC-CCTCTCTCT |
| | | CTCTCTCTCTACCTTCTCTCTC-TACTTTCTCTTT |
| | | CTTAGGGGGGGCGTCCCCAGGGTCTC-CGATCCC |
| | | AATATCATTCCCCCCCACTCTTTTGCT-GCCATAT |
| | | ACATACAAAAACCGAAGCTTGTGAA-CAACCCAT |
| | | CTCTCTCTCTCTCTCTC-CCTCTCTCTTTCTGCCT |
| | | GCGAAACTGTGTC |
| 23 | E. grandis Euc Ted 2 | AAAACAATGTAGCTTCTCTGTGTTAT-GAAAACTA |
| | | ACAAAAGGGCACATCTATTTCTCCAT-GACCATTA |
| | | TATTCGGAGGAGCATGGTCAAACT-TAAATCAAAA |
| | | TTTATTATCCATAACTTACAAATTTC-CAATTTAG |
| | | CTAAACTCAAATCCCAAAGTATAGCAAT-TCTGTT |

TABLE 6-continued

| SEQ ID NO | Gene Homology | Sequence |
|---|---|---|
| | | AAAATTTTATCATCCGATAGTATAGAG-CAATATT |
| | | TTATAATACTTACATTGCTCAGCTCAAT-TACAAA |
| | | TTCTATTTGTCCACAAATTCAAACATTT-TAATGA |
| | | TGCATTCCACATAAAACCAATG-GTTTGAGACACC |
| | | TTTTCAAAAAAAGAAAAAAATACAC-TAGCATTG |
| | | CTTAGACAAGTTAATCAAT-GAAAAATAACTTTAT |
| | | CTTGTTTTTAATTAAGGATGAAAAG-GAGTTACAA |
| | | ACGCTTGTTTCAA-GATAAATATTTTTCAAATCTT |
| | | TAATATTACAAGAAATAAACGGACCT-TCTTATCA |
| | | ACCAAAAAAATGTAACATAAAAGGAACT-TACCAA |
| | | TTTGATTGGACTCATTTATTGATTTTG-GAAAAA |
| | | TGTCGCAAATTTTCGTTGAGTTT-TAGCTCCATGT |
| | | ACAATTAGTCATTGAACTTTTAATT-TATTCAAT |
| | | ATAATTCATGAACTTTCTATACATATT-TAGTCCA |
| | | TATAAAATTAAGGGACCAAATTGAG-TATTCACC |
| | | AAAATTTTAGGGAAAATAT-TGAATAAATAAAAG |
| | | TTCTTGGACCAAATTTCATAT-TGAAATAAAATTC |
| | | ATGGACAAATCATTATTCCTTGAT-TAAACTTTTT |
| | | TATGTAGACACCCGTAAATACAACCTGC-CAAGGT |
| | | TTGTTTGCAAGGCGTTTGCAAG-GCGTTTGCACTT |
| | | AAGCGGGACGGAGGCGTCACCAGT-CAATGGGCAT |
| | | GTCCAGTGGCTTCCCCGGCTTGCGAAT-AGGATGC |
| | | TTCCTGAATCATCTCC |
| 24 | E. grandis Euc cyclin | AAAGTTTCTCTGTAGAGAGAGGGAGG-GAGATATA |
| | | TCTGCGGTTTGCGTCTCTATTTCGCT-TGTGCAGT |
| | | TTTACTACTCCCCAAACACACACA-CACTCTCTCT |
| | | GTTTCTCTCCTTTTTCCCCAAATCAGAA-GAAGAA |
| | | ACGACAGTGTAGTAGTGCAGTTTCACTA-CACCGT |
| | | CTATACTAAGGG-TAATCGTTTTTTTGAAAGCACA |
| | | TGCATATAGCCGTTGGAAAGGG-GAGGGCACCGAG |
| | | ATCGAATCGGATGGCTGATCCTCAC-TAGCCGTTA |
| | | GAGAGAGAGAGAGAGAGGGAGGGATAAT-CATGTG |
| | | CGGACATATATCCGCAATTTGCGTCTC-TATTTCG |
| | | CTTGTGCAGTTTCACTACTCCCCACACA-CACTCT |
| | | CTCTCTCTCTCTCCTTTTC-CCCCAAATCAGAA |
| 25 | E. grandis Euc cyclin | CCTTGTATTTCCCCAACATTAAAT-GAAAGCCTAC |
| | | ATCCAAAAACGTGGACCCGGCATTAAA-GAAAAAC |
| | | CCCATCATCTCATCCCATCCTT-TATTCAACCCT |
| | | AAAGTGAAATTAAGATATAAGACGAAAC-CACCCC |
| | | CAACCCCCCAAAAAAAAAATATTAAGG-GAATTCG |
| | | TTTTTTTGAAAGCACATGCGGAGG-TAGCTGTTGG |
| | | AAAGGGGCCTCTACGTTCGGAAGGAAT-GCGACCA |
| | | TTCCATCGAGATCAAATCGAACTACT-GATGCTCA |
| | | CTAGCTGTTGCGTTTAAACCTTCTTTG-TAAAGCG |
| | | ATAAGGGAATTCGTTATTTTGAAAGCA-CATGCGG |
| | | AGGTAGCCATTGGAAAGGGGCCTC-TACGTTCGGA |
| | | AGGAACACGACCGTTCCACCGAGATC-GAATCGGA |
| | | CCGTTGATGCTCACTAGCCATTGTGTT-TAAAGTT |
| | | TCTCTGTAGAGAGAGGGAGG-GAGATATATCTGCG |
| | | GTTTGCGTCTCTATTTCGCTTGTG-CAGTTTTACT |
| | | ACTCCCAAACACACACACTCTCTCT-GTTTCT |
| | | CTCCTTTTCCCCCAAATCAGAAGAA-GAAACGAC |
| | | AGTGTAGTAGTGCAGTTTCACCACAC-CGTCTATA |
| | | CTAAGGGTAATCGTTTTTTTGAAAGCA-CATGCAT |
| | | ATAGCCGTTGGAAAGGGGAGGGCAC-CGAGATCGA |
| | | ATCGGACGGCTGATCCTCACTAGCCGT-TAGAGAG |
| | | AGAGAGAGAGAGGGAGGGATAATCATGT-GCGGAC |
| | | ATATATCCGCAATTTGCGTCTC-TATTTCGCTTGT |
| | | GCAGTTTCACTACTCCCCACACA-CACTCTCTCTC |
| | | TCTCTCTCTCCTTTTCCCCCAAATCAGAA |
| 26 | E. grandis Euc F5H | AAAGATAAAAATAGTGTGGAAAATA-GATTTGAGA |
| | | AGTGTTCATATATTTCGATTTATCATAG-CAAAGA |
| | | TTTTATCGACCTATTTTAGGCTTTAT-AGTGTGAC |
| | | TATTTAAGATAACGAATATTAATC-GAGAGATGCA |
| | | CAATTAATAAGAGATATTCTCACGATCT-TGAGAT |
| | | ATATAGAAACCGACAGAAAATATAT-TGATTATCT |
| | | CTAATATAGAATAATATTCTAGAGAAG-TATTGTA |
| | | ATTGTGACCACCAACTAAAATGGGGCA-GACAAAG |
| | | TAGAGGGCCAGGTATAGTCAAGGCCAGT-GAAAAG |
| | | GAAAATGAAATGAAATAAAAGAAAA-GAAAAGAAA |
| | | AATCAAATCCTCCAACTTGTGTACAG-GATACACC |
| | | CGAAGCTTTGTGTATATAAAGGCCACT-TAATATC |
| | | TCCTCCAACCTAGCAACACATTCGAAA-GATAAGT |
| | | TGCGCTTAAATCCTCTCCAAAAGAGCTAATC |
| 27 | E. grandis Euc cellulose synthase | CTGCTGAAATTCTCGAGGAAGTTGAGAG-GTTCCA |
| | | GATTAGATCTTTACCAAA-CAAAAAAAAACTATTG |
| | | CTTATGCTAAATTGGTCATTATAATAA-GATTTTT |
| | | AGAATACTCGTTGAGTATACTCAACT-CAAGATAT |
| | | TATAAGTTTTCTCAATTGGTTTTCTC-CATTTCT |
| | | TATGATCCGTCCACGAGCTTG-GAGTCGCTTTTGA |
| | | AGATGTAGCCAGCCCAACAGAAC-CGTTTCCTTCA |

TABLE 6-continued

| SEQ ID NO | Gene Homology | Sequence |
|---|---|---|
| | | TCTTCCCGCGAAAGTTTCATGTCATCTC-CCTCCT
CTGCATCACGAACCAAACCTCT-GCTCTCTCTC
TCTCTCTCTCTGCTTCAACACAATGA-CACCAACA
TCGCACCCTCCTCACCTTCCCAACCAC-CGCCATA
CCATCTCCTTTAAGCATTCCGATGAGTC-CCTGAT
CCACCGCCTTCTCACTGAGCCTTC-CCGCTCTCCC
TCTTCTCGTCTCACTTTCTCATATAAA-GAAGTGA
AAGAATACGAGGATACTCCACTTGGG-TATCGCCA
AGAACTCAT |
| 28 | E. grandis
Euc CAP | GTGCGGACACGTGTCCCCTTATCCCGC-CAAGAC
CGCGCAAAACCTGAAAATCCTCACTAT-TCCCTCA
CTTTCGGCGAATTCGAAACAGCGCAT-AAAGGAAC
ACGGAAAGAACATTCTCTACCCCAAGAC-GACGAC
GACGACGACGACGACGACGCCGCGCCT-TATATAA
ACCATCGCCACTCCTGGCCATTCCCT-TCTTTCTC
CCCAGATCCAAT |
| 29 | E. grandis
Euc microtubule associated | AAATTATGCAATTTCTTAATCAGGC-CTAGCTAGA
AACAAGGGCAAGGAAAGC-CCCCGACGGGCTCTTA
TCTGCTGACGTGGCACGC-CGTGGGTGGGCCCCCC
CGGGTCTTCCTTCGACGAAACCTCATCG-TAGACA
ATCAAATCCTCCTCTCGATCATTATTG-CAAAGCC
AACACCCAGCATTGAATCGATCCCCAC-CTTCTCC
TCCTCCTCCTCTTGATCCTTTTTGTC-CCGATGAT
GATGGGTATCTGATCAGCCGATTCAATC-CCATCG
TCTCCTTCCTTCTC |
| 30 | E. grandis
Euc glycosyl transferase | AAAACCACAAATGGCCGCGGGACGTCA-CAATTTT
TTTTTCCTTCTAGAAGCTCTATAGT-CAAAGCTGA
TCTATAAATTTTTGGGAACCACAACCAC-CATGTC
TCGCCACCTTCGCTCGAACCTTATCAC-CACCACC
GCCCTTGAGCCCTCCTCCATCAACTCTTCTTC |
| 31 | E. grandis
SAD | CTGTCACCTCTGGCTGGTCGCCGAACCT-CAGCGA
CCGACTGGAGGAAGAAGAGGAAAA-GAAAAAAATA
AAAATAAAATTCTAAAATATTAAAATAT-TATTAA
AAGTTGTCCACGTCAGCGTTGAGGC-CACGTTAAC
TAGCCGGTGTCGAGTCAGCAAAATTCG-GCCAAAA
TTGGCACAAAAAAAGGTTTAG-GACTTTTTTGACG
CTTTTCCCGTCATGAGCCTAAATAA-GAAATTTTA
ATTTCTTCATACCATACCAAT-TATTTGATATGAG
ATTTTTCTAACTAATTCACACATCTAT-GCTAACG
CTACTCGCTCAAAAAGCGCTCAAGCT-GAAGCCAA | GTTTCAAGCATCAAGCTTATAAGC-CGAGCCAAGC
TCGAGCACGGTGCTTCTTTTCTCGGCCT-GACCCG
ATTAGACTCTTGACTGAACATGACATAT-GAAATT
GCAGAGCATTCAATTTAAAAGATTGT-GAAATTTC
TGGGCATTTATTTACCTCCCTGTTAAT-GATATTG
CAGAGCATTCAATTTAAAAGATTGT-GAAATTTCTG
GGCATTTATTTACCTCCCTGTTAAT-GATATTTT
ATGGAATAGCGTGCAAAGAATTCGGGTG-CATAGT
GTTGTCCTTCTCCCAACGCCCCCT-TATATAATCT
CCGAACGGAGCAAGCATTTGCTCTTCCG-TACCCA
CGGCATTTTCCTTCTCGTGACCTTTTC-CCGAGAA
AACAAGAAGAAGAGAAAATCCTTCCAT-TGCATCG |
| 32 | E. grandis
B-expansin | CTGACGCCTAACATGTACCTTAACTG-TAATGTAG
CAGCGCAGGTCGTCATAGCAGAGGCCG-GTCATGC
TGGTCAGGTAGTTACTTTAAAAATCTG-GAAAGCT
TCTTTGTTGTTGTCTTTGCTGCTTTCT-TCGCTC
TTTCGGCGAACTTCCCAGTCGAT-TCATCGGTCTA
AAGAATAGACACGGAGGTTATCG-CAAACTTATGC
AGAGATTCCTTGCGGTACGCAAATGCAT-GTTTAA
TAGATCATTATGTTAAATAGATAATAT-AGTGACT
TTCAGGATCCGTTTGTTTTG-CAAATTTTTTTTCC
TAAAATTGGTAACATGCAACGCT-TGAAATTATCA
ATTAGCGAAAATATTATTATCATA-GAGAACAAT
TTATATAAACCTTCTCCCAGC-CTAATAAGCATGC
CTGGTTCTCTAATATCAAAGAAAAAGAG-GAGCTA
GATCTCGCCTTTAGAATGATTTGAAG-TAATTGCA
GTTAGCTTGAAGACATTCGTAGATGTC-GATTGAT
CAATGCTTTTGGAAGTACTAGAGATGCG-CACGCA
TACGTGCGATATCCAAACTATTTCCGT-TGACCCT
CACGAAAATCTCCGTACAGACCGTTGT-TGCTAAT
TCTTTATTTGCCGTAAAATCTGCAT-GAATCCATA
AATTCAATGATTCGAACGTGACGCAGAG-GAAGTT
ATGCATTCCAAAAGATAGCATTTATTT-TAAATAA
AGAAGTGAAGATTACAATATCTTAGGT-GCCTATT
TATAGAGAGGTCGTCATCTA-GAAAATAACCAAGT
AACCGAAATTGAATAACAAAT-TAAAAAATATAT
ATTGATAAAAAGGGAAAGTTAT-CAAAATACAACT
AGAAAATCTCCAAAATGT-GTTTGAAATCTGTGAT
ATCTCGGATTTGTGGGATCGCTTGCTCT-CATGAC
GCTCTAATGTTTCCATAAAG-GCATTTGCGGAGAT |

TABLE 6-continued

| SEQ ID NO | Gene Homology | Sequence |
|---|---|---|
| | | TATTGTGTCGGATTATTCAGCTTGCAA-GAAAAGT |
| | | TATAGTGCGAGCAAACCATATAAAATAA-CAATAA |
| | | ATAATGGCAAAACTATCGCCGAAAAT-TCTCCAA |
| | | TGACGACAAGGACTCCGATTTAGTG-GAATTTTGT |
| | | GCTGTCAATTTGACTATAAATACCCGC-CCGTTGT |
| | | GCTCCCAAATCGAGTGCAAGAAAT-GAAACTCCTG |
| | | ACCAA |
| 33 | E. grandis Putative Laccase | GTGAAGAGCCATATTTTCATTACAT-AAAGGCATT |
| | | TTTTTTTTTAATTTTTAATAGGTGGTC-CGACCGA |
| | | CAAGATATTATTATTTTTCTATTTGCAT-GAAGAA |
| | | GAAAAAGATTGGTTTTGACCACAATG-GTTTGTCC |
| | | TCTCGTTACCCATTTTATATTTG-GCAAGTTTGGT |
| | | GATTGATTGTAGAAGAAACACGAAACA-CACGAGC |
| | | AAAAGTAAAGGACTCCAAACCCAAATTT-TAATCC |
| | | ACAAATGAATTTACCCACAT-AAAAAAAGGGGAGA |
| | | TTATGATTAAATTCGTTGAATAATGC-GACCCTTT |
| | | AGGAGAAGGCTTATTAAGCAAGCATC-GACGAAG |
| | | CTACACACTCCTTTTGGGAGAG-GCTAGTGGGTG |
| | | CAACAACTACGATTCGGGTA-GAGCTAAGCTTTGT |
| | | CCCCAGTGGCGGTACTGCCATGAC-CAGGGCTCTA |
| | | AATCAAAACCTAATCTGCCAACCT-CAAAACAAAC |
| | | GCTGTCTCGCCCCCCCCGGCTGCGC-TATATAATG |
| | | CAGCCGATGGCGTCCTTCCTTTCTC-GAACCCTAA |
| | | GCAGATCAAGAGTTTGAGT |
| 34 | E. grandis Euc unkown protein | AAATTTTTTTTTTTTTGGGTGGGTAG-TAGGAT |
| | | CTGTCAGAGTAAAGTGACTTAACGC-CAATTCTCG |
| | | ACATTTCAGACTAATAAAATATTTACA-GATGCAA |
| | | CGTCTCACTCTCTCCTTGCAAAACCA-GAAAGGGA |
| | | CAGCAAGCAAGAAGAGGGGAAGAGAA-GACTTGC |
| | | GTTTTAAGCAAGGGGAGTGCT-GACTTTTCAAGCG |
| | | ACTTAATTAATCTGTTTAGCAC-CCACTTTGGTTC |
| | | GTTTGATCTTCTCGTGATTTATTATT-TACCTATG |
| | | TACAGCTGCGGTTGAAATGGC-CTCTCTCGCTTAA |
| | | ATGGTAGTTTGTCCTTTTCTTGGGGTG-GTTGCTT |
| | | TGGAAATATTCTTTTAGAAG-CAGGGGCAAAGAAA |
| | | TGGAGTGGCATCTGATGCTTCTTCAA-CACTTTGC |
| | | AGCCATATCGAGAATATATACCTA-GAGAGAGAGA |
| | | GAGAGAGAGAGAGAGAGGAGCAGTG-GAGAAGA |
| | | AGGAGAAGAAGAAAAGGGTCAGATCA-GATCCAGT |
| | | TGTTGGGAGCAAGT |
| 35 | E. grandis | ATCATTAATATCATTAGAAAGATATAT-TACATTT |
| | Euc unkown protein | TAAAGATGAATAAACATTTGAAAT-GTTTTCTCTA |
| | | CAACTAAAAAAAAAATCATTGCCTCTA-CAACTAA |
| | | AAAAAAGATCATTGCCCATTATGA-CATTTCATTT |
| | | TTTTTCTAATCACATCAAATTACTTTA-GAATAAC |
| | | TATCCAGCTGCCAAAAAAAATAGTAT-TGTATAT |
| | | CTAAAATAAATATATTGACAAATGC-CAACTAAAT |
| | | TAGGTATCAACGAATACCTCTTACTTTC-CTACAA |
| | | TCGAAGATGTAAAGACTAATGTA-CATTTCTTCAT |
| | | GATTATGTACTAATCGATTACAAAAAC-CAACATT |
| | | TTTTTTTAGTTCTTGAATTTCTTTTATT-TAGGAA |
| | | CAGTATCCACCAAATATGTTCTT-TAGCTAAAGAA |
| | | TGATATATATTATTTTTAAAATTGCGAT-TGGATT |
| | | CTTCATATGTTATATCTTGTTCAAATAT-TATTAT |
| | | TTTGATTTGATTTTCAAAATAAAACA-GAAAATA |
| | | AATCTCATCTCGTTCCTTTTTTCAAT-AGTGAAAA |
| | | TCCCACCAAATTCATTGACAAAAAAT-CATGAAAA |
| | | CAGTAAAGCTTGTATTTTCATTC-CCAACTTTAAA |
| | | ACTGGTGGGTGACATTCCAAATGAT-CATATGGTC |
| | | ATATACTAATTTTCCCAATTTCT-GAGCGTGCTCA |
| | | ACGTGATTGTACCCTTTTATTTTCGGAT-CATGCC |
| | | AGGTCAATAGAGAAAATTTATCAAA-GATTAGTTT |
| | | AATGATGAATTGGGACCAACCTCT-CAAGTCCATG |
| | | AAACTGCCGTATGCGCAACCGTAAGCTC-CGTTCC |
| | | AATTTTTCTAATGATTCAAG-GAAAAATAAATAAA |
| | | TAAAAAGTCCATCGTCGATGTGA-CATTTCGCCT |
| | | GCGCTCTCCAGCTACTTAATCAAT-CAATATATAC |
| | | GAATTATTTAGCACATGACAG-CATTTTTCCCTTT |
| | | TTCCTGGCGTCCTCCTAGGGTGGATCCG-GACCGT |
| | | GGATCGAACTACAGGAGTG-GCGGGGCTCTCCGCC |
| | | ACCGACAGCAAAGTCAATATCAATCATC-GATGGC |
| | | AGTCGCTTTCCGGACGATTCATACT-CATCCGAGT |
| | | CCATTTCCCACTTCAACCTCAAGTC-CCTCCTCGT |
| | | CCACAAATGTAAAAATGAAAAAATG-GAGGGCAGA |
| | | TTAGACTGAATTTTAGCTGTACAACA-CATGTTGC |
| | | CTGTGCTTCACGTTCAAGATCCACGGT-TGCTTTG |
| | | CTGTTGCACTCGCACCAACTGTACT-GAATCTCCC |
| | | TTTATTTCTCTCTTT-TAATTTTTTTTTTTGGG |
| | | TGGGTAGTAGGATCTGTCAGAGTAAAGT-GACTTA |
| | | ACGCCAATTCTCGACATTTCAGAC-TAATAAAATA |
| | | TTTACAGATGCAACGTCTCACTCTCTC-CTTGCAA |
| | | AACCAGAAAGGGACAGCAAGCAAGAA-GAGGGGGA |

TABLE 6-continued

| SEQ ID NO | Gene Homology | Sequence |
|---|---|---|
| | | AGAGAAGACTTGCGTTTTAAGCAAGGG-GAGTGCT |
| | | GACTTTTCAAGCGACTTAATTAATCT-GTTTAGCA |
| | | CCCACTTTGCTTCGTTTGATCTTCTCGT-GATTTA |
| | | TTATTTACCTATGTACAGCTGCGGT-TGAAATGGC |
| | | CTCTCTCGCTTAAATGGTAGTTTGTC-CTTTTCTT |
| | | GGGGTGGTTGCTTTGAAATATTCTTT-TAGAAGC |
| | | AGGGGCAAAGAAATGGAGTGGCGTCT-GATGCTTC |
| | | TTCAACACTTTGCAGCCATATC-GAGAATATATAC |
| | | CTA-GAGAGAGAGAGAGAGAGAGAGAGAGGA |
| | | GCAGTGGAGAAGAAGGAGAAGAA-GAAAAGGGTCA |
| | | GATCAGATCCAGTTGTTGGGAGCAAGT |
| 36 | E. grandis Euc Csl-9314 | AAACTCATACTCTTGATAAGATGCAGA-CATTGCT |
| | | GGCGTTCAACAAGGAAAAGAAAAAGAAG-GAATAA |
| | | GACAAAGTGAAAGAGAAAAG-GAAAAAAAAGTA |
| | | AAGTAAAATAAATATCATTAAAAATTGTG-TATGTT |
| | | AGGGTTGTTAGGCATTTATGTCCGCAC-CAATTGA |
| | | CGCATTTATGTCCGCACCAATCGAAC-CATTTATG |
| | | TTCGCACCAATCGACGCATTTATGTCTG-CACCAC |
| | | TCATCTGCACCAATTGGCCAAAATTGGC-CAGAAT |
| | | GATTGAATTGACATAATTG-CAAAAATATCTAAGAC |
| | | TGAACAAGCAAAAAAAAAAGTTATGAC-CGAATTA |
| | | GAAATTACAATAGATTTAT-GACTTTTTTTGTAAT |
| | | TCCCCCCACCTAACTCTGTCAAACCT-GCTAATAT |
| | | AGACTAATTCATTCATATATT-TATATATACACAC |
| | | TCATAGGTTGATATATGAATATGGGG-TACGTAT |
| | | AACCCTATGTGCTAAAATCTTG-GAGAACTTCCTA |
| | | TTCATATCAGAAGAAGAACCGATCCTGT |
| 37 | E. grandis Euc CAD | AAAACAGATTGTTTTAGAT-TGATAACGTTTTCCT |
| | | ATCATGCCGGCATCATCT-CAATTTTGAATTATAT |
| | | CGGAGCATTAAATATAAAAGTTAGGT-TACGGATG |
| | | AATGATAACGCAGACCTAGT-GAGAAAATTAGTAT |
| | | AATCACGATAAAAATATCCATATAGA-CATCACAA |
| | | AAATGCCGCCCGATCTGATGAAATCCGA-CAAATA |
| | | ACACAAACATATATATGTCCAAGACTTG-GACTTC |
| | | AAGTCGACATGCTTGTGCATGCA-CAATTTTGGGC |
| | | CATAAAAATTGGGCATGTGAGAACCT-CAAACCGTT |
| | | AAGAGATCAGGTATTTACTTTGTTTGTC-GACTGA |
| | | CGAGACGTGCACGCATTTCACACCCTCT-TCTCAT |
| | | TGATCTTCAAAGCTTTTCCGAACTCAC-GATGTT |
| | | CCAGAAAGGCGATGTTTTGCTGACA-GAGGGAGCG |
| | | TTCGATGGAGCTTCTCCATCACT-TAATTTGTCCC |
| | | TTCAAGATGAAAAAAGTAAGAGGTCCAC-CGTACC |
| | | AAAACATTCTTCCACCCAGAAGAAAAC-CACAGTA |
| | | GCTGGAGGGAGTCAAGCATGTCAGAAG-CACAGAA |
| | | ACTGGGAATGGCTAAAAAGCAAGTCT-TGACCCTT |
| | | AACCCACCCCACTGGTTCACCTACCG-CACCTCGG |
| | | GTTAGGTATTGCTTGCTGAGGTGT-CACTTTTCGC |
| | | CAAAGTCATGTCTCTCTTTTGGAATCT-TCTTATT |
| | | GGTCCGTCTCGTTTCCTCGTTGCTGGAT-GCTGGT |
| | | AGCGTTTTTGTCCATATATATATG-CAGTCCATAT |
| | | GTATCCCCGTCACTCCTCATCTATGCTC-CTACCC |
| | | GGCAACTTCCCACTACGATAAGCAG-CAAGTTTTC |
| | | GGCTCTGT |
| 38 | E. grandis Euc CAD | ATCAGGTATTTACTTTGTTTGTCGACT-GACGAGA |
| | | CGTGCACGCATTTCACACCCTCTTCT-CATTGATC |
| | | TTCAAAGCTTTTCCGAACTCACGATGGT-TCCAGA |
| | | AAGGCGATGTTTTGCTGACAGAGG-GAGCGTTCGA |
| | | TGGAGCTTCTCCATCACTTAATTTGTC-CCTTCAA |
| | | GATGAAAAAGTAAGAGGTCCACCGTAC-CAAAAC |
| | | ATTCTTCCACCCAGAAGAAAACCACAG-TAGCTGG |
| | | AGGGAGTCAAGCATGTCAGAAGCACA-GAAACTGG |
| | | GAATGGCTAAAAAGCAAGTCTTGACCCT-TAACCC |
| | | ACCCCACTGGTTCACCTACCGCAC-CTCGGGTTAG |
| | | GTATTGCTTGCTGAGGTGT-CACTTTTCGCCAAAG |
| | | TCATGTCTCTCTTTTGGAATCTTCTTAT-TGGTCC |
| | | GTCTCGTTTCCTCGTTGCTGGATGCTGG-TAGCGT |
| | | TTTTGTCCATATATATATGCAGTC-CATATGTATC |
| | | CCCGTCACTCCTCATCTATGCTCCTAC-CCGGCAA |
| | | CTTCCCACTACGATAAGCAG-CAAGTTTTCGGCTC |
| | | TGT |
| 39 | E. grandis Euc LIM | AAACACTTTCTGTAAACTTATTTTTG-CAAACAAT |
| | | CCAAAGCCAAAAAAGTAAAGAAAC-TATTTTCAGA |
| | | TAGGAAATTTTTCTCAAAAACAAG-GATCGTCGATG |
| | | GGACTGGAGCTCTCAGCCCAAAAAA-GAAAAAAAG |
| | | AAAGGTAATGTGATGTAAGAGAGAG-GAAAGTAAA |
| | | GTTGAAGAACGTGTATGCAAAGCGACAT-GATGGG |
| | | GGAGAGCATTTGATGGACAATCAT-TGGGCCAACT |
| | | CACATGAAGTCCTTACAACAAACAGTTG-GAGGAC |
| | | GATGCAGCTCCAGCTCGATTCAGC-GACTCCAATT |
| | | ATATTTCCCTCTCTGGTCCTCTCCTC-CTTTCCAT |
| | | GCGCAATCCAGCTAAGTTTCTATTC-CATGGCCCC |
| | | TTTGCTACTAGGGTCACATCTGCCA-GATATTTTT |

TABLE 6-continued

| SEQ ID NO | Gene Homology | Sequence |
|---|---|---|
| | | CTGGTATGCAGCTAAAAGCATAGTAGT-GCCCTTT GGAAAAGTTGATCATAGTAACTGGGCTG-GTCCAG TTTAATTAGAGCAATCTATGATGAAAT-TACTAAT GAATTTTTGGGAAGTTCGGTTTTTG-GTTTCTCGG AATTTCTCACCAATATCATTGCT-TCAATATTAGT TAAAATAGACGACTGAAAAGATCAT-GATAGATAA AAAAAAGGGAGTGGCCAAAT-TATTTTTCTCTAAT TCTTACTTAACTTAAGCTTCATGCAT-GCTGCCCA TCTTGTGTTTGGTCATTAACTAACCTA-GAAGGAG GGGGGGAAAAGGTAAAACATGTCAT-AAAAGGTTT AGTTAGACCCTTCACCCAAAATGATTGC-CAATG CCACCACTTTAATCATCAACTTTCCAAC-CAACAC TTGTTTTTTTGGCTTCCCTTTCTTATC-CTCCATT CTCCTCTCTCCT |
| 40 | E. grandis Euc 4CL | ATCAATGAGTGAAAGGGGCGGCACAA-GAGAGAT ATACTTACACATGCTCCCCCTAGACTA-GACGACA GACGCAATTTACACATGTCCGAGACAT-ACGGTCA TGAAATGGGAATTCTGATGTAGAAATAG-CATGAA CCCATTTAGCAAAGAAT-TGAGAACTGGGCCGGAA CTCTGCTCGTGTTAACTAATC-CAAGCGTCGGTCA AGCTGTGCGCACGCATGGGTGG-GAAGGGGGCGGG GGTAGGTGCACAGGGAATTTG-GTTTGGGGGTTAG AGTTGGTCAAAAGCCGAAACGGTGTTAG-GCATTG GGCTTTTTGGCTTTCGGCTTCAAGA-CAATTTGAA GGGGAGATGGGGCGTGCCATCTGCTCTC-CCCCTG CCATATGACCCATCATCCCCTCTC-CATCTCCATC TACCTCTACCTACCCCCGCCCCCTTC-CTCTTCTT CTCCTTTTCTCTTTCCTTCTTC-GAAAAATTTTAA TTTATTAAAATATTTATTGCCCCTC-CCCCTCCCC CTCTCCAAAACCGAATTTAACCCAAC-CCTCTCTC TTTCCCTCCACCCAAATCTCTACACAT-CATCATC ATCATCATCATCATCTCCTCCCCTCCCTTTTCT |
| 41 | E. grandis Euc CAD | AAAATCACTTAACGGCTTCAC-CCAATATACTAGT TATCTCATAAGTG-GCAATCTAAAAAAAAAAACAC TATAGTTACGTCGATGAAAGGTCCGACT-TATCTG TTCGAAATCAGAACCTGAATTTCTAT-TATTGATC TAAACAAATCACGTCGAGTGT-GATCTAGTTTATG AAAATACTACAAAGAAAT-GAAAAAAAAAATGTT AAATTGAATGCAATTTATTAG-CAATGGGTTTGAA AATTAGTAATAGTATATCTATTGTCATG-CAAGAT ATGAATATTTTAGATCCTTCTAGAAG-CACGGATA |
| | | ACTTATGACTCGATGTTTTCT-TAAATCTTTGGAC ACTTGTCATTTTTTCATAGAAGCGAC-GAGAAG ATCTTTCGCGGCTGTTTCACCTAC-CCCAACCTTT GTCCCTATGCATCTTGGCTGAGATGT-CAACCTTA GGCTTCCGACACCTTTGACTCTCTC-CTCCATC GTCCTCATCTCTCTCCTGTATA |
| 42 | P. radiata Cinnamoyl-CoA reductase | AAAAAAGTTTCCCAATCTCTAAGCAAC-CATAAAG CTCAACCACTCTCTGTCCTGTGC-CCCAACGTCTA CCAGACGATTAGGTATGCACTGCAGT-TCTTCGTC TGTCATGCTACCAGACAGTTAGGTAAC-CACTAAT GTCTTAGGTGGTGATTGATATTGAT-GTTTCTTCT GCAAACATGTGAATCAATGTG-TATCGCTGGAATA TGACACTGTGGATCACTGGATATACATA-GAGAGA TCTGCTCTGTCCATTTTTAACAGAT-TCATCTCAA TTTTCTTGTTCCAATGTCAACATTTTCT-CAACTG CTCTGCCCCATCTTTATTAAAAGGGAA-CATCTAC CCTGCATTTCCACACTCCAATC |
| 43 | P. radiata Cinnamoyl-CoA reductase | CCTATAAAAAAGATTTTATTAAGAG-CATTTGGA AAACTATCATCTTTCCAGGACCAT-AAAACTATTT AATAGTTCAATAAAGATGAAGTAGTTAC-TATTTA ATAGTTTAATAAAAATTAAGTAGTCTAA-CAGTTA TATAGTTATATATATGTGTGT-GTTTTGGGTATGT TTTCAGGTTGAATGATGTATAATTGAG-TAAGGAT TTTTTTTGGAATTAGT-GAATTTTTTTTTTCAGA ATAACAATTCTATATATATCAT-AAAAATAAATTT TAAATAAAAAAAATCTAAATAAAAAT-TATTTAAA AAAACACTAAAACCATTAGTATACCAA-CACTTCA ATTTAATGATG-GATAAAATAATAAGCTAGCTCTG CTTAACATTACACTGGTGAGTTTGA-CATGAAA AAATAGATCTCTGCTTTCAGAAGTACG-CATTTTT AAATTTAAAAAAGTTTC-CCAATCTCTAAGCAACC ATAAAGCTCAACCACTCTCTGTCCTGT-GCCCCAA CGTCTACCAGACGATTAGGTATGCACTG-CAGTTC TTCGTCTGTCATGCTACCAGACAGTTAG-GTAACC ACTAATGTCTTAGGTGGTGATTGATAT-TGATGTT TCTTCTGCAAACATGTGAATCAATGTG-TATCGCT GGAATATGACACTGTGGATCACTG-GATATACATA GAGAGATCTGCTCTGTCCATTTTTAACA-GATTCA TCTCAATTTTCTTGTTCCAATGTCAA-CATTTTCT CAACTGCTCTGCCCCATCTTTAT-TAAAAGGGAAC ATCTACCCTGCATTTCCACACTCCAATC |

TABLE 6-continued

| SEQ ID NO | Gene Homology | Sequence |
|---|---|---|
| 44 | P. radiata Phenylalanine ammonia-lyase | AAAACTAATTTTCAAAATATGAG-GAAAAAAGCGA<br>GACCACGAAAAAATCATTGAAAAAGAC-CTTGCAA<br>AATTCAGGACGACCACGAAAAAATCAT-TGAAAAA<br>GACCTTGCAAAATTCAGGACTTGCTCT-CACCAAC<br>CTCGCCAGGACTTTGACCGTGCTCAT-GCTTGTGT<br>CATGCTTGCATATCTATACGTGTCA-CATCGACCG<br>TCCGATCTATCATGAAAAGAACGGTCAT-GATGAA<br>ATCTCAACTAAACCCACTGCGT-TAAATTTTCGAA<br>CAGTGAGAAAGTAATCGTATAAATAC-CCCTAAGC<br>TCTTAGACCGAGAACGCATGCAGCAT-TCGGCTCT<br>CATTCTGAGGTTCATCTGGCT-GAAGTTTGAACTG<br>TGCT |
| 45 | P. radiata Phenylalanine ammonia-lyase | ATCATCACCAGTGCCACCTAA-GAACGCGTTTGTA<br>TTGAGATACCATCTATTTTTTCGGATG-CAATTAC<br>TAGTTAATAATTTATAACATTATT-AGGGGTGGGG<br>TCCAGAAAAATGAAAAAAGAAAAA-GAAAATTGAA<br>ATTTTAAAACTAATTTTCAAAATATGAG-GAAAAA<br>AGCGAGACCACGAAAAAATCAT-TGAAAAGACCT<br>TGCAAAATTCAGGACTTGCTCTCAC-CAACCTCGC<br>CAGGACTTTGACCGTGCTCATGCTTGT-GTCATGC<br>TTGCATATCTATACGTGTCACATCGAC-CGTCCGA<br>TCTATCATGAAAAGAACGGTCATGAT-GAAATCTC<br>AACTAAACCCACTGCGTTAAATTTTC-GAACAGTG<br>AGAAAGTAATCGTATAAATAC-CCCTAAGCTCTTA<br>GACCGAGAACGCATGCAGCATTCG-GCTCTCATTC<br>TGAGGTTCATCTGGCTGAAGTTTGAACT-GTGCTC |
| 46 | P. radiata Laccase | AAAGATGCTACAATTTGATTTCTTTT-TAGTTAAA<br>TTTAATCAGAAATATAGAAAAAGGTTAG-GAAGAT<br>GTTTGCAGTCGTAAATATGAGCGCAATG-GCCTTT<br>AGTCCACGCGTAGTGGCACATCTTA-CACGGATAC<br>TTGGTTTTCAGCCCCACACAACTG-CAAGGGTTGC<br>TTCGAAGGTAACTCTTACGTTG-GTTTGAGTGCCC<br>AAAACATATTAGCTTTTTATTTTGTGT-CACTGTC<br>GACATCGTTGGCCCTAATTTTATCGTAT-GATCAG<br>GCCCTGATCTCTCTCGCCACCATTTCCT-TATAAG<br>GCGCCAGCAGACAAGCACAGCTCTG-GAAGGAACA<br>TGGGTGAGTGACATTAAAGCAACGCGAT-GACCTC<br>ATACCAGCTTCAACAGCTTACACCATAA-GACACG<br>CTTTCCCATGGACATCCTCCTACGTAT-CACTCAC<br>TTGCCTATATATTCATGCAACTCCGTCA-CAGTTT<br>TATAATAATTCAGGTGCCTTTTATAT-CAGTAGTA<br>TCAACGGATACACCCAGGGTGATTGT |
| 47 | P. radiata Cellulose Synthase | AAATTCATGTTTGTCATAGGTTATGG-TATTTTGC<br>ACACATGAAACAAATTTTACAAT-TGACTTTGATT<br>AAGATATTAAATCTACAATAGGTTAT-CAACTCCA<br>CGTGATAATGAAGTAAAAAGACTGGATG-GCTAAG<br>TCAATAAAACAACCAAATAATCAAG-CAATGATAG<br>CTTCTATCAAATAAGGATGGTTCAGCTA-GATCCA<br>GGCGAAATATGATTCAGCCAGATAC-GAAAAGGCG<br>AGCGGTTGAAATGTTTGAAT-GTTTGCGGGGTCCC<br>TGGTTGCTTCGGAGGTTATTCTACG-TAATTTATT<br>CGTTATACCTTGCCTTCTAAGCATCG-CAAACTGT<br>GATTTCTTAACAAACTCGATGCATGCGC-CATAAC<br>CAACAAAACCATTTAGTTGAGTTTACG-GTCTTCA<br>CAATTCATGCTCAGTCACCTTCAACTAT-TATGAC<br>AGATTAGGTGCTACTTATTCTCTCGT-TACCCTTT<br>AGAGTGAACTTTAATCCAAATTGTCAG-GTGATTT<br>GGGCCCCCAGGCGATGGATCCAGCGA-CAGGGGAA<br>CGCAAGTTTGGTGGTTGTGGCAGTG-CAGTTGGTA<br>TGCCCCAGAGAGTTTTAAGACTTCA-GATTTGTGT<br>TCAGTATCAGGAGCTGCTATGGAAAAG-CAACCA<br>TATAAAACTATTGCCATTCGCACAGGAA-CAGAAC |
| 48 | P. radiata LIM | CCTTTGGGAATGAACTTTGAGACCAC-CTCCAACC<br>AAGATATTAAATCAAACATCCCACCAT-ACCATGG<br>CATTCGGAAAAAAGCTAGGCTAAGCT-GAAAATCA<br>CTGTCATAACCCAGTAAGACCATGCCAC-TAATAG<br>CAAGAGAACCATACACCAACATG-CAAAGCCATGC<br>ATGTCCAAACCAGCTAGGAAATCACA-CATGCAAA<br>GGGTTACCTGCAAGTATTCCTGT-TGAAGTTGCTT<br>GATCCTACTTTCTTTTCCTTGAGCCT-TGCTTGCC<br>TTCCTTTCCTTTGCTTGATTTTCCTTTC-CTTGCT<br>CCAAACTAGAGTGCTCTAA-GAAAACTCTAAGTGA<br>CCAAGAGAGT-GAGAGAGAGAGAGAATAATGAGAG<br>TCCAAACATGAACTTGACAAAAGCCAT-GAACTGA<br>TCCTCAGAAGTCATTTTATGCACGAG-GCTTCTAT<br>TTTCTTCATTTTCCATCATTTTCCT-TCAATTTCC<br>TCATCACATGCAACGTGCGACTTTTCAC-CCCGTT<br>TTCCTCCTAATTTCTTTTATTTTCAT-AAATAAAT<br>GTGCCAAAAATGCCTcTTGCCTTAGC-CTTTGCCA<br>GTTTCCTTAGCCAAAACACACATCCAAT-GATGCC |

TABLE 6-continued

| SEQ ID NO | Gene Homology | Sequence |
|---|---|---|
| | | CACTAGGATATCTTTGCCCAACAT-TAAGCCTGGA |
| | | ATAAATGTCTCTTAATCGTGGTCT-TATTTTGCTT |
| | | TTATTAACTTTTATTACAT-GAACTTTTCACTAAA |
| | | GCTATTACAAAGATATATTTATTATG-GCAATTAT |
| | | GTTTGATTTTGAAGAGCTAGTAACTTT-TAGTTT |
| | | ATTATGGCCTTTTCCGTAAACT-TATTTTCTTGAA |
| | | AATCTCTATAAATCCAATGAAAAATT-TATAGAAT |
| | | ATATGTTGTGTTTTCTTCACTAC-CTCTAATAAAT |
| | | TTTTTACTTAGTAATCTACAAAGCCATT-TATTAA |
| | | AAAATTCAAGTTAATTAAAAATTAATAT-CATTTC |
| | | AAAAGTCTTTTTAATATAGTCAAAGTT-TATTAAA |
| | | TTCTATGATGTATATTTCTTT-TAAATAAATGAAG |
| | | AATCCATTTTTTTACTTAAAAC-CATATATTTTTT |
| | | ATAACGTTGATAAATAGCATGCATT-TATATAAAC |
| | | AAATATATATTTTTATAACGTTAA-GAGATTGTTA |
| | | AAACTTTTAAATAATTAATATTTTATT-TATTGTT |
| | | TTGAAAATGTCATGATTTCCACCTAC-CTCGCCCA |
| | | TCAAATCTTGCTGCAAACCAGGCTTAC-CCAACCC |
| | | CACACCCACAATATATTTTTGGGATCTG-GTGCCC |
| | | CCACCTTTGATCACAGTGAACACCAT-AAAGACAA |
| | | ATTATAAAGGCAAGGGGACTTGGCAC-CCATGAGG |
| | | CAACCGAAAGCAACAAATCATTTTTTC-CAAAGA |
| | | GATGAGTGTATGCCAACGAAGAAACAC-GATGAAC |
| | | CCCACGTGTCATTGGCCAACTC-CCACTTTCGACAA |
| | | AAAGAAGGAAATTAGAATTAAAAAGGC-GAATAAA |
| | | AATTGAAAGGCCATTTAAAATAGAAG-GAAGAATA |
| | | GCCTATATGGTAGATTTAAAT-GCTTTTTTGAAAT |
| | | CCGGTTACTCGCAAGATTATCAATCGG-GACTGTA |
| | | GCCGAAGCTT |
| 49 | P. radiata Expansin | AAATTAGTCAAATCCAAAGCAGACAACT-TGGGCT |
| | | CTCACCTAAATTAACACATATACCCTAC-CAGCTT |
| | | CCATAGTTTCCAACTTC-CTTTCAATAAATCTATT |
| | | CAAAAGCATGAAAAGCATGACTAAGGT-TCAATTC |
| | | CCAAGTTATGGACACCCACCTGCTCTAG-GCATAT |
| | | AGGAAATCACAATCCAACTAACGAC-CAACTACCC |
| | | AAAACTTTGAAGAAAATGAGTAAA-GACTCCCCCA |
| | | GTGATATTATAATTATATGGTCTCTCTA-GAACCC |
| | | TTTATTGCCCCTTCCAGTGTTATATT-TAGTTCCC |
| | | CATTTATATATCCCTTGACTTATGAAAC-CATTTA |
| | | GGTGCATTAACATAGTCCTTGACTAA-CAAAAAAA |
| | | TTATTTAGGTGCAGTAGATACGGAAAG-TAACCAA |
| | | TGATGCTAAGAAACTGTGCACGTACTT-TAATGGA |
| | | GGTATTACTTTTATTATGGTTGGTTTG-GATACAT |
| | | TCATAATGGAAGCATGTGCTCT-TCATCGTTAAAG |
| | | TTGTGGTGGGCATTCCCCATTTTCCAC-GAGAAA |
| | | CCGAATCCCGGCGTGGAGACGACGAC-GAAATCGA |
| | | TGGATATTCGGTGGAAAATTCACAG-TAAAATTCC |
| | | TGGAGAAAAAGGTTGCCGAGGTAGT-TGAAATCCA |
| | | AACCGCCGAAATGAGCTGGAAACCCGC-CTTCTGT |
| | | CAGTTAGTTGAGTCATGACTGCAGCT-GTCTCAGG |
| | | TCTTACACTGTAAAGGCACCTTAATGAG-GCATTC |
| | | ATTCTGGCAGTCTGGCTACGGAACT-TAATAGTAC |
| | | TTGTTATTCCTGCCCCAATATCTATT-TAATAGGC |
| | | ATCCCCCCTCACTACTTCTTGCCCA-CAATCCCTC |
| | | CATAGTCCTGAGCTTGAGACCATTTTTCTGC |
| 50 | P. radiata 4CL3 | AAATATAACATAATCTAACTATTGATG-TACATTA |
| | | TTCGCCTATAACAAAATCTAAGTAT-TGATGTCAC |
| | | ATTATTGGCATATAACAAAATCTTTAG-GATAACC |
| | | CCTTAGTCAAGCTCTTGTACTTTCAT-GTTTATTA |
| | | ACCAATAAATCAAGCTGATATGGAATAG-CAGACG |
| | | TACGTGGTAATAATAAATGGAGTGTAA-GAGTTCG |
| | | AACATTTTAATTCGGAGGGGCAGCTTAT-GTGGAA |
| | | TATCAGGCAATCATACAAGCT-TGCTTTTGGGTAA |
| | | TAAAGACCCCACATGTGGTAATAA-CAAGTGGATTT |
| | | TAACAAACCAACATTTTGATAGGGAG-GATAGGTG |
| | | GCCTGGTAAGTTAGAATGTGCTAGTCAT-GCCTTT |
| | | GAAAGAAGTTAGTTGTGGAAGTCAAA-CATGTTCC |
| | | CCACACAACACACCTCACCACACAAAAT-GCTGGT |
| | | AGGTCATGTGATTGATGGATGGGCATGT-GTATCC |
| | | TCCAAAAAAATGAATATACACAC-TAAATATTCT |
| | | ATTGACATAATATACAAAGAAGATTAG-GTCTATG |
| | | GAAGAAGGGAAGGCGAAGGGAAGAT-TGGGTCGT |
| | | GGGGAAGATTGGGTCGTGTCCTGCTAG-CACGTTG |
| | | AATACCTACACGCCATTTCACATCTAC-CCATCAA |
| | | CGTCAAATAGAGCATCCAAAT-CAGGGCGTGGTGG |
| | | TGTGAGGGGAGAGTGAGGAGAAGAAGT-TGAAAAA |
| | | TTCTGGCTGAAAATCCACCTAACA-CACGCTCACC |
| | | AGCCCCTCAACGAGGGGCACCAATTAT-GAATAAT |
| | | AATAGCTAGAACAGAGCAGCAGAAGCA-GAGTTTA |
| | | TATCTATCCATTGTCGTCTGTAAAT-TACTCTGTG |
| | | AGTGTTTAGTGTTTTCTTCTCTTAT-TGATTTCAG |
| | | GGGACAAGTAGGTGGG |

TABLE 6-continued

| SEQ ID NO | Gene Homology | Sequence |
|---|---|---|
| 51 | P. radiata 4CL1 or 2 | AAACACCAATTTAATGGGATTTCA-GATTTGTATC<br>CCATGCTATTGACTAAGCCATTTTTC-CTATTGTA<br>ATCTAACCAATTCCAATTTCCACCCTG-GTGTGAA<br>CTGACTGACAAATGCGGCCCGAAAA-CAGCGAATG<br>AAATGTCTGGGTGATCGGTCAAA-CAAGCGGTGGG<br>CGAGAGAACGCGGGTGTTGGCCTAGC-CGGGATGG<br>GGGTAGGTAGACGGCGTATTACCGGC-GAGTTGTC<br>CGAATGGAGTTTTCGGGGTAGGTAG-TAACGTAGA<br>CGTCAATGGAAAAAGTCATAATCTCCGT-CAAAAA<br>TCCAACCGCTCCTTCACATCGCAGAGT-TGGTGGC<br>CACGGGACCCTCCACCCACTCACT-CAATCGATCG<br>CCTGCCGTGGTTGCCCATTATTCAAC-CATACGCC<br>ACTTGACTCTTCACCAACAATTCCAGGC-CGGCTT<br>TCGAGACAATGTACTGCACAGGAAAATC-CAATAT<br>AAAAGGCCGGCCTCCGCTTCCTTCTCAG-TAGCCC<br>CCAGCTCATTCAATTCTTCCCACTGCAG-GCTACA<br>TTTGTCAGACACGTTTTCCGC-CATTTTTCGCCTG<br>TTTTCTGCGGAGAATTTGATCAGGTT |
| 52 | P. radiata 4CL1 or 2 | ATCTTATGGAGTTTT-TAAATATATATATTTTT<br>TGGGTTGAGTTTACTTAAAATTTG-GAAAAGGTTG<br>GTAAGAACTATAAATTGATTGAGTTGT-GAATGAG<br>TGTTTTATGGATTTTTTAAGATGT-TAAATTTATA<br>TATGTAGTTGTGAAGGAGTGTTTTATG-GATTTTT<br>TAAGATGTTAAATGTGTATATGTAAT-TAAAATTT<br>TATTTTGAATAACAAAAATTATAATTG-GATAAA<br>AAATGTTTTGTTAAATTTAGAG-TAAAAATTTTAA<br>AATCTAAAATAATTAAACACTAT-TATTTTTAAAA<br>AATTTGTTGGTAAATTTTATCTTAAATT-TAGTTA<br>AAATTTAGAAAAAAAAATAATTTTAAT-TATTAAC<br>TTTTGAAGTCAAATATTCCAAAT-GTTTTCCAAAA<br>TATTAAATTCATTTGACATTCAAAATA-CAATTTA<br>AATAACAAAACTTCATGAAATAGAT-TAACCAATT<br>TGTATGAAAACCAAAAATCT-CAAATAAAATTTAA<br>ATTACAAAATATTATTAACATTAT-GATTTCAAGA<br>AAGAGAATAACCAGTTTC-CAATAAAATAAAACCT<br>CATGGCTGGTAATTAAGATCTCATTAAT-TAATTC<br>TTATTTTTTAATTTTTTTACATA-GAAAATATCTT<br>TATATTATATACGAGAAATATAGAATGT-TCTAGT<br>CCAAGGACTATTAATTTC-CAAATAAGTTTCAAAA<br>TCATTACATTAAAACTCATCATGT-CATTTGTGGA<br>TTGGAAATTAGACAAAAGAGAATC-CCAAATATTT | 
| | | CTCTCAATCTCCCAAAATAAACCTAAT-TAATATA<br>GTTCGAACTCCATATTTTTGGGAAT-TGAGAATTT<br>TTCTACCCAATAATATATTTTTTTTATA-CATTTTT<br>AGAGATTTTCCAGACATATTTGCTCTGG-GATTTA<br>TTGGAATGAAGGTTTGAGTAATGAAG-GTTTGAGT<br>TATAAACTTTCAGTAATCCAAGTATCT-TCGGTTT<br>TTGAAGATACTAAATCCAT-TATATAATAAAAACA<br>CATTTTAAACACCAATTTAATGG-GATTTCAGATT<br>TGTATCCCATGCTATTGGCTAAGC-CATTTTTCTT<br>ATTGTAATCTAACCAATTCCAATTTC-CGCCCTGG<br>TGTGAACTGACTGACAAATGCGGC-CCGAAAACAG<br>CGAATGAAATGTCTGGGTGATCGGT-CAAACAAGC<br>GGTGGGCGAGAGAACGCGGGTGTTGGC-CTAGCCG<br>GGATGGGGGTAGGTAGACGGCGTATTAC-CGGCGA<br>GTTGTCCGAATGGAGTTTTCGGGGTAGG-TAGTAA<br>CGTAGACGTCAATGGAAAAAGTCAT-AATCTCCGT<br>CAAAAATCCAACCGCTCCTTCACATCG-CAGAGTT<br>GGTGGCCACGGGACCCTCCACCCACT-CACTCAAT<br>CGATCGCCTGCCGTGGTTGCCCATTAT-TCAACCA<br>TACGCCACTTGACTCTTCACCAACAAT-TCCAGGC<br>CGGCTTTCGAGACAATGTACTGCACAG-GAAAATC<br>CAATATAAAAGGCCGGCCTCCGCTTCCT-TCTCAG<br>TAGCCCCCAGCTCATTCAGTTCTTC-CCACTGCAG<br>GCTACATTTGTCAGACACGTTTTCCGC-CATTTTT<br>CGCCTGTTTCTGCGGAGAATTTGATCAGGTT |
| 53 | P. radiata Pectate Lyase | AAACAGAGCAGATAACACTAAAAAGAC-CAACCCT<br>GTTAGGAGGGGAGAAACAAAAAGATCA-CACTAA<br>AAAGACCAACCCTCTTATCTAAACT-TATTTTCTC<br>TTATCTCTACCCCTTCTATTTTGAAC-CTTTATCA<br>TTTTGATAGAAAATATATGTTAATAAC-CATTAAA<br>CCTACATTGTCAAGCTAGTGTAACT-TATATGTTA<br>ATAACCATTAAACCTACATTGTCAAGT-TAGTGTA<br>ACTCCTTTGGTGGGGTGGTTGTCTTC-CTCTTCA<br>ATCTCATGCTATGACACACTTGTTTTT-TAATAAC<br>ATAGGCCGACAAGTTTGAGCCATTATC-TATCTTG<br>ATTCCTCGAAATGATAAATAGATGTTGT-CAGTGG<br>ACTTGAAAAAACCAAGTAGGGAACAC-CACGTAA<br>TCTTTCAATGGCATTAAAAGC-TACTTTGAAATA<br>TGTAACACTTAGCAATCCTTCCAAG-GCATTAAAC<br>CTACTCTAACCTATGGAACACTTAG-CATCCTTCC<br>CACGGTTGATAATAAATGATTGATTCCT-CAGAAT |

TABLE 6-continued

| SEQ ID NO | Gene Homology | Sequence |
|---|---|---|
| | | AACAAATAAAAAAAAACTATAAAACT-TACTCTAA |
| | | AATATAAAATGAGTATGGAACACGTG-GCAATCCT |
| | | TCCCATGCTCGGCGGTAGCTACTCTCTC-CAGAGA |
| | | TTTGAATAACACAGGCGCCGCAATTAT-GAGAGAG |
| | | CAGTGGAGTTAAGACTTAGTAGCCATG-GTTATTT |
| | | TGAACGCGTGGCAATTCTTCCAAGGT-TGGTAGT |
| | | TACTCTATCCAGAGATTTGAATAACA-CAAATGCT |
| | | GCAGTTATGAGAGAGTAGTAGAGT-TAAGTCTTGT |
| | | CAGCAATGATAGTTACGAACAACCG-TAATTTCTG |
| | | GCTATCTCTGTGTTTATTGGTCGTT-TACTTGCTA |
| | | CAGTGCTCTCACCCCACATGGTAACAGT-GTTCGA |
| | | TGGCCATGATTTCTCCCCACCCCGC-CAAACCTCT |
| | | ACGTTTTTATTCTTTTAATAACTC-CTAATTTAAT |
| | | ATATAAGAGGGGCAAGGTGTTCATACA-GATTCG |
| | | TGCAAACGACCTGAGTTCAGCACAAGTT-TAGTCA |
| | | TTCCATGCGAACTCGACTGGCTCAC-GAGATCCCT |
| | | CGCTGCAGTTATAGATTGCAGGAATT-AGCTTAGC |
| | | AGCATTTCTATCTATGATCTTCTGC-CACTTCTTC CCCTCTC |
| 54 | P. radiata ACC Oxidase | AAGGTTTGCTTGGACCAGCGACACAGG-GAAAAAC |
| | | ATGGCATGCGGGTTTGGATTAAGATGAG-GCCCAA |
| | | TCTTAATTTGATATGTTTGCCAAACCT-TAGGTTG |
| | | TTTTATCTAATTTTTGATTGGATCT-GATCTCTTGA |
| | | TGATTTAAGGGTTTTCCATGTTGACACG-CAATTG |
| | | TAGGTTCCTGGGCACTAAGGTCTACCAT-GTGGCG |
| | | AATTTATCGAGAGTTGACAATTCTGG-TACTGTTA |
| | | GTGATTTGTCACCACTCTACGGTCCCTG-CAGATC |
| | | TCAGATTTTTAATGGCTGCCTTTGAT-TATCTAAA |
| | | GGCTAGCCCCTAATCGCGGCTATGAATG-TATAAA |
| | | GAATGTGTTCCAATGCATTAGAGTACT-CAAAGAC |
| | | ATGTTGAAGGAAAAGGACAAGTCAAGG-GACATGA |
| | | GTAATAACCAAAAAGCACTTGGTCCT-GACCATC |
| | | TGTGTCTGATTCACACTGGGATTCACAT-GTTATT |
| | | TAAGAAAAGTTGCATCAGTGCTGCAAT-CATCAAG |
| | | CCATTCCTAATTTACCACCATGATTA-GATTATTT |
| | | TAATGCAAGAAAACGCCTATATAAG-GAGAGCTGC |
| | | AGGCCCCAAGGTAATGCAGTAAT-CAAACTTGAGG |
| | | AGAGATTTGAGAGTGTTTGTGAAGGG |
| 55 | P. radiata Dirigent | AAACGCTTCATGCCCCAGAAGCCG-CACTCGATGC |
| | | TTTAGAATAAAATGGACCATTACCAGAC-TACGCG |
| | | CCTCCAAAATAACAAAACGTGTATT-AGTTAAAC |
| | | CCTACATAGCACTTAAAGCTTGTCTTAC-TATTAT |
| | | TTTACGTAATTCTGTCTTTTTGACAGTG-GATTGA |
| | | TTGGAACTTCCATTCTCGATACAGTTG-TATGCGT |
| | | TATGTGAACTGAACCAACCTCGGC-CAAAATATGG |
| | | GGAAGATTCACTTCAGAAAAGACAGGA-CAACCAT |
| | | CTCTGATTGTCGACATTAATATCG-GAAAAAATTC |
| | | AGTCAAATGATGTGGAAAGGTTCATC-TACGGAAA |
| | | ATAAAATAGCTCTGAGATGACCCGTTA-CATTTAG |
| | | TGCATAGCATCTTTGTCAACAAGAA-GAAATTTCC |
| | | AGTTGTAGGACTGGTCATCAATGGCCGT-GCCTGC |
| | | AACGCTTTTTCGCAACAGGAAACACG-GACTAAAA |
| | | AACGCGGTCTATCTGTCATTTGACGG-TACGTTTG |
| | | GCACTGAGCCCGAAAAAATCCCATTGG-TAGAATT |
| | | TAGAAGAGGGAGCTTTCACTCGAAAAT-TCTGTAC |
| | | CACAAGCGGTGGCCTCACAATAACAAAT-TATTAT |
| | | ACCCACATGGAAAATGTTAAATCGGACG-TCCGA |
| | | CGGTCGACCAAAGACAAAATTGAT-GAGAAAGTTT |
| | | TGAGGGTGGGTGATAAAG-TAAGCGCGTCTTTTCA |
| | | CAGGCATCTGCATTATAAACCTG-CAACTCCAACT |
| | | TTCATCACAACAAATTTCATTTTCCCCT-TCTCTG AGGC |
| 56 | P. radiata CSL | AAACAACAAAAAATAACAATCTACCTA-GAAATTA |
| | | TATTACCAAATTTCAATTAAAAAAC-CCATTTCTT |
| | | AGATTATTAAACTACACCAT-TATAATTTTCATAA |
| | | TAACTACTAATCACCAT-TATAAATTTCATAATA |
| | | CTATTCATCCCATTATAAATTTCAT-AATAACTTC |
| | | TAATACACCATTATAAATTTCATAATAC-TATTCA |
| | | TCCCAATATGTGCTACCATTTA-GATATTTTGAG |
| | | CCAAAACCCAACCCGAACAAAAATTTG-TAATCTC |
| | | GAGATTAATCACAAAATTTGACTCGAT-TCATATG |
| | | CAAATTGGAATAATTACTCGTCATGGAT-GAGATC |
| | | TTACCGTTGGTGTGATCATGATGACGGC-CAACTT |
| | | TGGCACGCTTCATATCACAAATTGCAA-CAACTAC |
| | | TCTGCTTTTAATGGATGACCATTGAT-GACGACCA |
| | | AGCTTGACACGATTCATATGAGAGAAA-GAACTCA |
| | | AACAATCTACTGCAATGTGAAAAGC-CATGGGCAC |
| | | CGCCAAGATATTTAATTGTCCAACGCG-TAACAAT |
| | | TAGTTACCCCCAATGGGCATTGGACT-TGCCTTTG |
| | | TCTTGATGTCGAAAACAAGGGGG-GATTTCCTCTC |
| | | TTTAAGAAAAATAGAAAAAACAAAAC-CCCTGCAC |
| | | AGCTGGGTTCTCCTTTCTTCAAGCCTG-GTTGGC |

TABLE 6-continued

| SEQ ID NO | Gene Homology | Sequence |
|---|---|---|
| | | TTCAACATAAAGAAACAAAACCCATTC-CATGGTG |
| | | TTGTCTTATTGTGGGTTTGCCTAAT-TCAATGTTA |
| | | TTAGTGGTTGAAACTTCATTACAGCAG-GATGGGA |
| | | GAGCCAACCTCAAGAGAGTGACTCTG-TAACCATC |
| | | AATCTTCCGCATTGCCCTGCTGCCATG-GATGTAC |
| | | TGGCGAAAATAAAGGGTCAACTTTGCT-TAAAGAT |
| | | GCAGTCAGCTAGAGTTTAACTCAAGGAG-GCAACC |
| | | GGCTTCTATGTAATACCTGTGGAAT-GAAAACGAA |
| | | TCCCATGTACCGAATTAAGG-GAAAACTGGGTGCA |
| | | GAGATTTTGTTTGGTTTAGACTCTA-GATATGGTA |
| | | TTACAGCTCCGATTGGGTGGTC-GAAATACGTCAG |
| | | AGCACCCCACATTGCGTAATTCTTCAGG-TATCAG |
| | | ATGCCTGCCTAGTCTACATACATGAGT-TGCAGTT |
| | | TCTCTTCAGCAGTGGGGTTTGGCG-GCTCTGACAG |
| | | TACAGTTAGTAGAGACTATCTATTTTC-CGTGTAC |
| | | ACAACGCTTGCAATGCAGATCTGGGCGC-TATTAT |
| | | AAAAGATCAAACAAGAGCTAGGCTTTCA-GAATTG |
| | | CCTGAAAGCTGCTGCCAATTGCATA-GATCTGCTC |
| | | AAGGCACCAC |
| 57 | P. radiata CSL | CTGTATTCATCACTTTACACCCATGAT-TCCAAAC |
| | | CCTACACATTTACACTGATAAC-CAAGGGTTCAGG |
| | | TTCTTTCCAATTCATTTTAATCCAGGAT-GATAAT |
| | | AAATTTGAATAGCACAATAGCATATTC-CAACTGa |
| | | CATATCCCTACATTTGGGATCTCTTTC-CACGTTA |
| | | TAAATGGCTTCAATTTAGGGATC-CCTTTCCACAT |
| | | TATATAACTGGGTTCACAGTGGTTTGAA-GATAGC |
| | | TGTGGTTTGAAGATAGCTGTATATGT-TATCAAAA |
| | | TGACAGCTCCCTTGCCAGGGAC-CATCGCTTGAAT |
| | | GATGAGATCCCGCCTGTAAGGCAACTTG-CAGCAT |
| | | GATTATTTTACATCTGCTTGACCAAT-TATCTAAC |
| | | AATATACGCGGTGTCGTCGTTCGGT-TAAATAATA |
| | | GTGAAACTTCCTCGTGTTGTCCCTG-CAGTTACGT |
| | | ATGTCTTGTTCTTTTTTTGTTTAATAa-CATACA |
| | | GCAGAGCAAGTGTTGGGTGAATAAATAT-TGGGAA |
| | | GAAGCTGCAGCGTTCACGTTCATTCAT-TCACTCA |
| | | TCGTGAGCAGCAGTACATCAACAGTTCT-TGAAGA |
| | | ACATTGATAGGTTGGCTATTTCAATC-CTTTCATG |
| | | GGGAATATTTAAGTCTGGATCCGAGC |
| 58 | P. radiata CSL | ATCTTATCACATTTTCTCAA-GAGAAGGGTTGTGA |
| | | CCAACTTTAAATTTTG-GTCTCTTTGATGGTGGT |
| | | AAATTGGGGCAATGAGACTCAACATTGT-TAGAAC |
| | | ATTTACCTTTCTCATACTTTGGAGGATC-TATTAA |
| | | GACAAAAGCTCTCATGTATTTCCTTTA-CATGCAT |
| | | GCACATTTATAGGGAATAGAATGGAG-TAGCAAAT |
| | | TGACTTTCTAAGGAAGGCCTACTCT-TGACTCGGG |
| | | GGTTGTGGCAGGTAGTTGAAGACTAGG-GAGCCGG |
| | | TCACTACCAATTTTACCATCAACCATT-TACAGAC |
| | | GAGATACAAAATGATGATTATGTT-TAATTTTTGA |
| | | AACTTTCACTTATTAATTTTTGTGACG-CATTCAT |
| | | AACATATTATGTTAGTATATATGTTCGT-TCACAG |
| | | GTTGTTGGCTTTGGTAACACTATACTAG-TATTTC |
| | | TTTGTGATTATTTTTATGTAATG-CAATATAGCC |
| | | CTAAATGAATATTGTGAAAGT-GATATTTTCAGG |
| | | AGCATCAAGACCATCTTCATTTG-TAAATATGTGA |
| | | TAAAAGGGGGTGTGATAAATTTTAG-TATTTTGT |
| | | TATTTTTAATAAAATAGGAAGTGAAGAT-TATGTA |
| | | AATATTATTTTCTAAATAAAAGGATAT-GAGAGAA |
| | | TAGTTTAGGAAAAAGAATTGGGATA-GAATTTCTA |
| | | TGTTTTTTCAATTAAAATTAGGATAA-GAATGGAG |
| | | AATAAAGCTTCACGCTTTAAATCATTAT-GTAAAA |
| | | CGGAAAAAGCCTGCTTTTGTAAAA-GATAAGGTCT |
| | | GAGAAGACCTATCCCCTTATGTATGTATC-CGTTAT |
| | | TATTATAAATAAAGAGG-TAGCTAATCTCTCAAGG |
| | | GAGAGAGAGGAGCGAGCGCTCTG-GAAAAAGATGG |
| | | ATGATGTCTTGTTAATATTGTTAATATG-GATGCG |
| | | CGTAGTTAATAGTTTATTTGGACTGTG-TATTAAG |
| | | CATTGAATGGTTAGCTGTATATGTTAT-CAAAATG |
| | | ACAGCTCCCTTGCCAGGGACCTTCGCT-TGAATGA |
| | | TGAGATCCCGCCTGTAAGGCAACTTG-CAGCATGG |
| | | TTATTTTACATTTGCTTGACCAAT-TATCTAACGA |
| | | TATACGTGGTGTCGTTATTGGGTTAAA-CAATAGT |
| | | GAAACTTCCTCGTGTTGTCCCTGCAGT-TACGTAT |
| | | GTCTTGTTCTTTTTTTGTTTAATAT-CATACAGC |
| | | AGAGCAAGTGTTGGGTGAATAAATAT-TGGGAAGA |
| | | AGCTGCAGCGTTCACGTTCATTCAT-TCACCCATC |
| | | GTGAGCAGCAGTAGATCAACAGTTCT-TGAAGAAC |
| | | ATTGATAGGTTGGCTATTTCAATCCTCT-CATGGG |
| | | GAATATTTAAGTCTGGATCCGAGC |
| 59 | E. grandis Laccase | ATCAATTCAAGTAAAAAATTTTAATC-CTAACTTA |
| | | GTCATAAACTTTTATGCAATATTC-CAATATAATC |
| | | CGTCAGTCAATATTAATCGGAATTGT-TGACGTAG |
| | | CGATGCGCCACGTAGAATGACTAAC-GATGGCTAA |

TABLE 6-continued

| SEQ ID NO | Gene Homology | Sequence |
|---|---|---|
| | | ACCGCTATAGTAGCGATTTCTGA-CAAATATTAAC |
| | | TGAATGACTATATTTTCCTCATTAT-TCAGGTTAT |
| | | ATTGTTTTGTTTTCATGCTATTTC-CCCAATAGCA |
| | | AATTTGTTCACCTGCTCCTGGAAATTC-CTTACGA |
| | | CGACTCACCACTTATTCTAACGAATCT-GATGGGT |
| | | GATTCTTGATATTATTTGACCATGACAT-AATAAA |
| | | TGTCAAGGGAAAAAGAGAAAAAAATAA-GAAAAGC |
| | | GAAGAAATCCACCGGTCATCATTAGGA-CAGACAC |
| | | ATTATACGCCGTCATAAGGGAAAAT-GAAATTTAA |
| | | CTAAACATCACTAACGTCAACCAAACTC-GAAAAC |
| | | AAAACTTGAACTGCAGTAGCTAGATG-TAGCTCTT |
| | | GGTTCAGCCCCCAGAACCATCGC-CTATCGGGTTG |
| | | ATGGTTGAAGATGTGATCTTGGTC-CTAATCACCT |
| | | AATCAACGAACCACCGTTTCTCAT-TCGCTCCCTC |
| | | CGTATAAAAACCTCGAGGCTTGTC-CTATCTTGGA |
| | | GCATCGCATCCAAGAAACACCATCT-CATCCTGTC |
| | | TCAGTCCCCATCATCACTTG |
| 60 | E. grandis Tubulin alpha chain | GTCGTTTTTATATTGTCTAGCCACATT-AGCATGA |
| | | AAAACAATGTTGTTTTGCATTTC-CTTTGTCGGAA |
| | | AATTGCCGCGTTGGCATTTTGGTTG-GAATGACAC |
| | | TTAAATGATC-CATTTTGTTTTGATTTTGACACTT |
| | | AAGTATTACTTTCCAAAGTTTTGACACT-TAAGTG |
| | | TCCATTCGCACTAAGTTTTG-GCATTTGAGTGTTC |
| | | CTCCGTATCAAGTTTTGACATTTGTAAT-GTACTT |
| | | TTGCTCATAATGCTAATGTGATAAT-GAGACTAAA |
| | | TTAAACATATATTAAAATTTCAGAATC-TACATTA |
| | | AATAATTTAAAAATTTATGAATCATAT-TACATAT |
| | | TACGATAAAGTTCAAGAACTATAT-TAAAAAAATT |
| | | AAATATTTATGGGTCACATTACATAC-GAGTGAAA |
| | | ATTTAAGGACTATTTATTTTGT-TATTTCTTTTTC |
| | | CATTAACAAAAATCTTCCCCACCT-CATTTTAAAT |
| | | TCGAGAAAAGAAGAAAAGCAAA-GAAAAATAATAG |
| | | AGAGGAAGGGACCCAACTCGAGAT-TGGGCTCCAT |
| | | TGATGGAAACTCGCGATCTACTC-CATCTCGACTC |
| | | GACAGCCCATCCTCTGAAGATAACAT-CATCGTCC |
| | | GCACCGCATTGCACCCTACCT-TCTGGGCTGAATG |
| | | ACCACATTGCCCTCCACCAAATCTATC-CGTTGC |
| | | CTCGAATGCCGGATGGCAAAGCAGCAAT-TCCCGC |
| | | AAAAGTCCGAGCCCATTTCCCTCCGGC-CAAATCG |
| | | AGAAAGGACTCT-TGATTTTTGAAAACTGGGCGGG |
| | | CAACTAACCTTGGTTAGGCGCCTCCAT-CATTAAC |
| | | CCCACACCAAAGTTAACAC-CCCCGCTTTCGCTGG |
| | | CACTTTCTAAATCGAACCGCGGTTAACG-TAACCG |
| | | CGGTTAACCAACCA-GATATTTTTCAATTTTTTCC |
| | | AGTGGCGCTCTATATATCTTTAAACTTC-CCCTCT |
| | | GCATTTCCCATCAGCTCTGCAAGTCCTC-CTCCAT |
| | | CTTCTTCTTCTTCATCGTCATCTTCTCG-GAAGGC |
| | | GTCTTGATAAAC |
| 61 | E. grandis Coniferyl Alcohol glycosyl-transferase | ATCAAAGTTAGTCGCACTTTTACATAC-CCAACTG |
| | | TACCTCCAAAGTGCACCATTGAACTTGT-GACAAC |
| | | GTTTAGATTTAGGTAATTATTCA-GAAAACGAAAG |
| | | CGACCACAGGTTTATGAATTGTCACG-CATGACGT |
| | | CATTAATTAAGCGACAAGACGTGCGC-CAAGGCCA |
| | | TGCATTCCTCTGCGGCTATCCTTCTTC-CTGGCAA |
| | | CAGTTCAATTCCTCAGACGGTCTGGT-CAAACCCG |
| | | AAGCTCGACTAGGCCTTTCTCAAC-CAAACCCTCC |
| | | AAGAAAGCCTAAGGACAGCATGC-CCTCGCGCGGA |
| | | TCAACACGACCGACGAGCATCGAACT-TGCGTAAC |
| | | TTACCCCACCAAACGGTCCCCTTCGAG-GTCAAAC |
| | | CCCACGCGAACGACCGATGAATCGAA-CATCTAAT |
| | | CTCGCCTCTCCTCTCCTCCACTGC-TATATATTTC |
| | | AGCTACTCTAACACACTCTCATCACCAC-CAACTT |
| | | CAAACTCTCTCTCTCCCTCCCTCCCTC-CCTCTCT |
| | | CGCTCACACATACACACAT |
| 62 | E. grandis CONSTANS-like B-box Zinc finger protein | CTGGAGTTCACATTGAGCTGGTGC-CGATCGATCC |
| | | GTTTCTTACATTTTTTCATCCCGGTC-CGTCTCCA |
| | | TTCTCTGCCTCCGTCGGCATCTTGGGC-GACGAGA |
| | | GGAGGAGGAGATACGCGGTAGCTGAC-GAGTTCGA |
| | | GGCGCAACTTTTCTTCGATTAACTTT-TAACTCGA |
| | | CACCGATCATGCTTTAAGCACTTAC-CCTTTTCGA |
| | | GAAACAGGAGATGGACATGGAGTTC-GACGTAAAG |
| | | ATCCCGTCTTTGATTACAGAAAAGCAT-GCTCAG |
| | | AGGAGGAGGAATGATATTTCCTGTTTC-CATGGTG |
| | | GTGATAAAAGCTTTGATTTTTC-CTTTTCAATGAC |
| | | GTAGCTCGAGTGGCCGATAATCGACAAG-GAGGTC |
| | | CAACTATTAGCACCAGAATGGAAAAGAA-GAGGGA |
| | | GATAGATAGCGACTACCACAAGCTACAT-TACAAG |
| | | GATTAATATAAGCAAAATTACTG-CAATACGATAT |
| | | TGACCCGATTGGCTTTGGAT-GATAAAAAAACAAT |
| | | TCTATATTCAATCACACGTCTTCGTC-CCCGGGAA |
| | | AGCAATGATCCAAATCATGTCAAGGAGC-TATACT |
| | | CCTAAGCCCACGTTAGCCCACACTCT-TCTCGAAA |

TABLE 6-continued

| SEQ ID NO | Gene Homology | Sequence |
|---|---|---|
| | | GACATATCAAATCAATACACT-CACTCTCTCTATT AATATTCAATTTCTGCATAATTTCTTCT-GTCACT GCCCAAGACGTTCTGTAGCACTAAGGGGTG |
| 63 | *P. radiata* Alpha Expansin | AAATTCACATTCTTTTTCTTCGCACGAA-GAAAGG TTAAAGATACAACTCGGATTGTAT-TAAAGGAAAG AGATTGGAACAAACAGAATCTG-GAATATAAGAAT ACACCAGATCGCGGGCACGGCCACAGTT-TAACGG CCAGCCGAAAGGCCGGTCCGTTGGGTCT-GCCGGT GACTTGGTCGTGTGAGGGAATCTCTG-GAGTCCGG ATCCGGTCTTGCCTTGAGACCTACCA-CAACCACA GCAGTTAATGCAGTTTACATCCTAT-TAATATAAA TACCAAATCGCCATTCCAAATTATTAT-CACAACA ACAAATCTGATTTGATTTCGATGCAGT-GAAGCTC TTCATTTTGCAGTGACAGTGACGTT |
| 64 | *P. radiata* Tbbulin Beta Chain | GGACAAACGAGATTTTATTCTCATC-CAGTTCCAT CTATTCTCTGTCACTGTAACTTGTA-GAGATTATA TTAACGATGGGGTTATGATCGCT-TCACGTTTCCA GATAGAATGGAGAGAACAACAGCAAG-GAAATCGA CAGGCCATAACTTAATGGGGTCACTG-TAAGGCCT TCCGGGGCGTAAACACGAAGCTTTGTA-CAGAGAG TCCACCCAAAAACAAGCATCATCACAGT-GACAAT AATTGAAAAGAAATGAAAAGCTC-CACTGGGCTT CTCTTTCTGGAACCTTCTCTCCGAA-GAAATCGAC TTACAGAATTTAAAAAATTTAAAATGAT-GTTCTG TAGCAACCTAGGCCCTCCACTGTCAC-CATACCTG CCCCTCCATTGTCACATTCTATCTTCT-CATCTTA AACACCACGCATCTCGCTTTTCCACTG-CATGCAG AGATCGACGATATCTTTGCT-TGATATCTAAGTCG AATTCTGACCGCAAACCTCCATCAGACT-TGCGCA CATCTTAATAGATGGCGCTTGTTTGTGC-CCAAGG GGTTCTGGGTACTATTTGAGGACTGAAG-GTGTTA TGCTTCAGAGATTTGGAGGCCTAGGGT-TCGATTC ACAGCCGTTGAGATTTCGACAGAATTTG-GATTTT TTTTCTCTGGCTGTTTGAGGAGAAT-GAGAGAGAT ATTGCACATCCAGGGCGGGCAGTGCGG-GAACCAG ATAGGAGCCAAGTTCTGGGAAGTGATAT-GTGACG AGCATGGATTGATACCACGGGCTCG-TACTGTGG GGACTCCGATCTGCAGCTGGAGAGGAT-CAATGTC TATTATAACGAGGCAAGCGGCGGCCGC-TATGTGC CTCGGGCAGTGCTGATGGATCTCGAAC-CCGGGAC CATGGACAGCGTTCGATCAGGTC-CCTATGGTCAG |
| | | ATCTTCAGGCCAGATAACT-TCGTCTTTGGGCAGA CAGGCGCCGGGAACAACTGGGC-CAAAGGGCATTA TACTGAGGGGGCAGAACTCATTGACTC-CGTTCTT GATGTCGTGCGTAAGGAGGCCGAGAGCT-GCGATT GTCTTCAGGGATTTCAAGTATGTCATTC-CCTGGG AGGAGGAACAGGATCGGGATGGG-GACTCTCTTG ATTTCCAAAATAAGGGAGGAGTACCCA-GACAGAA TGATGTTGACTTTCTCTGTTTTTCCAT-CACCTAA GGTATCGGACACAGTGGTGGAACCT-TATAATGCA ACTCTTTCTGTACATCAATTGGTG-GAGAATGCAG ATGAATGCATGGTTCTTGACAATGAAG-CACTTTA CGACATTTGCTT |
| 65 | *P. radiata* Putative Beta 1,3-Glucanase | GTATCATTATTTCAGTCATTATC-GATAATGATAA GCCTCAAATATGAATCAATAGTCTCT-TAGTCATT TAATTTATGGTTTTCAGTGTCGATGT-GCTCTCCT GCCAGGGCTCCACCAATCTCCTTTAGGT-TCAGTG TACATCGTCTGAAAATAAGTTGACAAG-GCCAGGT CAATGCAGAAGCCTCCTGGCTTGGGGAC-CCTAAG TGTGAAATCAATATATTTTCCTCGAGT-TCTTGAC CTGTTAGCAACTTCGACACTGCAACT-TGTCCTAA TCTTTGCTGTGTATTATGTATTTTGTTC-CAAGTA TTGGAGTGTAGCACAGTGGATGGTA-GAGAGGAGG ATCTAGATCAGTCACTTTTACATA-GAATGGAGAT GATAGTAAAAGCAACTACAATTAC-GATCTTGCTA CCAGTCATCCTATGTTGCATCCCATGTG-GAGAAA GTGGAAGCGGAGGCAGGAGTTTGGCG-CAGCGTTT ACCAGCCCTAGGCGTTGACTATGGA-CAAACTGCA GACAATCTTCCTCCACCATCTGCAGTAG-CAAAGC TGGTTCAGAGTACAAGTATTTCAAAGT-TGAGACT ATATGGAGCAGATCCTGCAATTCT-TCAAGCATTT GCTAACACAGGAATTGGGTTAGTTGTAG-GCATTG GTAACGATCAAATCCCATCTCTGAAC-CAGCTGGC TGTTCACAGAATTGGATTAAGAA-CAATATCGTT CCTTTTGTTCCTGCCACTGATATCATTG-GAATCT CGGTGGGGAACGAGGTTCTGT-TCAGTGGGATGG GAGTCTGATTTCCCAGCTCCTCCCTG-CATTGCAG AACCTACACACTGCCCTTGTGAG-GTTTCACTTG ACCAGCAAATTAAGGTCTCCACACCT-CATTCTCT GGCCATACTTTCTACATCTGTC-CCCCCATCTGCT GGCCGTTTCAATGAAAGTTTTGACAT-GAAATCCC TGCTTGACTTCTTGCAGAAGATAGGGGC-CCCATT |

TABLE 6-continued

| SEQ ID NO | Gene Homology | Sequence |
|---|---|---|
| | | AATGATCAACCCATACCCCTACTTTGCTTACAAG |
| | | AGTAATCCCACCGATCAAACCCTGGCTTATGCAC |
| | | TCTTCGAGCCCAACCCGGGCTTCTATGACACAAA |
| | | CAGTGGGCTCACCTATACCAACATGTTTGATGCT |
| | | CAGCTTGATGCAGTGTACTCAGCCATGAAATATC |
| | | TGGGTTACCCTGGTGTTGATATAGTGGTGGCTGA |
| | | AACAGGATGGCCAGCTGTGGGGGATCCTACAGAG |
| | | ACAGGGGTGAGCTTACAGAATGCAATTGCTTACA |
| | | ATGGCAACCTGATCAAGCATGTGACGTCCATGAC |
| | | GGGGACCCCATTGAGGCCAAATAGGTACATTCAA |
| | | ACCTATATTTTGCCCTCTTTAATGAGGATCTGA |
| | | AGCCAGGACCAACTTCGGAGCGCAATTATGGGCT |
| | | GTTTAAGTTGATATGACAATGGCTTATGATGTG |
| | | GGTTTGTTGCAATCGCCGAGTGCAGCTCCATCTC |
| | | CTCCTGCTCCACGCACTGGGGGGCCTGTGACAAC |
| | | TCCTCCTACAGGTAAAGTTTGGTGCATTGCCAAG |
| | | CCGGGCGCCGAAGAGCAAACTTTGGAGGCAAATT |
| | | TGAACTATGTTTGTGGACAGGGCATTGACTGTAG |
| | | GCCTATTCAACCAGGAGGTCCTTGCTATTCACCA |
| | | AATACAGTGGCAGGCCATGCTGCTTATGCCATGA |
| | | ACGCATACTATCAGACTGCGGGTCGGAACAATTG |
| | | GAATTGTGATTTTGCGCAGACGGGAACTCTTACC |
| | | TCCACAGATCCAAGCTACGGGGCCTGCGTGTACC |
| | | CGACCGTCTAAGATATGAATCAATCAATCAATCC |
| | | TAGTGTTTTCTATTCCACTTGTTGTTCGGTATAT |
| | | ATTTTCCAACTTGTCTTTTCATATGAGTGAGATG |
| | | TATGAGGTACCTATTTTCAAAGTTGTGATAGCAT |
| | | ATACATCATAAGATGTAATGTGTATGTTTGGGTT |
| | | TTATTCCCCCTTTAATGTCGTTACTCTGACCATA |
| | | TAAAAAAATTCACAGAATTTGTGAATGGTAGTAT |
| | | TATTTTTATTTATGTATTAAGGAAATTTAAGTG |
| | | GTGTTAAAAAAGGAAAAAAA |
| 66 | P. radiata Cinnamoyl-COA Reductase | AAAAAAATTATGATCTGTAAATAAATAATTC |
| | | CATATATAATAGATATATATAAATTTTACAACCC |
| | | ACAGATAAATATTAACTTTCCGCCAAAATAATTT |
| | | CCATAAATGAAATAAATGACCCAATATTACGATT |
| | | TTACACCAAAATGATTTCCATATGTATATATAA |
| | | AGCCTGTGAGTCCAAACGAAGCATATGAATCTGA |
| | | ATCGCAGAGGGAGGCTGGCCAACCACCATTAGCT |
| | | ATTCAATGAAGTTGGTAGCCACCCAAACAAGTCA |
| | | ATTCAAGAGTCAATCAAACCAAACTATGATTAAA |
| | | ACTACCAACCGCACTTTCTGAGCAACCCACTTTC |
| | | CCTCCCTCGCTTTACTTTTTGGAGTCGTGGGGA |
| | | TTTTTCCAGTGTCTCAATTTCTATAAATTTGGCC |
| | | TCACATTTCCTACCAACTCATTGTTAACGGGAGT |
| | | CCTCTTGTCAGGCTCCGCTGCTTCTTGTGATCAC |
| | | ACGATACCTAGTGATCCATAGATAACTAAAATGC |
| | | TGTGAGCAGTCTGAATTCTTGCTTTCTTTCCCC |
| 67 | P. radiata Dirigent | GTCTGTATTATTATATTCTGGGTCACTACTCAAC |
| | | CCCCACGGTAGTGGCGTGACTTGCGTCGGCGTGTT |
| | | ACAGAATCCATAATCAGAAAACGAACGGAAGCTG |
| | | CAAAGGTGTACGTCCAACGGTTGCGGTGAAAAGC |
| | | CATTGGTTACGTCCAGCGGTGGAATTCTGTAATA |
| | | CTGAAAGGATTTGGTTACAGATGGCTCGACCAAA |
| | | GACAAAATAGTAATCAAATATTCAACCGAAAGGG |
| | | AGAAAGTTGCTTATGGGCATCACGTTATAAAAGT |
| | | GGAACTCGACTTTCATTACCACACATTTCTCATT |
| | | TCTTTCTCTGTACTGAGCCATTCGTTCTCCTTTC |
| | | TTTCAGAGA |
| 68 | P. radiata Caffeic Acid OMT | CTGGCAACTGGCTATTCCTCATTCGTCAGTGGGA |
| | | ATGGGGTGGGCAGACGATCTTCTAGAGCCTGTGT |
| | | GGTGTGGGGCCCTTCGACTTTTCAATGGCCCGTT |
| | | GGTCACCAGCTTGGACTAGTTTTGCTGTTTCCAT |
| | | GGTGACGGTTCGTGCTCTATAAAATAATTTAACC |
| | | GAGTGGGTATTTTGCATGGTGGCCGGATTTCCAA |
| | | CAATCTCAGGTATTAGCG |
| 69 | P. radiata High Mobility Group Transcription Factor | ATCTAACCCACGATCTATAATAATAGTCAAGGAC |
| | | CCTAAATAGAAATATGGCCACCACCCTACCACGA |
| | | GAGCTTATCCTAATACAACCACGAAAGCCCCTCC |
| | | GAGCTTATCCTAATCAACCACGAAAGCCCCTCC |
| | | ACTCGTGGAGGTTATAGATTTCCCCCGTGTAAAC |
| | | ATATAAAAGGAACTTTTCTCTTTCTTCACATTCT |
| | | TTGCCGGTCATCCATCTTGCTCATTTCTACTTCC |
| | | GCCTCCTCTTCTCTTCCCTCGTCTAGTGTTTTCT |
| | | TTGCGTTGTGTAGTGTAATGTTTGCTGTTGCTTC |
| | | ATATCAATAGTGGTGGAATTTTCCTTCACTGCGA |
| | | GCAGATTTTCTAAGGAGA |
| 70 | E. grandis Tubulin alpha chain | GTCGTTTTTATATTGTCTAGCCACATTAGCATGA |
| | | AAAACAATGTTGTTTTGCATTTCCTTTGTCGGAA |
| | | AATTGCCGCGTTGGCATTTTGGTTGAATGACAC |
| | | TTAAATGATCCATTTTGTTTTGATTTTGACACTT |

TABLE 6-continued

| SEQ ID NO | Gene Homology | Sequence |
|---|---|---|
| | | AAGTATTACTTTCCAAAGTTTTGACACT-TAAGTG TCCATTCGCACTAAGTTTTG-GCATTTGAGTGTTC CTCCGTATCAAGTTTTGACATTTGTAAT-GTACTT TTGCTCATAATGCTAATGTGATAAT-GAGACTAAA TTAAACATATATTAAAATTTCAGAATC-TACATTA AATAATTTAAAAATTTATGAATCATAT-TACATAT TACGATAAAGTTCAAGAACTATAT-TAAAAAATT AAATATTTATGGGTCACATTACATAC-GAGTGAAA ATTTAAGGACTATTTATTTTGT-TATTTCTTTTTC CATTAACAAAAATCTTCCCCACCT-CATTTTAAAT TCGAGAAAAGAAGAAAAGCAAA-GAAAAATAATAG AGAGGAAGGGACCCAACTCGAGAT-TGGGCTCCAT TGATGGAAACTCGCGATCTACTC-CATCTCGACTC GACAGCCCATCCTCTGAAGATAACAT-CATCGTCC GCACCGCATTGCACCCTACCT-TCTGGGCTGAATG ACCACATTGCCCCTCCACCAAATCTATC-CGTTGC CTCGAATGCCGGATGGCAAAGCAGCAAT-TCCCGC AAAAGTCCGAGCCCATTTCCCTCCGGC-CAAATCG AGAAAGGACTCT-TGATTTTTGAAAACTGGGCGGG CAACTAACCTTGGTTAGGCGCCTCCAT-CATTAAC CCCACACCAAAGTTAACAC-CCCCGCTTTCGCTGG CACTTTCTAAATCGAACCGCGGTTAACG-TAACCG CGGTTAACCAACCA-GATATTTTTCAATTTTTTCC CAGTGGCGCTCTATATATCTTTAAACT-TCCCCTC TGCATTTCCCATCAGCTCTGCAAGTC-CTCCTCCA TCTTCTTCTTCTTCATCGTCATCT-TCTCGGAAGG CGTCTTGATAAAC |
| 71 | P. radiata WD-40 Repeat | AAATAGGCTAAATTAGAGAAATAC-TATGGGTTGT CAAAACCTAGAATACGATAATTTGAC-CGAAATAT |

TABLE 6-continued

| SEQ ID NO | Gene Homology | Sequence |
|---|---|---|
| | Protein | TTAGATAATGTAACATAACATGACATGA-CATTAC AACATCTCTTCCATAGAGAATCTCT-CAATAAAAT AAAATATTGCACAAACAAAACCAACT-CAAAACTC AATTTATATTACACAATATAATAATAAA-CAATTT CAATTAAAAACATTTTACCTTTATTTAT-TAATAA ACCTCACACTAACACATTGTTAAAAAAG-TAAAAT AAAATAACAAACGCCATATAAACCCAT-AAAAATT TCCAAAACAATATTAATATCTTTATCAT-AGTTTT TAAGCTAAAGTTCGATGATCCTTTAA-CATTACTA GCCACAAGGATGCTTACTTCCTTG-CAAAATAACA ATGCAAAGACCCAACGCAGTGATATGT-GATTTAA CGGTAAGTATGGTTGGGTGAAACCAA-CAAGACTG CAGTTCAAATTCCATTGAGTATATGGC-CTGCTAT GATCTCAGCTTGGTGAAACCAACAA-GACTGCAGT TCAAATCTAAATCCCATTAATTATGT-GACCTACT ATAATCTGGGCTTAAGGAGTAGGT-TGCTCGCTAT GTTTTGGTGTTATAAAGTAGCCATAAA-GATTAAA CCTCAAGCTCCCTAAATTAATCCAA-GAAATTAC CGATTCATTATAATTAAAAAAAATG-CAAATACCC ACCTTAAAGAAAAACAATGTAAAGAG-CAATGAAA TCAATTTAATTGTCTTCTTTTAACAC-CAATAAAA ATTTATAAAAACCTCATAATTAAAAA-CAAAGCGT TAGACTTTTGGAATAACCTTCCTTAAT-TGCTTCT CTAATTTATGATTTCTAAGTCATACCAC-GATCGG TCGTTTTAGCAAAAGCCTGAAAGGCAAG-TAGAAG ATAAACGTATGCTTGGAAATAAATATAT-GTCATT TTTCATTTTATATCCTTCGAATCCGT-CATTCGTC TGAATGATCAGACAAACCCTCCCAGATC-CTGCTC TGTTCTGAAGCATAAACCT |

---

What is claimed is:

1. An isolated nucleic acid molecule comprising the sequence of SEQ ID NO: 7; wherein said sequence is a Ferulate-5-Hydroxylase promoter conferring xylem-preferred gene expression in a plant cell.

2. The isolated nucleic acid molecule of claim 1, wherein said sequence is operably linked to a gene encoding an RNA interference molecule.

3. A vector comprising the isolated nucleic acid molecule of claim 1, wherein said sequence is operably linked to a gene encoding an RNA interference molecule.

4. A plant cell transformed with the vector of claim 3.

5. A transgenic plant comprising the plant cell of claim 4, wherein the transgenic plant expresses the gene encoding the RNA interference molecule.

6. The transgenic plant of claim 5, wherein the transgenic plant is selected from angiosperms and gymnosperms.

7. A method for regulating the lignin content of a plant, comprising (a) transforming a plant cell with a vector comprising the isolated nucleic acid molecule of claim 1 operably linked to a gene encoding an enzyme involved in lignin biosynthesis; (b) culturing the transformed plant cell under conditions that promote growth of a plant; (c) selecting a transgenic plant; and (d) measuring the lignin content in the transgenic plant, wherein said transgenic plant has reduced lignin content compared to a non-transgenic plant of the same species.

8. A method for obtaining wood with a reduced lignin content, comprising (a) transforming a woody plant cell with a vector comprising the isolated nucleic acid molecule of claim 1 operably linked to a gene that encodes an enzyme involved in lignin biosynthesis; (b) culturing the transformed plant cell under conditions that promote growth of a woody plant; (c) selecting a transgenic woody plant; and (d) obtaining wood from the transgenic woody plant, wherein the wood obtained from the transgenic woody plant has a reduced lignin content compared to the wood obtained from a non-transgenic woody plant of the same species.

9. The method of claim 8, wherein the woody plant is a species of *Eucalyptus* or *Pinus*.

10. The method of claim 8, further comprising the step of making wood pulp from the wood obtained from the transgenic woody plant.

11. The method of claim 10, wherein the woody plant is a species of *Eucalyptus* or *Pinus*.

12. The method of claim 8, further comprising the step of making paper from the wood obtained from the transgenic woody plant.

13. The method of claim 12, wherein the woody plant is a species of *Eucalyptus* or *Pinus*.

14. A gene operably linked to the isolated nucleic acid molecule of claim 1, wherein said sequence regulates the expression of the operably-linked gene in a plant.

15. A DNA construct comprising the isolated nucleic acid molecule of claim 1 operably linked to a nucleic acid sequence, wherein said isolated nucleic acid molecule regulates the expression of the operably linked nucleic acid sequence in a plant.

16. A plant cell comprising the DNA construct of claim 15.

17. A transgenic plant comprising the plant cell of claim 16.

18. A method of regulating the composition or content of lignin in a plant comprising (a) introducing into a plant cell the DNA construct of claim 15, wherein the operably linked nucleic acid sequence encodes an enzyme involved in lignin biosynthesis; (b) culturing the plant cells under conditions that promote growth of a plant; and (c) selecting a transgenic plant that has a lignin composition or content that is different from the lignin composition or content of a plant of the same species that is not transformed with the DNA construct.

* * * * *

SEQUENCE LISTING

<160> NUMBER OF SEQ ID NOS: 86

<210> SEQ ID NO 1
<211> LENGTH: 168
<212> TYPE: DNA
<213> ORGANISM: Eucalyptus grandis

<400> SEQUENCE: 1
aaaaccacaa atggccgcgg gacgtcacaa ttttttttc cttctagaag ctctatagtc     60
aaagctgatc tataaatttt tgggaaccac aaccaccatg tctcgccacc ttcgctcgaa    120
ccttatcacc accaccgccc ttgagccctc ctccatcaac tcttcttc                 168

<210> SEQ ID NO 2
<211> LENGTH: 934
<212> TYPE: DNA
<213> ORGANISM: Eucalyptus grandis

<400> SEQUENCE: 2

| | | | | | |
|---|---|---|---|---|---|
| aaaacaatgt | agcttctctg | tgttatgaaa | actaacaaaa | gggcacatct | atttctccat | 60 |
| gaccattata | ttcggaggag | catggtcaaa | cttaaatcaa | aatttattat | ccataactta | 120 |
| caaatttcca | atttagctaa | actcaaatcc | caaagtatag | caattctgtt | aaaattttat | 180 |
| catccgatag | tatagagcaa | tatttttataa | tacttacatt | gctcagctca | attacaaatt | 240 |
| ctatttgtcc | acaaattcaa | acattttaat | gatgcattcc | acataaaacc | aatggtttga | 300 |
| gacacctttt | caaaaaaaag | aaaaaaatac | actagcattg | cttagacaag | ttaatcaatg | 360 |
| aaaaataact | ttatcttgtt | tttaattaag | gatgaaaagg | agttacaaac | gcttgtttca | 420 |
| agataaatat | ttttcaaatc | tttaatatta | caagaaataa | acggaccttc | ttatcaacca | 480 |
| aaaaaatgta | acataaaagg | aacttaccaa | tttgattgga | ctcatttatt | gattttttgga | 540 |
| aaaatgtcgc | aaattttcgt | tgagttttag | ctccatgtac | aatttagtca | ttgaactttt | 600 |
| aatttattca | atataattca | tgaactttct | atacatattt | agtccatata | aaaattaagg | 660 |
| gaccaaattg | agtattcacc | aaaattttag | ggaaaatatt | gaataaataa | aaagttcttg | 720 |
| gaccaaattt | catattgaaa | taaaattcat | ggacaaatca | ttattccttg | attaaacttt | 780 |
| tttatgtaga | cacccgtaaa | tacaacctgc | caaggtttgt | ttgcaaggcg | tttgcaaggc | 840 |
| gtttgcactt | aagcgggacg | gaggcgtcac | cagtcaatgg | gcatgtccag | tggcttcccc | 900 |
| ggcttgcgaa | taggatgctt | cctgaatcat | ctcc | | | 934 |

<210> SEQ ID NO 3
<211> LENGTH: 408
<212> TYPE: DNA
<213> ORGANISM: Eucalyptus grandis

<400> SEQUENCE: 3

| | | | | | |
|---|---|---|---|---|---|
| aaagtttctc | tgtagagaga | gggagggaga | tatatctgcg | gtttgcgtct | ctatttcgct | 60 |
| tgtgcagttt | tactactccc | caaacacaca | cacactctct | ctgtttctct | ccttttttccc | 120 |
| caaatcagaa | gaagaaacga | cagtgtagta | gtgcagtttc | actacaccgt | ctatactaag | 180 |
| ggtaatcgtt | tttttgaaag | cacatgcata | tagccgttgg | aaaggggagg | gcaccgagat | 240 |
| cgaatcggat | ggctgatcct | cactagccgt | tagagagaga | gagagagagg | gagggataat | 300 |
| catgtgcgga | catatatccg | caatttgcgt | ctctatttcg | cttgtgcagt | ttcactactc | 360 |
| cccacacaca | ctctctctct | ctctctctcc | ttttccccca | aatcagaa | | 408 |

<210> SEQ ID NO 4
<211> LENGTH: 847
<212> TYPE: DNA
<213> ORGANISM: Eucalyptus grandis

<400> SEQUENCE: 4

| | | | | | |
|---|---|---|---|---|---|
| ccttgtatttt | ccccaacatt | aaatgaaagc | ctacatccaa | aaacgtggac | ccggcattaa | 60 |
| agaaaaaccc | catcatctca | tcccatcctt | tatttcaacc | ctaaagtgaa | attaagatat | 120 |
| aagacgaaac | cacccccaac | cccccaaaaa | aaaaatatta | agggaattcg | ttttttttgaa | 180 |
| agcacatgcg | gaggtagctg | ttggaaaggg | gcctctacgt | tcggaaggaa | tgcgaccatt | 240 |
| ccatcgagat | caaatcgaac | tactgatgct | cactagctgt | tgcgtttaaa | ccttctttgt | 300 |

-continued

| | |
|---|---|
| aaagcgataa gggaattcgt tattttgaaa gcacatgcgg aggtagccat tggaaagggg | 360 |
| cctctacgtt cggaaggaac acgaccgttc caccgagatc gaatcggacc gttgatgctc | 420 |
| actagccatt gtgtttaaag ttctctgta gagagaggga gggagatata tctgcggttt | 480 |
| gcgtctctat ttcgcttgtg cagttttact actcccaaa cacacacaca ctctctctgt | 540 |
| ttctctcctt tttcccccaa atcagaagaa gaaacgacag tgtagtagtg cagtttcacc | 600 |
| acaccgtcta tactaagggt aatcgttttt ttgaaagcac atgcatatag ccgttggaaa | 660 |
| ggggagggca ccgagatcga atcggacggc tgatcctcac tagccgttag agagagagag | 720 |
| agagagggag ggataatcat gtgcggacat atatccgcaa tttgcgtctc tatttcgctt | 780 |
| gtgcagtttc actactcccc acacacactc tctctctctc tctctctcct tttcccccaa | 840 |
| atcagaa | 847 |

<210> SEQ ID NO 5
<211> LENGTH: 286
<212> TYPE: DNA
<213> ORGANISM: Eucalyptus grandis

<400> SEQUENCE: 5

| | |
|---|---|
| aaattatgca atttcttaat caggcctagc tagaaacaag gcaaggaaa gcccccgacg | 60 |
| ggctcttatc tgctgacgtg gcacgccgtg ggtgggcccc ccgggtctt ccttcgacga | 120 |
| aacctcatcg tagacaatca atcctcctc tcgatcatta ttgcaaagcc aacacccagc | 180 |
| attgaatcga tccccacctt ctcctcctcc tcctcttgat cctttttgtc ccgatgatga | 240 |
| tgggtatctg atcagccgat tcaatcccat cgtctccttc cttctc | 286 |

<210> SEQ ID NO 6
<211> LENGTH: 216
<212> TYPE: DNA
<213> ORGANISM: Eucalyptus grandis

<400> SEQUENCE: 6

| | |
|---|---|
| gtgcggacac gtgtcccctt atcccgccca agaccgcgca aaacctgaaa atcctcacta | 60 |
| ttccctcact ttcggcgaat tcgaaacagc gcataaagga acacggaaag aacattctct | 120 |
| accccaagac gacgacgacg acgacgacga cgacgccgcg ccttatataa accatcgcca | 180 |
| ctcctggcca ttcccttctt tctccccaga tccaat | 216 |

<210> SEQ ID NO 7
<211> LENGTH: 473
<212> TYPE: DNA
<213> ORGANISM: Eucalyptus grandis

<400> SEQUENCE: 7

| | |
|---|---|
| aaagataaaa atagtgtgga aaatagattt gagaagtgtt catatatttc gatttatcat | 60 |
| agcaaagatt ttatcgacct attttaggct ttatagtgtg actatttaag ataacgaata | 120 |
| ttaatcgaga gatgcacaat taataagaga tattctcacg atcttgagat atatagaaac | 180 |
| cgacagaaaa tatattgatt atctctaata tagaataata ttctagagaa gtattgtaat | 240 |
| tgtgaccacc aactaaaatg gggcagacaa agtagagggc caggtatagt caaggccagt | 300 |
| gaaaaggaaa atgaaatgaa ataaaagaaa agaaagaaa aatcaaatcc tccaacttgt | 360 |
| gtacaggata cacccgaagc tttgtgtata taaaggccac ttaatatctc ctccaaccta | 420 |
| gcaacacatt cgaaagataa gttgcgctta atcctctcc aaaagagcta atc | 473 |

<210> SEQ ID NO 8

```
<211> LENGTH: 519
<212> TYPE: DNA
<213> ORGANISM: Eucalyptus grandis

<400> SEQUENCE: 8
ctgctgaaat tctcgaggaa gttgagaggt tccagattag atctttacca aacaaaaaaa      60
aactattgct tatgctaaat tggtcattat aataagattt ttagaatact cgttgagtat     120
actcaactca agatattata agttttctca attggttttt ctccatttct tatgatccgt     180
ccacgagctt ggagtcgctt ttgaagatgt agccagccca acagaaccgt ttccttcatc     240
ttcccgcgaa agtttcatgt catctccctc tctgcatca cgaaccaaac ctctgctctc      300
tctctctctc tctctctgct tcaacacaat gacaccaaca tcgcaccctc ctcaccttcc     360
caaccaccgc cataccatct cctttaagca ttccgatgag tccctgatcc accgccttct     420
cactgagcct tcccgctctc cctcttctcg tctcactttc tcatataaag aagtgaaaga     480
atacgaggat actccacttg ggtatcgcca agaactcat                            519

<210> SEQ ID NO 9
<211> LENGTH: 1607
<212> TYPE: DNA
<213> ORGANISM: Pinus radiata

<400> SEQUENCE: 9
cctttgggaa tgaactttga gaccacctcc aacccggatt ctgaaatcca tccagcaatt      60
ccaaagttcc aaaccgaaat aaacatccca ccataccatg gcattcggaa aaaagctagg     120
ctaagctgaa aatcactgtc ataacccagt aagaccatgc cactaatagc aagagaacca     180
tacaccaaca tgcaaagcca tgcatgtcca aaccagctag gaaatcacac atgcaaaggg     240
ttacctgcaa gtattcctgt tgaagttgct tgatcctact ttcttttcct tgagccttgc     300
ttgccttcct ttccttttgct tgattttcct ttccttgctc caaactgagt tgctctaaga    360
aaactctaag tgaccaagag agtgagagag agagagaata atgagagtcc aaacatgaac     420
ttgacaaaag ccatgaactg atcctcagaa gtcatttat gcacgaggct tctatttct      480 tcatttttcca tcatttttcct tcaatttcct catcacatgc aacgtgcgac ttttcacccc    540
gttttcctcc taatttcttt tattttcata aataaatgtg ccaaaaatgc ctcttgcctt     600
agcctttgcc agtttcctta gccaaaacac acatccaatg atgcccacta ggatatcttt    660
gcccaacatt aagcctggaa taaatgtctc ttaatcgtgg tcttatttg cttttattaa      720 cttttattac atgaacttt cactaaagct attacaaaga tatatttatt atggcaatta     780
tgtttgattt ttgaagagct agtaacttt agtttattat ggccttttcc gtaaacttat     840
tttcttgaaa atctctataa atccaatgaa aaatttatag aatatatgtt gtgttttctt    900
cactacctct aataaatttt ttacttagta atctacaaag ccatttatta aaaaattcaa     960
gttaattaaa aattaatatc atttcaaaag tctttttaat atagtcaaag tttattaaat    1020
tctatgatgt atatttcttt taaataaatg aagaatccat ttttttactt aaaaccatat    1080
attttttata acgttgataa atagcatgca tttatataaa caatatata ttttataac      1140 gttaagagat tgttaaaact tttaaataat taatatttta ttattgttt tgaaaatgtc      1200 atgatttcca cctacctcgc ccatcaaatc ttgctgcaaa ccaggcttac ccaaccccac    1260
acccacaata tattttggg atctggtgcc cccacctttg atcacagtga acaccataaa     1320
gacaaattat aaaggcaagg ggacttggca cccatgaggc aaccgaaagc aacaaatcat    1380 tttttttccaa agagatgagt gtatgccaac gaagaaacac gatgaaccca cgtgtcattg    1440
```

-continued

| | |
|---|---|
| gccaactccc actttcgaca aaaagaagga aattagaatt aaaaaggcga ataaaaattg | 1500 |
| aaaggccatt taaatagaa ggaagaatag cctatatggt agatttaaat gcttttttga | 1560 |
| aatccggtta ctcgcaagat tatcaatcgg gactgtagcc gaagctt | 1607 |

<210> SEQ ID NO 10
<211> LENGTH: 1163
<212> TYPE: DNA
<213> ORGANISM: Pinus radiata

<400> SEQUENCE: 10

| | |
|---|---|
| aaacagagca gataacacta aaagaccaa ccctgttagg aggggagaaa caaaaaagat | 60 |
| cacactaaaa agaccaaccc tcttatctaa acttattttc tcttatctct accccttcta | 120 |
| ttttgaacct ttatcatttt gatagaaaat atatgttaat aaccattaaa cctacattgt | 180 |
| caagctagtg taacttatat gttaataacc attaaaccta cattgtcaag ttagtgtaac | 240 |
| tcctttggtg ggggtggttg tcttcctctt caatctcatg ctatgacaca cttgttttt | 300 |
| aataacatag gccgacaagt ttgagccatt atctatcttg attcctcgaa atgataaata | 360 |
| gatgttgtca gtggacttga aaaaaccaa gtagggaaca ccacgtaatc tttccaatgg | 420 |
| cattaaaagc tactttgaaa tatgtaacac ttagcaatcc ttccaaggca ttaaacctac | 480 |
| tctaacctat ggaacactta gcatccttcc cacggttgat aataaatgat tgattcctca | 540 |
| gaataacaaa taaaaaaaaa ctaaaaact tactctaaaa tataaaatga gtatggaaca | 600 |
| cgtggcaatc cttcccatgc tcggcggtag ctactctctc cagagatttg aataacacag | 660 |
| gcgccgcaat tatgagagag cagtggagtt aagacttagt agccatggtt attttgaacg | 720 |
| cgtggcaatt cttccaaagg ttggtagtta ctctatccag agatttgaat aacacaaatg | 780 |
| ctgcagttat gagagagtag tagagttaag tcttgtcagc aatgatagtt acgaacaacc | 840 |
| gtaatttctg gctatctctg tgtttattgg tcgtttactt gctacagtgc tctcacccca | 900 |
| catggtaaca gtgttcgatg gccatgattt ctccccaccc cgccaaacct ctacgttttt | 960 |
| attctttaa taactcctaa tttaatatat aagagggggc aaggtgttca tacagattcg | 1020 |
| tgcaaacgac ctgagttcag cacaagttta gtcattccat gcgaactcga ctggctcacg | 1080 |
| agatccctcg ctgcagttat agattgcagg aattagctta gcagcatttc tatctatgat | 1140 |
| cttctgccac ttcttcccct ctc | 1163 |

<210> SEQ ID NO 11
<211> LENGTH: 881
<212> TYPE: DNA
<213> ORGANISM: Pinus radiata

<400> SEQUENCE: 11

| | |
|---|---|
| aaattagtca atccaaagc agacaacttg ggctctcacc taaattaaca catatacct | 60 |
| accagcttcc atagtttcca acttcctttc aataaatcta ttcaaaagca tgaaaagcat | 120 |
| gactaaggtt caattcccaa gttatggaca cccacctgct ctaggcatat aggaaatcac | 180 |
| aatccaacta acgaccaact acccaaaact ttgaagaaaa tgagtaaaga ctcccccagt | 240 |
| gatattataa ttatatggtc tctctagaac cctttattgc cccttccagt gttatattta | 300 |
| gttccccatt tatatatccc ttgacttatg aaaccattta ggtgcattaa catagtcctt | 360 |
| gactaacaaa aaaattattt aggtgcagta gatacggaaa gtaaccaatg atgctaagaa | 420 |
| actgtgcacg tactttaatg gagttattac ttttattatg gttggtttgg atacattcat | 480 |
| aatggaagca tgtgctcttc atcgttaaag ttgtggtggg gcattcccca ttttccacga | 540 |

-continued

| | | |
|---|---|---|
| gaaaccgaat cccggcgtgg agacgacgac gaaatcgatg gatattcggt ggaaaattca | 600 | |
| cagtaaaatt cctggagaaa aaggttgccg aggtagttga atccaaacc gccgaaatga | 660 | |
| gctggaaacc cgccttctgt cagttagttg agtcatgact gcagctgtct caggtcttac | 720 | |
| actgtaaagg caccttaatg aggcattcat tctggcagtc tggctacgga acttaatagt | 780 | |
| acttgttatt cctgccccaa tatctattta ataggcatcc ccctcacta cttcttgccc | 840 | |
| acaatccctc catagtcctg agcttgagac cattttctg c | 881 | |

<210> SEQ ID NO 12
<211> LENGTH: 638
<212> TYPE: DNA
<213> ORGANISM: Pinus radiata

<400> SEQUENCE: 12

| | | |
|---|---|---|
| aaggtttgct tggaccagcg acacagggaa aaacatggca tgcgggtttg gattaagatg | 60 | |
| aggcccaatc ttaatttgat atgtttgcca aaccttaggt tgtttatcta attttgatt | 120 | |
| ggatctgatc tcttgatgat ttaagggttt tccatgttga cacgcaattg taggttcctg | 180 | |
| ggcactaagg tctaccatgt ggcgaattta tcgagagttg acaattctgg tactgttagt | 240 | |
| gatttgtcac cactctacgg tccctgcaga tctcagattt ttaatggctg cctttgatta | 300 | |
| tctaaaggct agcccctaat cgcggctatg aatgtataaa gaatgtgttc caatgcatta | 360 | |
| gagtactcaa agacatgttg aaggaaaagg acaagtcaag ggacatgagt aataaccaaa | 420 | |
| aaagcacttg gtcctgacca tctgtgtctg attcacactg ggattcacat gttatttaag | 480 | |
| aaaagttgca tcagtgctgc aatcatcaag ccattcctaa tttaccacca tgattagatt | 540 | |
| attttaatgc aagaaaacgc ctatataagg agagctgcag gccccaaggt aatgcagtaa | 600 | |
| tcaaacttga ggagagattt gagagtgttt gtgaaggg | 638 | |

<210> SEQ ID NO 13
<211> LENGTH: 900
<212> TYPE: DNA
<213> ORGANISM: Pinus radiata

<400> SEQUENCE: 13

| | | |
|---|---|---|
| aaatataaca taatctaact attgatgtac attattcgcc tataacaaaa tctaagtatt | 60 | |
| gatgtcacat tattggcata taacaaaatc tttaggataa cccttagtc aagctcttgt | 120 | |
| actttcatgt ttattaacca ataaatcaag ctgatatgga atagcagacg tacgtggtaa | 180 | |
| taataaatgg agtgtaagag ttcgaacatt ttaattcgga gggcagctt atgtggaata | 240 | |
| tcaggcaatc atacaagctt gcttttgggt aataaagacc cacatgtggt aataacaagt | 300 | |
| ggattttaac aaaccaacat tttgataggg aggataggtg gcctggtaag ttagaatgtg | 360 | |
| ctagtcatgc cttttgaaaga agttagttgt ggaagtcaaa catgttcccc acacaacaca | 420 | |
| cctcaccaca caaatgctg gtaggtcatg tgattgatgg atgggcatgt gtatcctcca | 480 | |
| aaaaaaatga atatacacac taaatattct attgacataa tatacaaaga agattaggtc | 540 | |
| tatggaagaa gggaaggcga aggggaagat tgggtcgtgg ggaagattgg gtcgtgtcct | 600 | |
| gctagcacgt tgaataccta cacgccattt cacatctacc catcaacgtc aaatagagca | 660 | |
| tccaaatcag ggcgtggtgg tgtgagggga gagtgaggag aagaagttga aaaattctgg | 720 | |
| ctgaaaatcc acctaacaca cgctcaccag cccctcaacg aggggcacca attatgaata | 780 | |
| ataatagcta aacagagca gcagaagcag agtttatatc tatccattgt cgtctgtaaa | 840 | |
| ttactctgtg agtgtttagt gttttcttct cttattgatt tcagggaca agtaggtggg | 900 | |

<210> SEQ ID NO 14
<211> LENGTH: 603
<212> TYPE: DNA
<213> ORGANISM: Pinus radiata

<400> SEQUENCE: 14

```
aaacaccaat ttaatgggat ttcagatttg tatcccatgc tattgactaa gccattttc       60
ctattgtaat ctaaccaatt ccaatttcca ccctggtgtg aactgactga caaatgcggc      120
ccgaaaacag cgaatgaaat gtctgggtga tcggtcaaac aagcggtggg cgagagaacg      180
cgggtgttgg cctagccggg atgggggtag gtagacggcg tattaccggc gagttgtccg      240
aatggagttt tcggggtagg tagtaacgta gacgtcaatg gaaaaagtca taatctccgt      300
caaaaatcca accgctcctt cacatcgcag agttggtggc cacgggaccc tccacccact      360
cactcaatcg atcgcctgcc gtggttgccc attattcaac catacgccac ttgactcttc      420
accaacaatt ccaggccggc tttcgagaca atgtactgca caggaaaatc caatataaaa      480
ggccggcctc cgcttccttc tcagtagccc ccagctcatt caattcttcc cactgcaggc      540
tacatttgtc agacacgttt tccgccattt ttcgcctgtt tctgcggaga atttgatcag      600
gtt                                                                    603
```

<210> SEQ ID NO 15
<211> LENGTH: 1631
<212> TYPE: DNA
<213> ORGANISM: Pinus radiata

<400> SEQUENCE: 15

```
atcttatgga gttttaaaat atatatatat ttttgggtt gagtttactt aaaatttgga       60
aaaggttggt aagaactata aattgattga gttgtgaatg agtgttttat ggattttta      120
agatgttaaa tttatatatg tagttgtgaa ggagtgtttt atggattttt taagatgtta      180
aatgtgtata tgtaattaaa attttatttt gaataacaaa aaattataat tggataaaaa      240
atgttttgtt aaatttagag taaaaatttt aaaatctaaa ataattaaac actattattt      300
ttaaaaaatt tgttggtaaa ttttatctta aatttagtta aaatttagaa aaaaaaataa      360
ttttaaatta ttaaactttt gaagtcaaat attccaaatg ttttccaaaa tattaaattc      420
atttgacatt caaaatacaa tttaaataac aaaacttcat gaaatagatt aaccaatttg      480
tatgaaaacc aaaaatctca aataaaattt aaattacaaa atattattaa cattatgatt      540
tcaagaaaga gaataaccag tttccaataa aataaaacct catggctggt aattaagatc      600
tcattaatta attcttattt tttaattttt ttacatagaa aatatcttta tattatatac      660
gagaaatata gaatgttcta gtccaaggac tattaatttc caaataagtt tcaaaatcat      720
tacattaaaa ctcatcatgt catttgtgga ttggaaatta gacaaaagag aatcccaaat      780
atttctctca atctcccaaa ataaacctaa ttaatatagt tcgaactcca tatttttggg      840
aattgagaat ttttctaccc aataatatat tttttttata cattttagag attttccaga      900
catatttgct ctgggattta ttggaatgaa ggtttgagta atgaaggttt gagttataaa      960
ctttcagtaa tccaagtatc ttcggttttt gaagatacta aatccattat ataataaaaa     1020
cacattttaa acaccaattt aatgggattt cagatttgta tcccatgcta ttggctaagc     1080
cattttctt attgtaatct aaccaattcc aatttccgcc ctggtgtgaa ctgactgaca     1140
aatgcggccc gaaaacagcg aatgaaatgt ctgggtgatc ggtcaaacaa gcggtgggcg     1200
agagaacgcg ggtgttggcc tagccgggat ggggtaggt agacggcgta ttaccggcga     1260
```

```
gttgtccgaa tggagttttc ggggtaggta gtaacgtaga cgtcaatgga aaaagtcata    1320
atctccgtca aaaatccaac cgctccttca catcgcagag ttggtggcca cgggaccctc    1380
cacccactca ctcaatcgat cgcctgccgt ggttgcccat tattcaacca tacgccactt    1440
gactcttcac caacaattcc aggccggctt tcgagacaat gtactgcaca ggaaaatcca    1500
atataaaagg ccggcctccg cttccttctc agtagccccc agctcattca gttcttccca    1560
ctgcaggcta catttgtcag acacgttttc cgccattttt cgcctgtttc tgcggagaat    1620
ttgatcaggt t                                                         1631
```

<210> SEQ ID NO 16
<211> LENGTH: 786
<212> TYPE: DNA
<213> ORGANISM: Pinus radiata

<400> SEQUENCE: 16

```
aaacgcttca tgccccagaa gccgcactcg atgctttaga ataaaatgga ccattaccag     60
actacgcgcc tccaaaataa caaaaacgtg tattagttaa ccctacata gcacttaaag    120 cttgtcttac tattatttta cgtaattctg tcttttttgac agtggattga ttggaacttc    180
cattctcgat acagttgtat gcgttatgtg aactgaacca acctcggcca aaatatgggg    240
aagattcact tcagaaaaga caggacaacc atctctgatt gtcgacatta atatcggaaa    300
aaattcagtc aaatgatgtg gaaaggttca tctacggaaa ataaaatagc tctgagatga    360
cccgttacat ttagtgcata gcatctttgt caacaagaag aaatttccag ttgtaggact    420
ggtcatcaat ggccgtgcct gcaacgcttt ttcgcaacag gaaacacgga ctaaaaaacg    480
cggtctatct gtcatttgac ggtacgtttg gcactgagcc cgaaaaaatc ccattggtag    540
aatttagaag agggagcttt cactcgaaaa ttctgtacca caagcggtgg cctcacaata    600
acaaattatt atacccacat ggaaaatgtt aaatcggacg gtccgacggt cgaccaaaga    660
caaaattgat gagaaagttt tgagggtggg tgataaagta agcgcgtctt ttcacaggca    720
tctgcattat aaacctgcaa ctccaacttt catcacaaca aatttcattt tccccttctc    780
tgaggc                                                               786
```

<210> SEQ ID NO 17
<211> LENGTH: 898
<212> TYPE: DNA
<213> ORGANISM: Eucalyptus grandis

<400> SEQUENCE: 17

```
aaaaaattta taactaatat tggtacaatt agaaattctc ttgccttcct taatcttgct     60
gttaactcct ccatttagg cgtagacaac tatttttttt ccacaaaaat gaaacagttc    120
ctaaatagac taacgccttt taagctggta gtagacagac cgacacaaaa tcctgaacag    180
gcatgtaccg acacaaagag attcatttca cgagtaaatt tgaatttcga caactaattc    240
tacacatcgg taatcacgca aatatatcag atcggcaaaa agttatattt tagacagtga    300
cgtgacatct caagcaccca atccctctca acaggtgaag agccatattt tcattacata    360
aaggcatttt ttttttttaa tttttaatag gtggtccgac cgacaagata ttattatttt    420
tctatttgca tgaagaagaa aaagattggt tttgaccaca atggtttgtc ctctcgttac    480
ccattttata tttggcaagt ttggtgattg attgtagaag aaacacgaaa cacacgagca    540
aaagtaaagg actccaaacc caaatttaa tccacaaacg aatttaccca cataaaaaaa    600
ggggagatta tgattaaatt cgttgaataa tgcgacccctt taggagaagg cttattaagc    660
```

```
aagcatcgac ggaagctaca cactcctttt ggggagaggc tagtgggtgc aacaactacg    720
attcgggtag agctaagctt tgtccccagt ggcggtactg ccatgaccag ggctctaaat    780
caaaacctaa tctgccaacc tcaaaacaaa cgctgtctcg ccccccccgg ctgcgctata    840
taatgcagcc gatggcgtcc ttcctttctc gaaccctaag cagatcaaga gtttgagt     898

<210> SEQ ID NO 18
<211> LENGTH: 563
<212> TYPE: DNA
<213> ORGANISM: Eucalyptus grandis

<400> SEQUENCE: 18
gtgaagagcc atattttcat tacataaagg catttttttt tttaattttt aataggtggt     60
ccgaccgaca agatattatt attttttctat ttgcatgaag aagaaaaaga ttggttttga    120
ccacaatggt ttgtcctctc gttacccatt ttatatttgg caagtttggt gattgattgt    180
agaagaaaca cgaaacacac gagcaaaagt aaaggactcc aaacccaaat tttaatccac    240
aaatgaattt acccacataa aaaaggggga gattatgatt aaattcgttg aataatgcga    300
ccctttagga aaggcttat taagcaagca tcgacggaag ctacacactc cttttgggga    360
gaggctagtg ggtgcaacaa ctacgattcg ggtagagcta agctttgtcc ccagtggcgg    420
tactgccatg accagggctc taaatcaaaa cctaatctgc caacctcaaa acaaacgctg    480
tctcgccccc cccggctgcg ctatataatg cagccgatgg cgtccttcct ttctcgaacc    540
ctaagcagat caagagtttg agt                                             563

<210> SEQ ID NO 19
<211> LENGTH: 524
<212> TYPE: DNA
<213> ORGANISM: Eucalyptus grandis

<400> SEQUENCE: 19 aaatttttt ttttttttgg gtgggtagta ggatctgtca gagtaaagtg acttaacgcc     60
aattctcgac atttcagact aataaaatat ttacagatgc aacgtctcac tctctccttg    120
caaaaccaga aagggacagc aagcaagaag agggggaaga gaagacttgc gttttaagca    180
aggggagtgc tgacttttca agcgacttaa ttaatctgtt tagcacccac tttggttcgt    240
ttgatcttct cgtgatttat tatttaccta tgtacagctg cggttgaaat ggcctctctc    300
gcttaaatgg tagtttgtcc tttttcttggg gtggttgctt tggaaatatt cttttagaag    360
caggggcaaa gaaatggagt ggcatctgat gcttcttcaa cactttgcag ccatatcgag    420
aatatatacc tagagagaga gagagagaga gagagagaga ggagcagtgg agaagaagga    480
gaagaagaaa agggtcagat cagatccagt tgttgggagc aagt                      524

<210> SEQ ID NO 20
<211> LENGTH: 638
<212> TYPE: DNA
<213> ORGANISM: Pinus radiata

<400> SEQUENCE: 20
ctgtattcat cactttacac ccatgattcc aaaccctaca catttacact gataaccaag     60
ggttcaggtt ctttccaatt cattttaatc caggatgata taaatttga atagcacaat    120 agcatattcc aactgacata tccctacatt tgggatctct ttccacgtta taaatggctt    180
caatttaggg atccctttcc acattatata actgggttca cagtggtttg aagatagctg    240 tggttttgaag atagctgtat atgttatcaa aatgacagct cccttgccag ggaccatcgc    300
```

| | | | | |
|---|---|---|---|---|
| ttgaatgatg | agatcccgcc | tgtaaggcaa | cttgcagcat | gattatttta catctgcttg | 360 |
| accaattatc | taacaatata | cgcggtgtcg | tcgttcggtt | aaataatagt gaaacttcct | 420 |
| cgtgttgtcc | ctgcagttac | gtatgtcttg | ttcttttttt | tgtttaataa catacagcag | 480 |
| agcaagtgtt | gggtgaataa | atattgggaa | gaagctgcag | cgttcacgtt cattcattca | 540 |
| ctcatcgtga | gcagcagtac | atcaacagtt | cttgaagaac | attgataggt tggctatttc | 600 |
| aatccttca | tggggaatat | ttaagtctgg | atccgagc | | 638 |

<210> SEQ ID NO 21
<211> LENGTH: 862
<212> TYPE: DNA
<213> ORGANISM: Pinus radiata

<400> SEQUENCE: 21

| | | | | |
|---|---|---|---|---|
| aaatataaca | taatctaact | attgatgtac | attattcgcc | tataacaaaa tctttaggat | 60 |
| aaccccttag | tcaagctctt | gtactttcat | gtttattaac | caataaatca agctgatatg | 120 |
| gaatagcaga | cgtacgtggt | aataataaat | ggagtgtaag | agttcgaaca ttttaattcg | 180 |
| gagggggcagc | ttatgtggaa | tatcaggcaa | tcatacaagc | ttgcttttgg gtaataaaga | 240 |
| cccacatgtg | gtaataacaa | gtggatttta | acaaaccaac | attttgatag ggaggatagg | 300 |
| tggcctggta | agttagaatg | tgctagtcat | gcctttgaaa | gaagttagtt gtggaagtca | 360 |
| aacatgttcc | ccacacaaca | cacctcacca | cacaaaatgc | tggtaggtca tgtgattgat | 420 |
| ggatgggcat | gtgtatcctc | caaaaaaaat | gaatatacac | actaaatatt ctattgacat | 480 |
| aatatacaag | gaagattagg | tctatggaag | aagggaaggc | gaaggggaag attgggtcgt | 540 |
| ggggaagatt | gggtcgtgtc | ctgctagcac | gttgaatacc | tacacgccat ttcacgtcta | 600 |
| cccatcaacg | tcaaatagag | catccaaatc | agggcgtggt | ggtgtgaggg gagagtgagg | 660 |
| agaagaagtt | gaaaaattct | ggctgaaaat | ccacctaaca | cacgctcacc agcccctcaa | 720 |
| cgaggggcac | caattatgaa | taataatagc | tagaacagag | cagcagaagc aaagtttata | 780 |
| tctatccatt | gtcgtctgta | aattactctg | tgagtgttta | gtgttttctt ctcttattga | 840 |
| tttcagggga | caagtaggtg | gg | | | 862 |

<210> SEQ ID NO 22
<211> LENGTH: 693
<212> TYPE: DNA
<213> ORGANISM: Eucalyptus grandis

<400> SEQUENCE: 22

| | | | | |
|---|---|---|---|---|
| aaacggacag | gaaccaaact | ggatcggatc | caattcctag | tcctaaaacc aaccaatccc | 60 |
| cactttctaa | ttttggaat | cggtcctata | ggttccattt | tgaaatcgat cgcccttata | 120 |
| tgaatgaaag | agcgctcaca | tgtaccgtta | gatggtatag | acctaataat ctgataatct | 180 |
| gatggctcat | tgcgttttga | gctcacatgg | agcgagatta | tgtaataatg acgtcaggga | 240 |
| gaggagagga | gagaagatga | agagaaagct | gtggagaaac | aaaacacaag gctcgttgga | 300 |
| agcaacgtaa | acaacagcaa | acaacatcaa | caacggcgac | aaaagaagag agagagagag | 360 |
| agagagagag | aggaaacaaa | aacaaaagca | aaagttgggg | agtgaagagg ggaaaagaaa | 420 |
| gatgatgtga | aaacaaacca | aactctcctt | ttcttccacc | tctcattttc tgtctggtat | 480 |
| atgggggtct | ctctctctct | ccctctctct | ctctctctct | accttctctc tctactttct | 540 |
| ctttcttagg | gggggcgtc | cccagggtct | ccgatcccaa | tatcattccc ccccactctt | 600 |
| ttgctgccat | atacatacaa | aaaaccgaag | cttgtgaaca | acccatctct ctctctctct | 660 |

```
ctccctctct ctttctgcct gcgaaactgt gtc                           693
```

```
<210> SEQ ID NO 23
<211> LENGTH: 934
<212> TYPE: DNA
<213> ORGANISM: Eucalyptus grandis

<400> SEQUENCE: 23
aaaacaatgt agcttctctg tgttatgaaa actaacaaaa gggcacatct atttctccat    60
gaccattata ttcggaggag catggtcaaa cttaaatcaa aatttattat ccataactta   120
caaatttcca atttagctaa actcaaatcc caaagtatag caattctgtt aaaattttat   180
catccgatag tatagagcaa tattttataa tacttacatt gctcagctca attacaaatt   240
ctatttgtcc acaaattcaa acattttaat gatgcattcc acataaaacc aatggtttga   300
gacaccttt caaaaaaag aaaaaaatac actagcattg cttagacaag ttaatcaatg    360
aaaaataact ttatcttgtt tttaattaag gatgaaaagg agttacaaac gcttgtttca   420
agataaatat ttttcaaatc tttaatatta caagaaataa acggaccttc ttatcaacca   480
aaaaaatgta acataaaagg aacttaccaa tttgattgga ctcatttatt gattttgga   540
aaaatgtcgc aaattttcgt tgagttttag ctccatgtac aatttagtca ttgaactttt   600
aatttattca atataattca tgaacttct atacatattt agtccatata aaattaagg    660
gaccaaattg agtattcacc aaaattttag ggaaaatatt gaataaataa aaagttcttg   720
gaccaaattt catattgaaa taaaattcat ggacaaatca ttattccttg attaaacttt   780
tttatgtaga cacccgtaaa tacaacctgc caaggtttgt ttgcaaggcg tttgcaaggc   840
gtttgcactt aagcgggacg gaggcgtcac cagtcaatgg gcatgtccag tggcttcccc   900
ggcttgcgaa taggatgctt cctgaatcat ctcc                              934
```

```
<210> SEQ ID NO 24
<211> LENGTH: 408
<212> TYPE: DNA
<213> ORGANISM: Eucalyptus grandis

<400> SEQUENCE: 24
aaagtttctc tgtagagaga gggagggaga tatatctgcg gtttgcgtct ctatttcgct    60
tgtgcagttt tactactccc caaacacaca cacactctct ctgttctct ccttttccc    120
caaatcagaa gaagaaacga cagtgtagta gtgcagtttc actacaccgt ctatactaag   180
ggtaatcgtt ttttgaaag cacatgcata tagccgttgg aaaggggagg gcaccgagat   240
cgaatcggat ggctgatcct cactagccgt tagagagaga gagagagagg gagggataat   300
catgtgcgga catatatccg caatttgcgt ctctatttcg cttgtgcagt tcactactc   360
cccacacaca ctctctctct ctctctctcc ttttcccca aatcagaa                408
```

```
<210> SEQ ID NO 25
<211> LENGTH: 847
<212> TYPE: DNA
<213> ORGANISM: Eucalyptus grandis

<400> SEQUENCE: 25
ccttgtattt ccccaacatt aaatgaaagc ctacatccaa aaacgtggac ccggcattaa    60
agaaaaaccc catcatctca tccccatcctt tatttcaacc ctaaagtgaa attaagatat   120
aagacgaaac cacccccaac cccccaaaaa aaaatatta agggaattcg ttttttttgaa   180
agcacatgcg gaggtagctg ttggaaaggg gcctctacgt tcggaaggaa tgcgaccatt   240
```

-continued

| | |
|---|---|
| ccatcgagat caaatcgaac tactgatgct cactagctgt tgcgtttaaa ccttctttgt | 300 |
| aaagcgataa gggaattcgt tattttgaaa gcacatgcgg aggtagccat tggaaagggg | 360 |
| cctctacgtt cggaaggaac acgaccgttc caccgagatc gaatcggacc gttgatgctc | 420 |
| actagccatt gtgtttaaag tttctctgta gagagaggga gggagatata tctgcggttt | 480 |
| gcgtctctat ttcgcttgtg cagttttact actccccaaa cacacacaca ctctctctgt | 540 |
| ttctctcctt tttcccccaa atcagaagaa gaaacgacag tgtagtagtg cagtttcacc | 600 |
| acaccgtcta tactaagggt aatcgttttt ttgaaagcac atgcatatag ccgttggaaa | 660 |
| ggggagggca ccgagatcga atcggacggc tgatcctcac tagccgttag agagagagag | 720 |
| agagagggag ggataatcat gtgcggacat atatccgcaa tttgcgtctc tatttcgctt | 780 |
| gtgcagtttc actactcccc acacacactc tctctctctc tctctctcct tttcccccaa | 840 |
| atcagaa | 847 |

<210> SEQ ID NO 26
<211> LENGTH: 473
<212> TYPE: DNA
<213> ORGANISM: Eucalyptus grandis

<400> SEQUENCE: 26

| | |
|---|---|
| aaagataaaa atagtgtgga aaatagattt gagaagtgtt catatatttc gatttatcat | 60 |
| agcaaagatt ttatcgacct attttaggct ttatagtgtg actatttaag ataacgaata | 120 |
| ttaatcgaga gatgcacaat taataagaga tattctcacg atcttgagat atatagaaac | 180 |
| cgacagaaaa tatattgatt atctctaata tagaataata ttctagagaa gtattgtaat | 240 |
| tgtgaccacc aactaaaatg gggcagacaa agtagagggc caggtatagt caaggccagt | 300 |
| gaaaggaaa atgaaatgaa ataaaagaaa agaaaagaaa aatcaaatcc tccaacttgt | 360 |
| gtacaggata cacccgaagc tttgtgtata taaaggccac ttaatatctc ctccaaccta | 420 |
| gcaacacatt cgaaagataa gttgcgctta atcctctccc aaaagagcta atc | 473 |

<210> SEQ ID NO 27
<211> LENGTH: 519
<212> TYPE: DNA
<213> ORGANISM: Eucalyptus grandis

<400> SEQUENCE: 27

| | |
|---|---|
| ctgctgaaat tctcgaggaa gttgagaggt tccagattag atctttacca aacaaaaaaa | 60 |
| aactattgct tatgctaaat tggtcattat aataagattt ttagaatact cgttgagtat | 120 |
| actcaactca agatattata agttttctca attggttttt ctccatttct tatgatccgt | 180 |
| ccacgagctt ggagtcgctt ttgaagatgt agccagccca acagaaccgt tccttcatc | 240 |
| ttcccgcgaa agtttcatgt catctccctc ctctgcatca cgaaccaaac ctctgctctc | 300 |
| tctctctctc tctctctgct tcaacacaat gacaccaaca tcgcaccctc ctcaccttcc | 360 |
| caaccaccgc cataccatct cctttaagca ttccgatgag tccctgatcc accgccttct | 420 |
| cactgagcct ccccgctctc cctcttctcg tctcactttc tcatataaag aagtgaaaga | 480 |
| atacgaggat actccacttg ggtatcgcca agaactcat | 519 |

<210> SEQ ID NO 28
<211> LENGTH: 216
<212> TYPE: DNA
<213> ORGANISM: Eucalyptus grandis

<400> SEQUENCE: 28

```
gtgcggacac gtgtcccctt atcccgccca agaccgcgca aaacctgaaa atcctcacta    60
ttccctcact ttcggcgaat tcgaaacagc gcataaagga acacggaaag aacattctct   120
accccaagac gacgacgacg acgacgacga cgacgccgcg ccttatataa accatcgcca   180
ctcctggcca ttcccttctt tctccccaga tccaat                             216

<210> SEQ ID NO 29
<211> LENGTH: 286
<212> TYPE: DNA
<213> ORGANISM: Eucalyptus grandis

<400> SEQUENCE: 29
aaattatgca atttcttaat caggcctagc tagaaacaag ggcaaggaaa gcccccgacg    60
ggctcttatc tgctgacgtg gcacgccgtg ggtgggcccc ccgggtcttc cttcgacga   120 aacctcatcg tagacaatca atcctcctc tcgatcatta ttgcaaagcc aacacccagc   180
attgaatcga tccccacctt ctcctcctcc tcctcttgat ccttttgtc ccgatgatga   240 tgggtatctg atcagccgat tcaatcccat cgtctccttc cttctc                  286

<210> SEQ ID NO 30
<211> LENGTH: 168
<212> TYPE: DNA
<213> ORGANISM: Eucalyptus grandis

<400> SEQUENCE: 30
aaaaccacaa atggccgcgg gacgtcacaa ttttttttc cttctagaag ctctatagtc    60
aaagctgatc tataaatttt tgggaaccac aaccaccatg tctcgccacc ttcgctcgaa   120
ccttatcacc accaccgccc ttgagccctc ctccatcaac tcttcttc                168

<210> SEQ ID NO 31
<211> LENGTH: 748
<212> TYPE: DNA
<213> ORGANISM: Eucalyptus grandis

<400> SEQUENCE: 31
ctgtcacctc tggctggtcg ccgaacctca gcgaccgact ggaggaagaa gaggaaaaga    60
aaaaaataaa aataaaattc taaaatatta aatatattatt aaaagttgtc cacgtcagcg   120
ttgaggccac gttaactagc cggtgtcgag tcagcaaaat tcggccaaaa ttggcacaaa   180
aaaaggttta ggactttttt gacgcttttc ccgtcatgag cctaaataag aaatttaat   240 ttcttcatac cataccaatt atttgatatg agatttttct aactaattca cacatctatg   300
ctaacgctac tcgctcaaaa agcgctcaag ctgaagccaa gtttcaagca tcaagcttat   360
aagccgagcc aagctcgagc acggtgcttc ttttctcggc ctgacccgat tagactcttg   420
actgaacatg acatatgaaa ttgcagagca ttcaatttaa aagattgtga aatttctggg   480
catttattta cctcccctgtt aatgatattg cagagcattc aatttaaaga ttgtgaaatt   540
tctgggcatt tatttacctc cctgttaatg atatttttat ggaatagcgt gcaaagaatt   600
cgggtgcata gtgttgtcct tctcccaacg ccccttata taatctccga acggagcaag    660
catttgctct tccgtaccca cggcattttc cttctcgtga ccttttcccg agaaaacaag    720
aagaagagaa aatccttcca ttgcatcg                                      748

<210> SEQ ID NO 32
<211> LENGTH: 1161
<212> TYPE: DNA
<213> ORGANISM: Eucalyptus grandis
```

```
<400> SEQUENCE: 32
ctgacgccta acatgtacct taactgtaat gtagcagcgc aggtcgtcat agcagaggcc      60
ggtcatgctg gtcaggtagt tactttaaaa atctggaaag cttcttgtt gttgtctttg     120
ctgcttttct tcgctctttc ggcgaacttc ccagtcgatt catcggtcta agaatagac     180
acggaggtta tcgcaaactt atgcagagat tccttgcggt acgcaaatgc atgtttaata     240
gatcattatg ttaaatagat aatatagtga ctttcaggat ccgttttgttt tgcaaatttt    300
ttttcctaaa attggtaaca tgcaacgctt gaaattatca attagcgaaa atattatta     360
tcatagagaa caatttatat aaaccttctc ccagcctaat aagcatgcct ggttctctaa     420
tatcaaagaa aaagaggagc tagatctcgc ctttagaatg atttgaagta attgcagtta     480
gcttgaagac attcgtagat gtcgattgat caatgctttt ggaagtacta gagatgcgca     540
cgcatacgtg cgatatccaa actatttccg ttgaccctca cgaaaatctc cgtacagacc     600
gttgttgcta attctttatt tgccgtaaaa tctgcatgaa tccataaatt caatgattcg     660
aacgtgacgc agaggaagtt atgcattcca aaagatagca tttatttaa ataaagaagt      720
gaagattaca atatcttagg tgcctattta tagagaggtc gtcatctaga aaataaccaa     780
gtaaccgaaa ttgaataaca aaattaaaaa atatatattg ataaaagggg aaagttatca     840
aaatacaact agaaaatctc caaaatgtgt ttgaaatctg tgatatctcg gatttgtggg     900
atcgcttgct ctcatgacgc tctaatgttt ccataaaggc atttgcggag attattgtgt     960
cggattattc agcttgcaag aaaagttata gtgcgagcaa accatataaa ataacaataa    1020
ataatggcaa aaactatcgc cgaaaattct ccaatgacga caaggactcc gatttagtgg    1080
aattttgtgc tgtcaatttg actataaata cccgcccgtt gtgctcccaa atcgagtgca    1140
agaaatgaaa ctcctgacca a                                              1161

<210> SEQ ID NO 33
<211> LENGTH: 563
<212> TYPE: DNA
<213> ORGANISM: Eucalyptus grandis

<400> SEQUENCE: 33
gtgaagagcc atattttcat tacataaagg cattttttt tttaattttt aataggtggt       60
ccgaccgaca agatattatt attttttctat ttgcatgaag aagaaaaaga ttggttttga    120
ccacaatggt ttgtcctctc gttacccatt ttatatttgg caagtttggt gattgattgt     180
agaagaaaca cgaaacacac gagcaaaagt aaaggactcc aaacccaaat tttaatccac     240
aaatgaattt acccacataa aaaaagggga gattatgatt aaattcgttg aataatgcga     300
cccttagga gaaggcttat taagcaagca tcgacggaag ctacacactc cttttgggga     360
gaggctagtg ggtgcaacaa ctacgattcg ggtagagcta agctttgtcc ccagtggcgg     420
tactgccatg accagggctc taaatcaaaa cctaatctgc caacctcaaa acaaacgctg     480
tctcgccccc cccggctgcg ctatataatg cagccgatgg cgtccttcct ttctcgaacc     540
ctaagcagat caagagtttg agt                                             563

<210> SEQ ID NO 34
<211> LENGTH: 524
<212> TYPE: DNA
<213> ORGANISM: Eucalyptus grandis

<400> SEQUENCE: 34 aaatttttt ttttttttgg gtgggtagta ggatctgtca gagtaaagtg acttaacgcc        60
```

```
aattctcgac atttcagact aataaaatat ttacagatgc aacgtctcac tctctccttg      120
caaaaccaga aagggacagc aagcaagaag agggggaaga gaagacttgc gttttaagca      180
aggggagtgc tgacttttca agcgacttaa ttaatctgtt tagcacccac tttggttcgt      240
ttgatcttct cgtgatttat tatttaccta tgtacagctg cggttgaaat ggcctctctc      300
gcttaaatgg tagtttgtcc ttttcttggg gtggttgctt tggaaatatt cttttagaag      360
caggggcaaa gaaatggagt ggcatctgat gcttcttcaa cactttgcag ccatatcgag      420
aatatatacc tagagagaga gagagagaga gagagagaga ggagcagtgg agaagaagga      480
gaagaagaaa agggtcagat cagatccagt tgttgggagc aagt                     524

<210> SEQ ID NO 35
<211> LENGTH: 1795
<212> TYPE: DNA
<213> ORGANISM: Eucalyptus grandis

<400> SEQUENCE: 35
atcattaata tcattagaaa gatatattac atttttaaaga tgaataaaca tttgaaatgt       60
tttctctaca actaaaaaaa aaatcattgc ctctacaact aaaaaaaaga tcattgccca      120
ttatgacatt tcatttttttt tctaatcaca tcaaattact ttagaataac tatccagctg      180
ccaaaaaaaa atagtattgt atatctaaaa taaatatatt gacaaatgcc aactaaatta      240
ggtatcaacg aatacctctt actttcctac aatcgaagat gtaaagacta atgtacattt      300
cttcatgatt atgtactaat cgattacaaa accaacatt ttttttagt tcttgaattt      360 cttttatttta ggaacagtat ccaccaaata tgttctttag ctaaagaatg atatatatta      420
tttttaaaat tgcgattgga ttcttcatat gttatatctt gttcaaatat tattattttg      480
atttgatttt caaaataaaa cagaaaaata aatctcatct cgttcctttt ttcaatagtg      540
aaaatcccac caaattcatt gacaaaaaat catgaaaaca gtaaagcttg tatttttcatt      600 cccaacttta aaactggtgg gtgacattcc aaatgatcat atggtcatat actaatttc      660 ccaatttctg agcgtgctca acgtgattgt acccttttat tttcggatca tgccaggtca      720
atagagaaaa tttatcaaag attagtttaa tgatgaattg ggaccaacct ctcaagtcca      780
tgaaactgcc gtatgcgcaa ccgtaagctc cgttccaatt tttctaatga ttcaaggaaa      840
aataaataaa taaaaaagtc catcgtcgat gtgacatttc gcctgcgctc tccagctact      900
taatcaatca atatatacga attatttagc acatgacagc attttccct tttcctggc      960 gtcctcctag ggtggatccg gaccgtggat cgaactacag gagtggcggg gctctccgcc     1020
accgacagca aagtcaatat caatcatcga tggcagtcgc tttccggacg attcatactc     1080
atccgagtcc atttccccact tcaacctcaa gtccctcctc gtccacaaat gtaaaaatga     1140
aaaaatggag ggcagattag actgaatttt agctgtacaa cacatgttgc ctgtgcttca     1200
cgttcaagat ccacggttgc tttgctgttg cactcgcacc aactgtactg aatctcccctt     1260 tatttctctc ttttaatttt tttttttttg ggtgggtagt aggatctgtc agagtaaagt     1320
gacttaacgc caattctcga catttcagac taataaaata tttacagatg caacgtctca     1380
ctctctcctt gcaaaaccag aaagggacag caagcaagaa gagggggaag agaagacttg     1440
cgttttaagc aaggggagtg ctgacttttc aagcgactta attaatctgt ttagcaccca     1500
ctttgcttcg tttgatcttc tcgtgattta ttatttacct atgtacagct gcggttgaaa     1560
tggcctctct cgcttaaatg gtagtttgtc cttttcttgg ggtggttgct ttggaaatat     1620
tcttttagaa gcaggggcaa agaaatggag tggcgtctga tgcttcttca acactttgca     1680
```

```
gccatatcga gaatatatac ctagagagag agagagagag agagagagag aggagcagtg    1740
gagaagaagg agaagaagaa aagggtcaga tcagatccag ttgttgggag caagt         1795

<210> SEQ ID NO 36
<211> LENGTH: 542
<212> TYPE: DNA
<213> ORGANISM: Eucalyptus grandis

<400> SEQUENCE: 36
aaactcatac tcttgataag atgcagacat tgctggcgtt caacaaggaa agaaaaaga      60 aggaataaga caaagtgaaa gagaaaaagg aaaaaaaaag taaagtaaaa taaaatatca    120
ttaaaaattg tgtatgttag ggttgttagg catttatgtc cgcaccaatt gacgcattta    180
tgtccgcacc aatcgaacca tttatgttcg caccaatcga cgcatttatg tctgcaccac    240
tcatctgcac caattggcca aaattggcca gaatgattga attgacataa ttgcaaaata    300
tctaagactg aacaagcaaa aaaaaaagtt atgaccgaat tagaaaaatt acaatagatt    360
tatgactttt tttgtaattc cccccaccta actctgtcaa acctgctaat atagactaat    420
tcattcatat atttatatat acacactcat aggttgatat atgaatatgg gggtacgtat    480
aaccctatgt gctaaaatct tggagaactt cctattcata tcagaagaag aaccgatcct    540
gt                                                                   542

<210> SEQ ID NO 37
<211> LENGTH: 858
<212> TYPE: DNA
<213> ORGANISM: Eucalyptus grandis

<400> SEQUENCE: 37
aaaacagatt gttttagatt gataacgttt tcctatcatg ccggcatcat ctcaattttg     60
aattatatcg gagcattaaa tataaaagtt aggttacgga tgaatgataa cgcagaccta    120
gtgagaaaat tagtataatc acgataaaaa tatccatata gacatcacaa aaatgccgcc    180
cgatctgatg aaatccgaca aataacacaa acatatatat gtccaagact tggacttcaa    240
gtcgacatgc ttgtgcatgc acaatttggg gccataaaat tgggcatgtg agaacctcaa    300
accgttaaga gatcaggtat ttactttgtt tgtcgactga cgagacgtgc acgcatttca    360
caccctcttc tcattgatct tcaaagcttt tccgaactca cgatggttcc agaaaggcga    420
tgttttgctg acagagggag cgttcgatgg agcttctcca tcacttaatt tgtcccttca    480
agatgaaaaa agtaagaggt ccaccgtacc aaaacattct tccacccaga agaaaaccac    540
agtagctgga gggagtcaag catgtcagaa gcacagaaac tgggaatggc taaaaagcaa    600
gtcttgaccc ttaacccacc ccactggttc acctaccgca cctcgggtta ggtattgctt    660
gctgaggtgt cacttttcgc caaagtcatg tctctctttt ggaatcttct tattggtccg    720 tctcgttttcc tcgttgctgg atgctggtag cgttttttgtc catatatata tgcagtccat    780
atgtatcccc gtcactcctc atctatgctc ctacccggca acttcccact acgataagca    840
gcaagttttc ggctctgt                                                  858

<210> SEQ ID NO 38
<211> LENGTH: 547
<212> TYPE: DNA
<213> ORGANISM: Eucalyptus grandis

<400> SEQUENCE: 38
atcaggtatt tactttgttt gtcgactgac gagacgtgca cgcatttcac accctcttct     60
```

```
cattgatctt caaagctttt ccgaactcac gatggttcca gaaaggcgat gttttgctga    120
cagagggagc gttcgatgga gcttctccat cacttaattt gtcccttcaa gatgaaaaaa    180
gtaagaggtc caccgtacca aaacattctt ccacccagaa gaaaaccaca gtagctggag    240
ggagtcaagc atgtcagaag cacagaaact gggaatggct aaaaagcaag tcttgaccct    300
taacccaccc cactggttca cctaccgcac ctcgggttag gtattgcttg ctgaggtgtc    360
acttttcgcc aaagtcatgt ctctcttttg gaatcttctt attggtccgt ctcgtttcct    420
cgttgctgga tgctggtagc gttttgtcc atatatatat gcagtccata tgtatccccg     480
tcactcctca tctatgctcc tacccggcaa cttcccacta cgataagcag caagttttcg    540
gctctgt                                                              547
```

```
<210> SEQ ID NO 39
<211> LENGTH: 862
<212> TYPE: DNA
<213> ORGANISM: Eucalyptus grandis

<400> SEQUENCE: 39
aaacactttc tgtaaactta ttttgcaaa caatccaaag ccaaaaagt aaagaaacta       60 ttttcagata ggaaattttt ctcaaaacaa ggatcgtcga tgggactgga gctctcagcc    120 caaaaagaa aaaagaaag gtaatgtgat gtaagagaga ggaaagtaaa gttgaagaac      180
gtgtatgcaa agcgacatga tggggagag catttgatgg acaatcattg ggccaactca     240
catgaagtcc ttacaacaaa cagttggagg acgatgcagc tccagctcga ttcagcgact    300
ccaattatat ttccctctct ggtcctctcc tcctttccat gcgcaatcca gctaagtttc    360
tattccatgg ccccttttgct actagggtca catctgccag atattttct ggtatgcagc     420 taaaagcata gtagtgccct ttggaaaagt tgatcatagt aactgggctg gtccagttta    480
attagagcaa tctatgatga aattactaat gaatttttgg gaagttcggt ttttggtttc    540
tcggaatttc tcaccaatat cattgcttca atattagtta aaatagacga ctgaaaagat    600
catgatagat aaaaaaaagg gagtggccaa attattttc tctaattctt acttaactta     660
agcttcatgc atgctgccca tcttgtgttt ggtcattaac taacctagaa ggagggggg     720 aaaaggtaaa acatgtcata aaaggtttag ttagacccct cacccaaaat gattgcccaa    780
tgccaccact ttaatcatca actttccaac caacacttgt ttttttggct tccctttctt    840
atcctccatt ctcctctctc ct                                             862
```

```
<210> SEQ ID NO 40
<211> LENGTH: 611
<212> TYPE: DNA
<213> ORGANISM: Eucalyptus grandis

<400> SEQUENCE: 40
atcaatgagt gaagggggc ggcacaagag agatatactt acacatgctc cccctagact       60
agacgacaga cgcaatttac acatgtccga gacatacggt catgaaatgg gaattctgat    120
gtagaaatag catgaaccca tttagcaaag aattgagaac tgggccggaa ctctgctcgt    180
gttaactaat ccaagcgtcg gtcaagctgt gcgcacgcat gggtgggaag ggggcggggg    240
taggtgcaca gggaatttgg tttggggggtt agagttggtc aaaagccgaa acggtgttag    300
gcattgggct ttttggcttt cggcttcaag acaatttgaa ggggagatgg ggcgtgccat    360
ctgctctccc cctgccatat gacccatcat cccctctcca tctccatcta cctctaccta    420
cccccgcccc cttcctcttc ttctccttttt ctctttcctt cttcgaaaaa ttttaattta    480
```

```
ttaaaatatt tattgccccc cccctcccc ctctccaaaa ccgaatttaa cccaaccctc      540
tctctttccc tccacccaaa tctctacaca tcatcatcat catcatcatc atctcctccc      600
ctcccttttc t                                                           611
```

<210> SEQ ID NO 41
<211> LENGTH: 498
<212> TYPE: DNA
<213> ORGANISM: Eucalyptus grandis

<400> SEQUENCE: 41

```
aaaatcactt aacggcttca cccaatatac tagttatctc ataagtggca atctaaaaaa       60
aaaaacacta tagttacgtc gatgaaaggt ccgacttatc tgttcgaaat cagaacctga      120
atttctatta ttgatctaaa caaatcacgt cgagtgtgat ctagtttatg aaaaatacta      180
caaagaaatg aaaaaaaaaa tgttaaattg aatgcaattt attagcaatg ggtttgaaaa      240
ttagtaatag tatatctatt gtcatgcaag atatgaatat tttagatcct tctagaagca      300
cggataactt atgactcgat gttttcttaa atctttggac acttgtcatt ttttcataga      360
gaagcgacga gaagatcttt cgcggctgtt tcacctaccc caacctttgt ccctatgcat      420
cttggctgag atgtcaacct taggcttccg acacctttga ctctctctcc tccatcgtcc      480
tcatctctct cctgtata                                                    498
```

<210> SEQ ID NO 42
<211> LENGTH: 362
<212> TYPE: DNA
<213> ORGANISM: Pinus radiata

<400> SEQUENCE: 42

```
aaaaaagttt cccaatctct aagcaaccat aaagctcaac cactctctgt cctgtgcccc       60
aacgtctacc agacgattag gtatgcactg cagttcttcg tctgtcatgc taccagacag      120
ttaggtaacc actaatgtct taggtggtga ttgatattga tgtttcttct gcaaacatgt      180
gaatcaatgt gtatcgctgg aatatgacac tgtggatcac tggatataca tagagagatc      240
tgctctgtcc atttttaaca gattcatctc aattttcttg ttccaatgtc aacattttct      300
caactgctct gccccatctt tattaaaagg gaacatctac cctgcatttc cacactccaa      360
tc                                                                     362
```

<210> SEQ ID NO 43
<211> LENGTH: 810
<212> TYPE: DNA
<213> ORGANISM: Pinus radiata

<400> SEQUENCE: 43

```
cctataaaaa aagatttat taagagcatt tggaaaacta tcatctttcc aggaccataa       60
aactatttaa tagttcaata aagatgaagt agttactatt taatagttta ataaaaatta      120
agtagtctaa cagttatata gttatatata tgtgtgtgtt ttgggtatgt tttcaggttg      180
aatgatgtat aattgagtaa ggattttttt tggaattagt gaattttttt ttttcagaat      240
aacaattcta tatatatcat aaaaataaat tttaaataaa aaaatctaa ataaaaatta      300 tttaaaaaaa cactaaaacc attagtatac caacacttca atttaatgat ggataaaata      360
ataagctagc tctgcttaac attacactgt ggtgagtttg acatgaaaaa atagatctct      420
gctttcagaa gtacgcattt ttaaatttaa aaaagtttcc caatctctaa gcaaccataa      480
agctcaacca ctctctgtcc tgtgcccaa cgtctaccag acgattaggt atgcactgca      540
```

```
gttcttcgtc tgtcatgcta ccagacagtt aggtaaccac taatgtctta ggtggtgatt      600
gatattgatg tttcttctgc aaacatgtga atcaatgtgt atcgctggaa tatgacactg      660
tggatcactg gatatacata gagagatctg ctctgtccat ttttaacaga ttcatctcaa      720
ttttcttgtt ccaatgtcaa cattttctca actgctctgc cccatcttta ttaaaaggga      780
acatctaccc tgcatttcca cactccaatc                                       810
```

<210> SEQ ID NO 44
<211> LENGTH: 334
<212> TYPE: DNA
<213> ORGANISM: Pinus radiata

<400> SEQUENCE: 44

```
aaaactaatt ttcaaaatat gaggaaaaaa gcgagaccac gaaaaaatca ttgaaaaaga       60
ccttgcaaaa ttcaggactt gctctcacca acctcgccag acttttgacc gtgctcatgc      120
ttgtgtcatg cttgcatatc tatacgtgtc acatcgaccg tccgatctat catgaaaaga      180
acggtcatga tgaaatctca actaaaccca ctgcgttaaa ttttcgaaca gtgagaaagt      240
aatcgtataa ataccctaa gctcttagac cgagaacgca tgcagcattc ggctctcatt       300
ctgaggttca tctggctgaa gtttgaactg tgct                                  334
```

<210> SEQ ID NO 45
<211> LENGTH: 476
<212> TYPE: DNA
<213> ORGANISM: Pinus radiata

<400> SEQUENCE: 45

```
atcatcacca gtgccaccta agaacgcgtt tgtattgaga taccatctat tttttcggat       60
gcaattacta gttaataatt tataacatta ttaggggtgg ggtccagaaa atgaaaaaaa      120 gaaaagaaa attgaaattt taaaactaat tttcaaaata tgaggaaaaa agcgagacca      180
cgaaaaaatc attgaaaaag accttgcaaa attcaggact tgctctcacc aacctcgcca      240
ggactttgac cgtgctcatg cttgtgtcat gcttgcatat ctatacgtgt cacatcgacc      300
gtccgatcta tcatgaaaag aacggtcatg atgaaatctc aactaaaccc actgcgttaa      360
attttcgaac agtgagaaag taatcgtata aataccccta agctcttaga ccgagaacgc      420
atgcagcatt cggctctcat tctgaggttc atctggctga agtttgaact gtgctc         476
```

<210> SEQ ID NO 46
<211> LENGTH: 536
<212> TYPE: DNA
<213> ORGANISM: Pinus radiata

<400> SEQUENCE: 46

```
aaagatgcta caatttgatt tcttttttagt taaatttaat cagaaatata gaaaaaggtt      60
aggaagatgt ttgcagtcgt aaatatgagc gcaatggcct ttagtccacg cgtagtggca      120
catcttacac ggatacttgg ttttcagccc cacacaactg caagggttgc ttcgaaggta      180
actcttacgt tggtttgagt gcccaaaaca tattagcttt ttattttgtg tcactgtcga      240
catcgttggc cctaatttta tcgtatgatc aggccctgat ctctctcgcc accatttcct      300
tataaggcgc cagcagacaa gcacagctct ggaaggaaca tgggtgagtg acattaaagc      360
aacgcgatga cctcatacca gcttcaacag cttacaccat aagacacgct ttcccatgga      420
catcctccta cgtatcactc acttgcctat atattcatgc aactccgtca cagtttttata      480 ataattcagg tgcctttat atcagtagta tcaacggata cacccaggt gattgt            536
```

-continued

<210> SEQ ID NO 47
<211> LENGTH: 680
<212> TYPE: DNA
<213> ORGANISM: Pinus radiata

<400> SEQUENCE: 47

| | | | | | |
|---|---|---|---|---|---|
| aaattcatgt | ttgtcatagg | ttatggtatt | ttgcacacat | gaaacaaatt | ttacaattga | 60 |
| ctttgattaa | gatattaaat | ctacaatagg | ttatcaactc | cacgtgataa | tgaagtaaaa | 120 |
| agactggatg | gctaagtcaa | taaaacaacc | aaataatcaa | gcaatgatag | cttctatcaa | 180 |
| ataaggatgg | ttcagctaga | tccaggcgaa | atatgattca | gccagatacg | aaaaggcgag | 240 |
| cggttgaaat | gtttgaatgt | ttgcggggtc | cctggttgct | tcggaggtta | ttctacgtaa | 300 |
| tttattcgtt | ataccttgcc | ttctaagcat | cgcaaactgt | gatttcttaa | caaactcgat | 360 |
| gcatgcgcca | taaccaacaa | aaccatttag | ttgagtttac | ggtcttcaca | attcatgctc | 420 |
| agtcaccttc | aactattatg | acagattagg | tgctacttat | tctctcgtta | ccctttagag | 480 |
| tgaactttaa | tccaaattgt | caggtgattt | gggcccccag | gcgatggatc | cagcgacagg | 540 |
| ggaacgcaag | tttggtggtt | gtggcagtgc | agttggtatg | ccccagagag | ttttaagact | 600 |
| tcagatttgt | gttcagtatc | aggagctgct | atggaaaaag | caaccatata | aaactattgc | 660 |
| cattcgcaca | ggaacagaac | | | | | 680 |

<210> SEQ ID NO 48
<211> LENGTH: 1607
<212> TYPE: DNA
<213> ORGANISM: Pinus radiata

<400> SEQUENCE: 48

| | | | | | |
|---|---|---|---|---|---|
| cctttgggaa | tgaactttga | gaccacctcc | aacccggatt | ctgaaatcca | tccagcaatt | 60 |
| ccaaagttcc | aaaccgaaat | aaacatccca | ccataccatg | gcattcggaa | aaaagctagg | 120 |
| ctaagctgaa | aatcactgtc | ataacccagt | aagaccatgc | cactaatagc | aagagaacca | 180 |
| tacaccaaca | tgcaaagcca | tgcatgtcca | aaccagctag | gaaatcacac | atgcaaaggg | 240 |
| ttacctgcaa | gtattcctgt | tgaagttgct | tgatcctact | ttcttttcct | tgagccttgc | 300 |
| ttgccttcct | ttcctttgct | tgattttcct | ttccttgctc | caaactagag | tgctctaaga | 360 |
| aaactctaag | tgaccaagag | agtgagagag | agagagaata | atgagagtcc | aaacatgaac | 420 |
| ttgacaaaag | ccatgaactg | atcctcagaa | gtcattttat | gcacgaggct | tctattttct | 480 |
| tcattttcca | tcattttcct | tcaatttcct | catcacatgc | aacgtgcgac | ttttcacccc | 540 |
| gttttcctcc | taatttcttt | tattttcata | aataaatgtg | ccaaaaatgc | ctcttgcctt | 600 |
| agcctttgcc | agtttcctta | gccaaaacac | acatccaatg | atgcccacta | ggatatcttt | 660 |
| gcccaacatt | aagcctggaa | taaatgtctc | ttaatcgtgg | tcttatttg | cttttattaa | 720 |
| cttttattac | atgaactttt | cactaaagct | attacaaaga | tatatttatt | atggcaatta | 780 |
| tgtttgattt | ttgaagagct | agtaactttt | agtttattat | ggccttttcc | gtaaacttat | 840 |
| tttcttgaaa | atctctataa | atccaatgaa | aaatttatag | aatatatgtt | gtgttttctt | 900 |
| cactacctct | aataaatttt | ttacttagta | atctacaaag | ccatttatta | aaaaattcaa | 960 |
| gttaattaaa | aattaatatc | atttcaaaag | tcttttaat | atagtcaaag | tttattaaat | 1020 |
| tctatgatgt | atatttctt | taaataaatg | aagaatccat | tttttacttt | aaaaccatat | 1080 |
| attttttata | acgttgataa | atagcatgca | tttatataaa | caaatatata | tttttataac | 1140 |
| gttaagagat | tgttaaaact | tttaaataat | taatatttta | tttattgttt | tgaaaatgtc | 1200 |

```
atgatttcca cctacctcgc ccatcaaatc ttgctgcaaa ccaggcttac ccaaccccac    1260
acccacaata tattttttggg atctggtgcc cccacctttg atcacagtga acaccataaa    1320
gacaaattat aaaggcaagg ggacttggca cccatgaggc aaccgaaagc aacaaatcat    1380
ttttttccaa agagatgagt gtatgccaac gaagaaacac gatgaaccca cgtgtcattg    1440
gccaactccc actttcgaca aaaagaagga aattagaatt aaaaaggcga ataaaaattg    1500
aaaggccatt taaaatagaa ggaagaatag cctatatggt agatttaaat gcttttttga    1560
aatccggtta ctcgcaagat tatcaatcgg gactgtagcc gaagctt                  1607

<210> SEQ ID NO 49
<211> LENGTH: 881
<212> TYPE: DNA
<213> ORGANISM: Pinus radiata

<400> SEQUENCE: 49
aaattagtca aatccaaagc agacaacttg ggctctcacc taaattaaca catatacccct     60 accagcttcc atagttttcca acttcctttc aataaatcta ttcaaaagca tgaaaagcat    120
gactaaggtt caattcccaa gttatggaca cccacctgct ctaggcatat aggaaatcac    180
aatccaacta acgaccaact acccaaaact ttgaagaaaa tgagtaaaga ctcccccagt    240
gatattataa ttatatggtc tctctagaac cctttattgc cccttccagt gttatattta    300 gttcccatt tatatatccc ttgacttatg aaaccattta ggtgcattaa catagtcctt     360
gactaacaaa aaaattattt aggtgcagta gatacggaaa gtaaccaatg atgctaagaa    420
actgtgcacg tactttaatg gaggtattac ttttattatg gttggtttgg atacattcat    480
aatggaagca tgtgctcttc atcgttaaag ttgtggtggg gcattcccca ttttccacga    540
gaaaccgaat cccggcgtgg agacgacgac gaaatcgatg gatattcggt ggaaaattca    600
cagtaaaatt cctggagaaa aaggttgccg aggtagttga aatccaaacc gccgaaatga    660
gctggaaacc cgccttctgt cagttagttg agtcatgact gcagctgtct caggtcttac    720
actgtaaagg caccttaatg aggcattcat tctggcagtc tggctacgga acttaatagt    780
acttgttatt cctgccccaa tatctatttta ataggcatcc cccctcacta cttcttgccc    840
acaatccctc catagtcctg agcttgagac cattttttctg c                       881

<210> SEQ ID NO 50
<211> LENGTH: 900
<212> TYPE: DNA
<213> ORGANISM: Pinus radiata

<400> SEQUENCE: 50
aaatataaca taatctaact attgatgtac attattcgcc tataacaaaa tctaagtatt     60
gatgtcacat tattggcata taacaaaatc tttaggataa cccccttagtc aagctcttgt    120 actttcatgt ttattaacca ataaatcaag ctgatatgga aatagcagacg tacgtggtaa    180 taatttaaatgg agtgtaagag ttcgaacatt ttaattcgga ggggcagctt atgtggaata    240
tcaggcaatc atacaagctt gcttttgggt aataaagacc cacatgtggt aataacaagt    300 ggatttttaac aaaccaacat tttgataggg aggataggtg gcctggtaag ttagaatgtg    360
ctagtcatgc ctttgaaaga agttagttgt ggaagtcaaa catgttcccc acacaacaca    420
cctcaccaca caaaatgctg gtaggtcatg tgattgatgg atgggcatgt gtatcctcca    480
aaaaaaatga atatacacac taaatattct attgacataa tatacaaaga agattaggtc    540
tatggaagaa gggaaggcga aggggaagat tgggtcgtgg ggaagattgg gtcgtgtcct    600
```

```
gctagcacgt tgaatacctg cacgccattt cacatctacc catcaacgtc aaatagagca    660
tccaaatcag ggcgtggtgg tgtgagggga gagtgaggag aagaagttga aaaattctgg    720
ctgaaaatcc acctaacaca cgctcaccag cccctcaacg aggggcacca attatgaata    780
ataatagcta gaacagagca gcagaagcag agtttatatc tatccattgt cgtctgtaaa    840
ttactctgtg agtgtttagt gttttcttct cttattgatt tcaggggaca agtaggtggg    900
```

<210> SEQ ID NO 51
<211> LENGTH: 603
<212> TYPE: DNA
<213> ORGANISM: Pinus radiata

<400> SEQUENCE: 51

```
aaacaccaat ttaatgggat ttcagatttg tatcccatgc tattgactaa gccattttc     60 ctattgtaat ctaaccaatt ccaatttcca ccctggtgtg aactgactga caaatgcggc    120
ccgaaaacag cgaatgaaat gtctgggtga tcggtcaaac aagcggtggg cgagagaacg    180
cgggtgttgg cctagccggg atgggggtag gtagacggcg tattaccggc gagttgtccg    240
aatggagttt tcggggtagg tagtaacgta gacgtcaatg gaaaaagtca taatctccgt    300
caaaaatcca accgctcctt cacatcgcag agttggtggc cacgggaccc tccacccact    360
cactcaatcg atcgcctgcc gtggttgccc attattcaac catacgccac ttgactcttc    420
accaacaatt ccaggccggc tttcgagaca atgtactgca caggaaaatc caatataaaa    480
ggccggcctc cgcttccttc tcagtagccc ccagctcatt caattcttcc cactgcaggc    540
tacatttgtc agacacgttt tccgccattt ttcgcctgtt tctgcggaga atttgatcag    600
gtt                                                                  603
```

<210> SEQ ID NO 52
<211> LENGTH: 1631
<212> TYPE: DNA
<213> ORGANISM: Pinus radiata

<400> SEQUENCE: 52

```
atcttatgga gtttttaaat atatatatat tttttgggtt gagtttactt aaaatttgga     60
aaaggttggt aagaactata aattgattga gttgtgaatg agtgttttat ggatttttta    120
agatgttaaa tttatatatg tagttgtgaa ggagtgtttt atggattttt taagatgtta    180
aatgtgtata tgtaattaaa attttatttt gaataacaaa aaattataat tggataaaaa    240 atgtttgtt aaatttagag taaaaatttt aaaatctaaa ataattaaac actattattt    300
ttaaaaaatt tgttggtaaa ttttatctta aatttagtta aaatttagaa aaaaaaataa    360
ttttaaatta ttaaactttt gaagtcaaat attccaaatg ttttccaaaa tattaaattc    420
atttgacatt caaaatacaa tttaaataac aaaacttcat gaaatagatt aaccaatttg    480
tatgaaaacc aaaaatctca aataaaattt aaattacaaa atattattaa cattatgatt    540
tcaagaaaga gaataaccag tttccaataa aataaaacct catggctggt aattaagatc    600
tcattaatta attcttattt tttaattttt ttacatagaa aatatcttta tattatatac    660
gagaaatata gaatgttcta gtccaaggac tattaatttc caaataagtt tcaaaatcat    720
tacattaaaa ctcatcatgt catttgtgga ttggaaatta gacaaaagag aatcccaaat    780
atttctctca atctcccaaa ataaacctaa ttaatatagt tcgaactcca tatttttggg    840
aattgagaat ttttctaccc aataatatat tttttttata cattttagag attttccaga    900
catatttgct ctgggattta ttggaatgaa ggtttgagta atgaaggttt gagttataaa    960
```

-continued

```
ctttcagtaa tccaagtatc ttcggttttt gaagatacta aatccattat ataataaaaa    1020
cacattttaa acaccaattt aatgggattt cagatttgta tcccatgcta ttggctaagc    1080 cattttctt  attgtaatct aaccaattcc aatttccgcc ctggtgtgaa ctgactgaca    1140
aatgcggccc gaaaacagcg aatgaaatgt ctgggtgatc ggtcaaacaa gcggtgggcg    1200
agagaacgcg ggtgttggcc tagccgggat ggggtaggt  agacggcgta ttaccggcga    1260
gttgtccgaa tggagttttc ggggtaggta gtaacgtaga cgtcaatgga aaaagtcata    1320
atctccgtca aaatccaac  cgctccttca catcgcagag ttggtggcca cgggaccctc    1380
cacccactca ctcaatcgat cgcctgccgt ggttgcccat tattcaacca tacgccactt    1440
gactcttcac caacaattcc aggccggctt tcgagacaat gtactgcaca ggaaaatcca    1500
atataaaagg ccggcctccg cttccttctc agtagccccc agctcattca gttcttccca    1560
ctgcaggcta catttgtcag acacgttttc cgccattttt cgcctgtttc tgcggagaat    1620
ttgatcaggt t                                                         1631
```

<210> SEQ ID NO 53
<211> LENGTH: 1163
<212> TYPE: DNA
<213> ORGANISM: Pinus radiata

<400> SEQUENCE: 53

```
aaacagagca gataacacta aaaagaccaa ccctgttagg aggggagaaa caaaaaagat     60
cacactaaaa agaccaaccc tcttatctaa acttattttc tcttatctct accccttcta    120
ttttgaacct ttatcatttt gatagaaaat atatgttaat aaccattaaa cctacattgt    180
caagctagtg taacttatat gttaataacc attaaaccta cattgtcaag ttagtgtaac    240
tcctttggtg ggggtggttg tcttcctctt caatctcatg ctatgacaca cttgtttttt    300
aataacatag gccgacaagt ttgagccatt atctatcttg attcctcgaa atgataaata    360
gatgttgtca gtggacttga aaaaaaccaa gtagggaaca ccacgtaatc tttccaatgg    420
cattaaaagc tactttgaaa tatgtaacac ttagcaatcc ttccaaggca ttaaacctac    480
tctaacctat ggaacactta gcatccttcc cacggttgat aataaatgat tgattcctca    540
gaataacaaa taaaaaaaaa ctataaaact tactctaaaa tataaaatga gtatggaaca    600
cgtggcaatc cttcccatgc tcggcggtag ctactctctc cagagatttg aataacacag    660
gcgccgcaat tatgagagag cagtggagtt aagacttagt agccatggtt attttgaacg    720
cgtggcaatt cttccaaagg ttggtagtta ctctatccag agatttgaat aacacaaatg    780
ctgcagttat gagagagtag tagagttaag tcttgtcagc aatgatagtt acgaacaacc    840
gtaatttctg gctatctctg tgtttattgg tcgtttactt gctacagtgc tctcacccca    900
catggtaaca gtgttcgatg gccatgattt ctccccaccc cgccaaacct ctacgttttt    960
attcttttaa taactcctaa tttaatatat aagaggggc  aaggtgttca tacagattcg    1020
tgcaaacgac ctgagttcag cacaagttta gtcattccat gcgaactcga ctggctcacg    1080
agatccctcg ctgcagttat agattgcagg aattagctta gcagcatttc tatctatgat    1140
cttctgccac ttcttcccct ctc                                            1163
```

<210> SEQ ID NO 54
<211> LENGTH: 638
<212> TYPE: DNA
<213> ORGANISM: Pinus radiata

<400> SEQUENCE: 54

```
aaggtttgct tggaccagcg acacagggaa aacatggca tgcgggtttg gattaagatg      60
aggcccaatc ttaatttgat atgtttgcca aaccttaggt tgtttatcta attttttgatt  120 ggatctgatc tcttgatgat ttaagggttt tccatgttga cacgcaattg taggttcctg   180
ggcactaagg tctaccatgt ggcgaattta tcgagagttg acaattctgg tactgttagt   240
gatttgtcac cactctacgg tccctgcaga tctcagattt ttaatggctg cctttgatta   300
tctaaaggct agcccctaat cgcggctatg aatgtataaa gaatgtgttc caatgcatta   360
gagtactcaa agacatgttg aaggaaaagg acaagtcaag ggacatgagt aataaccaaa   420
aaagcacttg gtcctgacca tctgtgtctg attcacactg ggattcacat gttatttaag   480
aaaagttgca tcagtgctgc aatcatcaag ccattcctaa tttaccacca tgattagatt   540 atttttaatgc aagaaaacgc ctatataagg agagctgcag gccccaaggt aatgcagtaa   600
tcaaacttga ggagagattt gagagtgttt gtgaaggg                            638

<210> SEQ ID NO 55
<211> LENGTH: 786
<212> TYPE: DNA
<213> ORGANISM: Pinus radiata

<400> SEQUENCE: 55
aaacgcttca tgccccagaa gccgcactcg atgctttaga ataaaatgga ccattaccag    60
actacgcgcc tccaaaataa caaaaacgtg tattagttaa accctacata gcacttaaag   120
cttgtcttac tattatttta cgtaattctg tcttttttgac agtggattga ttggaacttc  180
cattctcgat acagttgtat gcgttatgtg aactgaacca acctcggcca aaatatgggg   240
aagattcact tcagaaaaga caggacaacc atctctgatt gtcgacatta atatcggaaa   300
aaattcagtc aaatgatgtg gaaaggttca tctacggaaa ataaaatagc tctgagatga   360
cccgttacat ttagtgcata gcatctttgt caacaagaag aaatttccag ttgtaggact   420
ggtcatcaat ggccgtgcct gcaacgcttt ttcgcaacag gaaacacgga ctaaaaaacg   480
cggtctatct gtcatttgac ggtacgtttg gcactgagcc cgaaaaaatc ccattggtag   540
aatttagaag agggagcttt cactcgaaaa ttctgtacca caagcggtgg cctcacaata   600
acaaattatt atacccacat ggaaaatgtt aaatcggacg gtccgacggt cgaccaaaga   660
caaaattgat gagaaagttt tgagggtggg tgataaagta agcgcgtctt ttcacaggca   720
tctgcattat aaacctgcaa ctccaacttt catcacaaca aatttcattt tcccccttctc  780 tgaggc                                                              786

<210> SEQ ID NO 56
<211> LENGTH: 1302
<212> TYPE: DNA
<213> ORGANISM: Pinus radiata

<400> SEQUENCE: 56
aaacaacaaa aaataacaat ctacctagaa attatattac caaatttcaa ttaaaaaacc    60
catttcttag attattaaac tacaccatta taattttcat aataactact aatacaccat   120
tataaatttc ataatactat tcatcccatt ataaatttca taataacttc taatacacca   180 ttataaatt t cataatacta ttcatcccaa tatgtgctac catttagata tttttgagcc   240
aaaacccaac ccgaacaaaa atttgtaatc tcgagattaa tcacaaaatt tgactcgatt   300
catatgcaaa ttggaataat tactcgtcat ggatgagatc ttaccgttgg tgtgatcatg   360
atgacggcca actttggcac gcttcatatc acaaattgca caactactc tgctttttaat   420
```

```
ggatgaccat tgatgacgac caagcttgac acgattcata tgagagaaag aactcaaaca      480
atctactgca atgtgaaaag ccatgggcac cgccaagata tttaattgtc caacgcgtaa      540
caattagtta cccccaatgg gcattggact tgcctttgtc ttgatgtcga aaacaagggg      600
ggatttcctc tctttaagaa aaatagaaaa aacaaaaccc ctgcacagct gggttctcct      660
ttcttcaagc ctggtttggc ttcaacataa agaaacaaaa cccattccat ggtgttgtct      720
tattgtgggt ttgcctaatt caatgttatt agtggttgaa acttcattac agcaggatgg      780
gagagccaac ctcaagagag tgactctgta accatcaatc ttccgcattg ccctgctgcc      840
atggatgtac tggcgaaaat aaagggtcaa ctttgcttaa agatgcagtc agctagagtt      900
taactcaagg aggcaaccgg cttctatgta atacctgtgg aatgaaaacg aatcccatgt      960
accgaattaa gggaaaactg ggtgcagaga ttttgtttgg tttagactct agatatggta     1020
ttacagctcc gattgggtgg tcgaaatacg tcagagcacc ccacattgcg taattcttca     1080
ggtatcagat gcctgcctag tctacataca tgagttgcag tttctcttca gcagtggggt     1140
ttggcggctc tgacagtaca gttagtagag actatctatt ttccgtgtac acaacgcttg     1200
caatgcagat ctgggcgcta ttataaaaga tcaaacaaga gctaggcttt cagaattgcc     1260
tgaaagctgc tgccaattgc atagatctgc tcaaggcacc ac                       1302

<210> SEQ ID NO 57
<211> LENGTH: 638
<212> TYPE: DNA
<213> ORGANISM: Pinus radiata

<400> SEQUENCE: 57
ctgtattcat cactttacac ccatgattcc aaaccctaca catttacact gataaccaag       60
ggttcaggtt ctttccaatt catttttaatc caggatgata ataaatttga atagcacaat      120
agcatattcc aactgacata tccctacatt tgggatctct ttccacgtta taaatggctt      180
caatttaggg atccctttcc acattatata actgggttca cagtggtttg aagatagctg      240
tggtttgaag atagctgtat atgttatcaa aatgacagct cccttgccag ggaccatcgc      300
ttgaatgatg agatcccgcc tgtaaggcaa cttgcagcat gattatttta catctgcttg      360
accaattatc taacaatata cgcggtgtcg tcgttcggtt aaataatagt gaaacttcct      420
cgtgttgtcc ctgcagttac gtatgtcttg ttcttttttt tgtttaataa catacagcag      480
agcaagtgtt gggtgaataa atattgggaa gaagctgcag cgttcacgtt cattcattca      540
ctcatcgtga gcagcagtac atcaacagtt cttgaagaac attgataggt tggctatttc      600
aatcctttca tggggaatat ttaagtctgg atccgagc                              638

<210> SEQ ID NO 58
<211> LENGTH: 1350
<212> TYPE: DNA
<213> ORGANISM: Pinus radiata

<400> SEQUENCE: 58
atcttatcac attttctcaa gagaagggtt gtgaccaact ttaaattttt ggtctctttg       60
atggtggtaa attggggcaa tgagactcaa cattgttaga acatttacct ttctcatact      120
ttggaggatc tattaagaca aaagctctca tgtatttcct ttacatgcat gcacatttat      180
agggaataga atggagtagc aaattgactt tctaaggaag gcctactctt gactcggggg      240
ttgtggcagg tagttgaaga ctagggagcc ggtcactacc aatttttacca tcaaccattt      300 acagacgaga tacaaaatga tgattatgtt taattttga aactttcact tattaatttt       360
```

```
tgtgacgcat tcataacata ttatgttagt atatatgttc gttcacaggt tgttggcttt      420
ggtaacacta tactagtatt tctttgtgat tattttttat gtaatgcaat atagccctaa      480
atgaatattg tgaaagtgat attttcagg agcatcaaga ccatcttcat ttgtaaatat       540
gtgataaaag gggggtgtga taaattttag tattttgtta tttttaataa aataggaagt      600
gaagattatg taaatattat tttctaaata aaggatatg agagaatagt ttaggaaaaa       660
gaattgggat agaattccta tgttttttca attaaaatta ggataagaat ggagaataaa      720
gcttcacgct ttaaatcatt atgtaaaacg aaaaagcct gcttttgtaa aagataaggt       780
ctgagaagac ctatccctta tgtatgtatc cgttattatt ataaataaag aggtagctaa      840
tctctcaagg gagagagagg agcgagcgct ctggaaaaag atggatgatg tcttgttaat      900
attgttaata tggatgcgcg tagttaatag tttatttgga ctgtgtatta agcattgaat      960
ggttagctgt atatgttatc aaaatgacag ctccccttgcc agggaccttc gcttgaatga    1020
tgagatcccg cctgtaaggc aacttgcagc atggttattt tacatttgct tgaccaatta    1080
tctaacgata tacgtggtgt cgttattggg ttaaacaata gtgaaacttc ctcgtgttgt    1140
ccctgcagtt acgtatgtct tgttcttttt tttgtttaat atcatacagc agagcaagtg    1200
ttgggtgaat aaatattggg aagaagctgc agcgttcacg ttcattcatt cacccatcgt    1260
gagcagcagt agatcaacag ttcttgaaga acattgatag gttggctatt tcaatcctct    1320
catggggaat atttaagtct ggatccgagc                                     1350

<210> SEQ ID NO 59
<211> LENGTH: 700
<212> TYPE: DNA
<213> ORGANISM: Eucalyptus grandis

<400> SEQUENCE: 59
atcaattcaa gtaaaaaatt ttaatcctaa cttagtcata aacttttatg caatattcca       60
atataatccg tcagtcaata ttaatcggaa ttgttgacgt agcgatgcgc cacgtagaat      120
gactaacgat ggctaaaccg ctatagtagc gatttctgac aaatattaac tgaatgacta      180
tattttcctc attattcagg ttatattgtt ttgtttcat gctatttccc caatagcaaa       240
tttgttcacc tgctcctgga aattccttac gacgactcac cacttattct aacgaatctg      300
atgggtgatt cttgatatta tttgaccatg acataataaa tgtcaaggga aaagagaaa       360 aaaataagaa aagcgaagaa atccaccggt catcattagg acagacacat tatacgccgt      420
cataagggaa aatgaaattt aactaaacat cactaacgtc aaccaaactc gaaaacaaaa      480
cttgaactgc agtagctaga tgtagctctt ggttcagccc ccagaaccat cgcctatcgg      540
gttgatggtt gaagatgtga tcttggtcct aatcacctaa tcaacgaacc accgtttctc      600
attcgctccc tccgtataaa aacctcgagg cttgtcctat cttggagcat cgcatccaag      660
aaacaccatc tcatcctgtc tcagtcccca tcatcacttg                            700

<210> SEQ ID NO 60
<211> LENGTH: 1032
<212> TYPE: DNA
<213> ORGANISM: Eucalyptus grandis

<400> SEQUENCE: 60
gtcgttttta tattgtctag ccacattagc atgaaaaaca atgttgtttt gcatttcctt       60
tgtcggaaaa ttgccgcgtt ggcattttgg ttggaatgac acttaaatga tccattttgt      120
tttgattttg acacttaagt attactttcc aaagttttga cacttaagtg tccattcgca      180
```

```
ctaagttttg gcatttgagt gttcctccgt atcaagtttt gacatttgta atgtactttt       240
gctcataatg ctaatgtgat aatgagacta aattaaacat atattaaaat ttcagaatct       300
acattaaata atttaaaaat ttatgaatca tattacatat tacgataaag ttcaagaact       360
atattaaaaa aattaaatat ttatgggtca cattacatac gagtgaaaat ttaaggacta       420
tttattttgt tatttctttt tccattaaca aaaatcttcc ccacctcatt ttaaattcga       480
gaaaagaaga aaagcaaaga aaataatag agaggaaggg acccaactcg agattgggct        540
ccattgatgg aaactcgcga tctactccat ctcgactcga cagcccatcc tctgaagata       600
acatcatcgt ccgcaccgca ttgcacccta ccttctgggc tgaatgacca cattgccccct     660 ccaccaaatc tatccgttgc ctcgaatgcc ggatggcaaa gcagcaattc ccgcaaaagt       720
ccgagcccat ttcctccgg ccaaatcgag aaaggactct tgattttga aaactgggcg         780 ggcaactaac cttggttagg cgcctccatc attaacccca caccaaagtt aacacccccg       840
ctttcgctgg cactttctaa atcgaaccgc ggttaacgta accgcggtta accaaccaga       900 tattttttcaa ttttttccag tggcgctcta tatatcttta aacttcccct ctgcatttcc     960
catcagctct gcaagtcctc ctccatcttc ttcttcttca tcgtcatctt ctcggaaggc       1020
gtcttgataa ac                                                          1032

<210> SEQ ID NO 61
<211> LENGTH: 529
<212> TYPE: DNA
<213> ORGANISM: Eucalyptus grandis

<400> SEQUENCE: 61
atcaaagtta gtcgcacttt tacataccca actgtacctc caaagtgcac cattgaactt        60
gtgacaacgt ttagatttag gtaattattc agaaaacgaa agcgaccaca ggtttatgaa       120
ttgtcacgca tgacgtcatt aattaagcga caagacgtgc gccaaggcca tgcattcctc       180
tgcggctatc cttcttcctg gcaacagttc aattcctcag acggtctggt caaacccgaa       240
gctcgactag ccttttctca accaaaccct ccaagaaagc ctaaggacag catgccctcg       300
cgcggatcaa cacgaccgac gagcatcgaa cttgcgtaac ttaccccacc aaacggtccc       360
cttcgaggtc aaaccccacg cgaacgaccg atgaatcgaa catctaatct cgcctctcct       420
ctcctccact gctatatatt tcagctactc taacacactc tcatcaccac caacttcaaa       480
ctctctctct ccctccctcc ctccctctct cgctcacaca tacacacat                  529

<210> SEQ ID NO 62
<211> LENGTH: 710
<212> TYPE: DNA
<213> ORGANISM: Eucalyptus grandis

<400> SEQUENCE: 62
ctggagttca cattgagctg gtgccgatcg atccgtttct tacattttt catcccggtc         60 cgtctccatt ctctgcctcc gtcggcatct tgggcgacga gaggaggagg agatacgcgg       120
tagctgacga gttcgaggcg caacttttct tcgattaact tttaactcga caccgatcat       180
gctttaagca cttacccttt tcgagaaaca ggagatggac atggagttcg acgtaaagat       240
cccgtctttg attacagaaa aagcatgctc agaggaggag gaatgatatt tcctgtttcc       300
atggtggtga taaaagcttt gattttttcct tttcaatgac gtagctcgag tggccgataa     360
tcgacaagga ggtccaacta ttagcaccag aatggaaaag aagagggaga tagatagcga      420
ctaccacaag ctacattaca aggattaata taagcaaaat tactgcaata cgatattgac       480
```

```
ccgattggct ttggatgata aaaaaacaat tctatattca atcacacgtc ttcgtccccg     540
ggaaagcaat gatccaaatc atgtcaagga gctatactcc taagcccacg ttagcccaca     600
ctcttctcga aagacatatc aaatcaatac actcactctc tctattaata ttcaatttct     660
gcataatttc ttctgtcact gcccaagacg ttctgtagca ctaaggggtg                710

<210> SEQ ID NO 63
<211> LENGTH: 365
<212> TYPE: DNA
<213> ORGANISM: Pinus radiata

<400> SEQUENCE: 63
aaattcacat tcttttctt cgcacgaaga aaggttaaag atacaactcg gattgtatta      60
aaggaaagag attggaacaa acagaatctg gaatataaga ataccagat cgcgggcac      120 ggccacagtt taacggccag ccgaaaggcc ggtccgttgg gtctgccggt gacttggtcg    180
tgtgagggaa tctctggagt ccggatccgg tcttgccttg agacctacca caaccacagc    240
agttaatgca gtttacatcc tattaatata aataccaaat cgccattcca aattattatc    300
acaacaacaa atctgatttg atttcgatgc agtgaagctc ttcattttgc agtgacagtg    360
acgtt                                                                365

<210> SEQ ID NO 64
<211> LENGTH: 1304
<212> TYPE: DNA
<213> ORGANISM: Pinus radiata

<400> SEQUENCE: 64
ggacaaacga gatttattc tcatccagtt ccatctattc tctgtcactg taacttgtag      60
agattatatt aacgatgggg ttatgatcgc ttcacgtttc cagatagaat ggagagaaca    120
acagcaagga aatcgacagg ccataactta atggggtcac tgtaaggcct tccggggcgt    180
aaacacgaag ctttgtacag agagtccacc caaaaacaag catcatcaca gtgacaataa    240
ttgaaaaaga aatgaaaagc tccactgggc ttctctttct ggaaccttct ctccgaagaa    300
atcgacttac agaatttaaa aaatttaaaa tgatgttctg tagcaaccta ggccctccac    360
tgtcaccata cctgccccctc cattgtcaca ttctatcttc tcatcttaaa caccacgcat    420
ctcgcttttc cactgcatgc agagatcgac gatatctttg cttgatatct aagtcgaatt    480
ctgaccgcaa acctccatca gacttgcgca catcttaata gatggcgctt gtttgtgccc    540
aaggggttct gggtactatt tgaggactga aggtgttatg cttcagagat ttggaggcct    600
agggttcgat tcacagccgt tgagatttcg acagaatttg gattttttt ctctggctgt    660 ttgaggagaa tgagagagat attgcacatc cagggcgggc agtgcgggaa ccagatagga    720
gccaagttct gggaagtgat atgtgacgag catgggattg ataccacggg ctcgtactgt    780
ggggactccg atctgcagct ggagaggatc aatgtctatt ataacgaggc aagcggcggc    840
cgctatgtgc ctcgggcagt gctgatggat ctcgaacccg ggaccatgga cagcgttcga    900
tcaggtccct atggtcagat cttcaggcca gataacttcg tctttgggca gacaggcgcc    960
gggaacaact gggccaaagg gcattatact gagggggcag aactcattga ctccgttctt   1020
gatgtcgtgc gtaaggaggc cgagagctga gattgtcttc agggatttca agtatgtcat   1080
tccctgggag gaggaacagg atcgggaatg gggactctct tgatttccaa aataagggag   1140
gagtacccag acagaatgat gttgactttc tctgtttttc catcacctaa ggtatcggac   1200
acagtggtgg aaccttataa tgcaactctt tctgtacatc aattggtgga gaatgcagat   1260
```

```
gaatgcatgg ttcttgacaa tgaagcactt tacgacattt gctt            1304
```

<210> SEQ ID NO 65
<211> LENGTH: 2062
<212> TYPE: DNA
<213> ORGANISM: Pinus radiata

<400> SEQUENCE: 65

```
gtatcattat ttcagtcatt atcgataatg ataagcctca aatatgaatc aatagtctct    60
tagtcattta atttatggtt ttcagtgtcg atgtgctctc ctgccagggc tccaccaatc   120
tcctttaggt tcagtgtaca tcgtctgaaa ataagttgac aaggccaggt caatgcagaa   180
gcctcctggc ttggggaccc taagtgtgaa atcaatatat tttcctcgag ttcttgacct   240
gttagcaact tcgacactgc aacttgtcct aatctttgct gtgtattatg tattttgttc   300
caagtattgg agtgtagcac agtggatggt agagaggagg atctagatca gtcactttta   360
catagaatgg agatgatagt aaaagcaact acaattacga tcttgctacc agtcatccta   420
tgttgcatcc catgtggaga agtggaagc ggaggcagga gtttggcgca gcgtttacca    480
gccctaggcg ttgactatgg acaaactgca gacaatcttc ctccaccatc tgcagtagca   540
aagctggttc agagtacaag tatttcaaag ttgagactat atggagcaga tcctgcaatt   600
cttcaagcat ttgctaacac aggaattggg ttagttgtag cattggtaa cgatcaaatc    660
ccatctctga accagctggc tgttgcacag aattggatta agaacaatat cgttcctttt   720
gttcctgcca ctgatatcat tggaatctcg gtggggaacg aggttctgtt cagtggggat   780
gggagtctga tttcccagct cctccctgca ttgcagaacc tacacactgc ccttgttgag   840
gtttcacttg accagcaaat taaggtctcc acacctcatt ctctggccat actttctaca   900
tctgtccccc catctgctgg ccgtttcaat gaaagtttt g acatgaaatc cctgcttgac   960
ttcttgcaga agatagggc cccattaatg atcaacccat accctactt tgcttacaag    1020
agtaatccca ccgatcaaac cctggcttat gcactcttcg agcccaaccc gggcttctat   1080
gacacaaaca gtgggctcac ctataccaac atgtttgatg ctcagcttga tgcagtgtac   1140
tcagccatga aatatctggg ttaccctggt gttgatatag tggtggctga acaggatgg    1200
ccagctgtgg gggatcctac agagacaggg gtgagcttac agaatgcaat tgcttacaat   1260
ggcaacctga tcaagcatgt gacgtccatg acggggaccc cattgaggcc aaataggtac   1320
attcaaacct atattttgc cctctttaat gaggatctga agccaggacc aacttcggag    1380
cgcaattatg ggctgtttaa agttgatatg acaatggctt atgatgtggg tttgttgcaa   1440
tcgccgagtg cagctccatc tcctcctgct ccacgcactg ggggcctgt gacaactcct    1500
cctacaggta aagtttggtg cattgccaag ccggcgccg aagagcaaac tttggaggca    1560
aatttgaact atgtttgtgg acagggcatt gactgtaggc ctattcaacc aggaggtcct   1620
tgctattcac caaatacagt ggcaggccat gctgcttatg ccatgaacgc atactatcag   1680
actgcgggtc ggaacaattg gaattgtgat tttgcgcaga cgggaactct tacctccaca   1740
gatccaagct acggggcctg cgtgtacccg accgtctaag atatgaatca atcaatcaat   1800
cctagtgttt tctattccac ttgttgttcg gtatatattt tccaacttgt cttttcatat   1860
gagtgagatg tatgaggtac ctattttcaa agttgtgata gcatatacat cataagatgt   1920
aatgtgtatg tttgggtttt attccccctt taatgtcgtt actctgacca tataaaaaaa   1980
ttcacagaat ttgtgaatgg tagtattatt tttatttat gtattaagga aatttaagtg    2040
gtgttaaaaa aaggaaaaaa aa                                            2062
```

<210> SEQ ID NO 66
<211> LENGTH: 542
<212> TYPE: DNA
<213> ORGANISM: Pinus radiata

<400> SEQUENCE: 66

```
aaaaaaaatt atgatctgta aataaatata attccatata taatagatat atataaattt      60
tacaacccac agataaatat taactttccg ccaaaataat ttccataaat gaaataaatg     120
acccaatatt acgattttac accaaaatga tttccatatg tatatataaa gcctgtgagt     180
ccaaacgaag catatgaatc tgaatcgcag agggaggctg ccaaccacc attagctatt      240
caatgaagtt ggtagccacc caaacaagtc aattcaagag tcaatcaaac caaactatga     300
ttaaaactac caaccgcact ttctgagcaa cccactttcc ctccctcgct ttactttttg     360
gagtcgtggg ggattttttcc agtgtctcaa tttctataaa tttggcctca catttcctac    420
caactcattg ttaacgggag tcctcttgtc aggctccgct gcttcttgtg atcacacgat     480
acctagtgat ccatagataa ctaaaatgct gtgagcagtc tgaattcttg ctttctttcc     540
cc                                                                    542
```

<210> SEQ ID NO 67
<211> LENGTH: 349
<212> TYPE: DNA
<213> ORGANISM: Pinus radiata

<400> SEQUENCE: 67

```
gtctgtatta ttatattctg ggtcactact caaccccacg gtagtggcgt gacttgcgtc      60
ggcgtgttac agaatccata atcagaaaac gaacggaagc tgcaaaggtg tacgtccaac     120
ggttgcggtg aaaagccatt ggttacgtcc agcggtggaa ttctgtaata ctgaaaggat     180
ttggttacag atggctcgac caaagacaaa atagtaatca atattcaac cgaaagggag      240
aaagttgctt atgggcatca cgttataaaa gtggaactcg actttcatta ccacacattt     300
ctcatttctt tctctgtact gagccattcg ttctcctttc tttcagaga                 349
```

<210> SEQ ID NO 68
<211> LENGTH: 222
<212> TYPE: DNA
<213> ORGANISM: Pinus radiata

<400> SEQUENCE: 68

```
ctggcaactg gctattcctc attcgtcagt gggaatgggg tgggcagacg atcttctaga      60
gcctgtgtgg tgtggggccc ttcgactttt caatggcccg ttggtcacca gcttggacta     120
gttttgctgt ttccatggtg acggttcgtg ctctataaaa taatttaacc gagtgggtat     180
tttgcatggt ggccggattt ccaacaatct caggtattag cg                        222
```

<210> SEQ ID NO 69
<211> LENGTH: 403
<212> TYPE: DNA
<213> ORGANISM: Pinus radiata

<400> SEQUENCE: 69

```
atctaaccca cgatctataa taatagtcaa ggaccctaaa tagaaatatg gccaccaccc      60
taccacgaga gcttatccta atacaaccac gaaagcccct ccactcgtgg aggttataga    120
tttcccccgt gtaaacatat aaaaggaact tttctctttg gtgaccggca acaaccggat    180
actcacccgg tatcgccgaa gaagcttgtt gcgaggttcg cattgaaaac cctcctctct   240
```

```
tcacattctt tgccggtcat ccatcttgct catttctact tccgcctcct cttctcttcc    300
ctcgtctagt gttttctttg cgttgtgtag tgtaatgttt gctgttgctt catatcaata    360
gtggtggaat tttccttcac tgcgagcaga ttttctaagg aga                      403
```

<210> SEQ ID NO 70
<211> LENGTH: 1032
<212> TYPE: DNA
<213> ORGANISM: Eucalyptus grandis

<400> SEQUENCE: 70

```
gtcgttttta tattgtctag ccacattagc atgaaaaaca atgttgtttt gcatttcctt     60
tgtcggaaaa ttgccgcgtt ggcattttgg ttggaatgac acttaaatga tccattttgt    120
tttgattttg acacttaagt attactttcc aaagttttga cacttaagtg tccattcgca    180
ctaagttttg gcatttgagt gttcctccgt atcaagtttt gacatttgta atgtactttt    240
gctcataatg ctaatgtgat aatgagacta aattaaacat atattaaaat ttcagaatct    300
acattaaata atttaaaaat ttatgaatca tattacatat tacgataaag ttcaagaact    360
atattaaaaa aattaaatat ttatgggtca cattacatac gagtgaaaat ttaaggacta    420
tttattttgt tatttctttt tccattaaca aaaatcttcc ccacctcatt ttaaattcga    480
gaaaagaaga aaagcaaaga aaataatag agaggaaggg acccaactcg agattgggct    540
ccattgatgg aaactcgcga tctactccat ctcgactcga cagcccatcc tctgaagata    600
acatcatcgt ccgcaccgca ttgcacccta ccttctgggc tgaatgacca cattgccccct    660 ccaccaaatc tatccgttgc ctcgaatgcc ggatggcaaa gcagcaattc ccgcaaaagt    720
ccgagcccat ttcctccgg ccaaatcgag aaaggactct tgattttga aaactgggcg      780 ggcaactaac cttggttagg cgcctccatc attaacccca caccaaagtt aacacccccg    840
ctttcgctgg cactttctaa atcgaaccgc ggttaacgta accgcggtta accaaccaga    900
tatttttcaa ttttttccag tggcgctcta tatatcttta aacttcccct ctgcatttcc    960
catcagctct gcaagtcctc ctccatcttc ttcttcttca tcgtcatctt ctcggaaggc   1020
gtcttgataa ac                                                       1032
```

<210> SEQ ID NO 71
<211> LENGTH: 1039
<212> TYPE: DNA
<213> ORGANISM: Pinus radiata

<400> SEQUENCE: 71

```
aaataggcta aattagagaa atactatggg ttgtcaaaac ctagaatacg ataatttgac     60
cgaaatattt agataatgta acataacatg acatgcacatt acaacatctc ttccatagag   120
aatctctcaa taaaataaaa tattgcacaa acaaaaccaa ctcaaaactc aatttatatt    180
acacaatata ataataaaca atttcaatta aaaacatttt accttattt attaataaac     240 ctcacactaa cacattgtta aaaagtaaaa ataaaataac aaacgccata taaacccata    300
aaaatttcca aaacaatatt aatatctttta tcatagtttt taagctaaag ttcgatgatc    360
ctttaacatt actagccaca aggatgctta cttccttgca aaataacaat gcaaagaccc    420
aacgcagtga tatgtgattt aacggtaagt atggttgggt gaaaccaaca agactgcagt    480
tcaaattcca ttgagtatat ggcctgctat gatctcagct tggtgaaacc aacaagactg    540
cagttcaaat ctaaatccca ttaattatgt gacctactat aatctgggct taaggagtag    600
gttgctcgct atgtttttggt gttataaagt agccataaag attaaacctc aagctcccct    660
```

-continued

```
aaattaatcc aagaaattac cgattcatta taattaaaaa aaatgcaaat acccaccta      720 aagaaaaaca atgtaaagag caatgaaatc aatttaattg tcttctttta acaccaataa      780
aaatttataa aaacctcata attaaaaaca aagcgttaga cttttggaat aaccttcctt      840
aattgcttct ctaatttatg atttctaagt cataccacga tcggtcgttt tagcaaaagc      900
ctgaaaggca agtagaagat aaacgtatgc ttggaaataa atatatgtca tttttcattt      960
tatatccttc gaatccgtca ttcgtctgaa tgatcagaca aaccctccca gatcctgctc     1020
tgttctgaag cataaacct                                                  1039
```

<210> SEQ ID NO 72
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 72
aatcaaatcc tcc                                                          13

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 73
aatcaaatcc tcc                                                          13

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 74
tctccctcct ct                                                           12

<210> SEQ ID NO 75
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 75
ataaagaagt gaa                                                          13

<210> SEQ ID NO 76
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 76
taaacttatt ttct                                                         14

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 77
taaacttatt ttct                                                       14

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 78
ggagaaacaa aa                                                         12

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 79
aagtaaccaa tgatgc                                                     16

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 80
actttgaaga aaa                                                        13

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 81
tgaggagaag a                                                          11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 82
atcaagctga t                                                          11

<210> SEQ ID NO 83
<211> LENGTH: 12

```
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 83
aatttcattt tc                                                          12

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 84
taaatttgaa ttt                                                         13

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 85
aaatataaca taatctaact attgatgtac attattcgcc                            40

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 86
cccacctacc                                                             10
```